(12) United States Patent
Yamamoto

(10) Patent No.: US 11,154,610 B2
(45) Date of Patent: Oct. 26, 2021

(54) IMMUNOGENIC COMPOSITIONS COMPRISING FIV AND HIV GAG ANTIGENS

(71) Applicant: UNIVERSITY OF FLORIDA RESEARCH FOUNDATION, INC., Gainesville, FL (US)

(72) Inventor: Janet K. Yamamoto, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 0 days.

(21) Appl. No.: 14/511,864

(22) Filed: Oct. 10, 2014

(65) Prior Publication Data

US 2015/0098965 A1    Apr. 9, 2015

Related U.S. Application Data

(63) Continuation of application No. 13/476,835, filed on May 21, 2012, now abandoned, which is a continuation of application No. 12/407,730, filed on Mar. 19, 2009, now Pat. No. 8,182,820, which is a continuation of application No. 10/080,772, filed on Feb. 22, 2002, now abandoned.

(60) Provisional application No. 60/270,745, filed on Feb. 22, 2001.

(51) Int. Cl.

| A61K 39/21 | (2006.01) |
|---|---|
| A61K 39/12 | (2006.01) |
| A61K 39/295 | (2006.01) |
| C07K 14/16 | (2006.01) |
| C12Q 1/70 | (2006.01) |
| G01N 33/569 | (2006.01) |
| G01N 33/68 | (2006.01) |
| C07K 14/155 | (2006.01) |
| A61K 39/00 | (2006.01) |

(52) U.S. Cl.
CPC .............. *A61K 39/21* (2013.01); *A61K 39/12* (2013.01); *A61K 39/295* (2013.01); *C07K 14/161* (2013.01); *A61K 2039/575* (2013.01); *A61K 2039/58* (2013.01); *A61K 2039/70* (2013.01); *C07K 14/155* (2013.01); *C07K 14/162* (2013.01); *C12N 2740/15011* (2013.01); *C12N 2740/15022* (2013.01); *C12N 2740/15034* (2013.01); *C12N 2740/16111* (2013.01); *C12N 2740/16122* (2013.01); *C12N 2740/16134* (2013.01); *C12N 2740/16211* (2013.01); *C12N 2740/16222* (2013.01); *C12N 2740/16234* (2013.01); *C12Q 1/702* (2013.01); *G01N 33/56983* (2013.01); *G01N 33/56988* (2013.01); *G01N 33/6854* (2013.01); *G01N 2333/155* (2013.01); *G01N 2469/20* (2013.01)

(58) Field of Classification Search
CPC .... A61K 39/21; A61K 39/295; C07K 14/155; C07K 14/161; C07K 14/162; C12N 2740/16234; C12N 2740/15011; C12N 2740/15022; C12N 2740/16211; C12N 2740/16134; C12N 2740/16222; C12N 2740/16111; C12N 2740/16122; C12N 2740/15034
See application file for complete search history.

(56) References Cited

U.S. PATENT DOCUMENTS

| 4,358,535 A | 11/1982 | Falkow et al. |
|---|---|---|
| 4,361,537 A | 11/1982 | Deutsch et al. |
| 4,683,195 A | 7/1987 | Mullis et al. |
| 4,683,202 A | 7/1987 | Mullis |
| 4,708,818 A | 11/1987 | Montagnier et al. |
| 4,800,159 A | 1/1989 | Mullis et al. |
| 4,861,720 A | 8/1989 | Pedersen et al. |
| 5,037,753 A | 8/1991 | Pedersen et al. |
| 5,055,391 A | 10/1991 | Montagnier et al. |
| 5,108,891 A | 4/1992 | Croxson |
| 5,118,602 A | 6/1992 | Pedersen et al. |
| 5,135,684 A | 8/1992 | Mohn et al. |
| 5,160,701 A | 11/1992 | Brown, III et al. |
| 5,219,725 A | 6/1993 | O'Connor et al. |

(Continued)

FOREIGN PATENT DOCUMENTS

| EP | 0 860 504 A1 | 8/1998 |
|---|---|---|
| WO | WO 94/02613 A1 | 2/1994 |
| WO | WO 99/60988 A2 | 12/1999 |

OTHER PUBLICATIONS

Fitch, W. M., 1996, The variety of human virus evolution, Molecular Phylogentics and Evolution 5(1):247-258.*

(Continued)

*Primary Examiner* — Jeffrey S Parkin
(74) *Attorney, Agent, or Firm* — Saliwanchik, Lloyd & Eisenschenk

(57) ABSTRACT

The subject invention pertains to materials and methods for detecting, preventing and treating retroviral infections in humans and other animals susceptible to infection by retrovirus. It has been discovered that FIV can be transmitted from cats to humans and that the FIV can infect human cells in vivo and that antibodies generated by the infected person cross-react with HIV antigens. Thus, the methods and compositions of the subject invention can be used to detect, prevent and treat FIV infection in humans and other non-feline animals that are susceptible to FIV infection. The methods and compositions of the invention can also be used to prevent and treat infection by HIV in humans.

9 Claims, 35 Drawing Sheets

Specification includes a Sequence Listing.

(56) References Cited

U.S. PATENT DOCUMENTS

| | | | |
|---|---|---|---|
| 5,275,813 A | 1/1994 | Yamamoto et al. | |
| 5,510,106 A | 4/1996 | Yamamoto et al. | |
| 5,530,101 A | 6/1996 | Queen et al. | |
| 5,565,319 A | 10/1996 | Pedersen et al. | |
| 5,585,098 A | 12/1996 | Queen et al. | |
| 5,693,762 A | 12/1997 | Queen et al. | |
| 5,766,598 A * | 6/1998 | Paoletti | C07K 14/005 424/199.1 |
| 5,807,715 A | 9/1998 | Morrison et al. | |
| 5,846,825 A | 12/1998 | Yamamoto | |
| 5,922,533 A | 7/1999 | Vallari et al. | |
| 6,107,077 A | 8/2000 | Yamamoto | |
| 6,254,872 B1 | 7/2001 | Yamamoto | |
| 6,447,993 B1 | 9/2002 | Yamamoto | |
| 6,544,528 B1 * | 4/2003 | Yamamoto | A61K 39/21 424/184.1 |
| 6,605,282 B2 | 8/2003 | Yamamoto | |
| 7,311,921 B2 | 12/2007 | Yamamoto | |

OTHER PUBLICATIONS

Rolf, S. R., et al., 2015, Conserved epitopes on HIV-1, FIV and SIV p24 proteins are recognized by HIV-1-infected subjects, Human Vaccines and Immunotherapeutics 11(6):1540-1556.*

Li, Y., et al., 1992, Complete nucleotide sequence, genome organization, and biological properties of human immunodeficiency virus type 1 in vivo: Evidence for limited defectiveness and complementation, J. Virol. 66(11):6587-6600.*

Olmsted, R. A., et al., 1989, Nucleotide sequence analysis of feline immunodeficiency virus: Genome organization and relationship to other lentiviruses, Proc. Natl. Acad. Sci. USA 86:8088-8092.*

Matsuo, K, et al., 1992, Highly conserved epitope domain in major core protein p24 is structurally similar among human, simian and feline immunodeficiency virus, J. Gen. Virol. 73:2445-2450.*

Gallo, R. C., Sep. 2005, The end or the beginning of the drive to an HIV-preventive vaccine: a view from over 20 years, The Lancet 366:1894-1898.*

Walker, B. D., and D. R. Burton, May 2008, Toward an AIDS vaccine, Science 320:760-764.*

Letvin, N. L., Dec. 2006, Progress and obstacles in the development of an AIDS vaccine, Nature 6:930-939.*

Ackley, C. D. et al. "Immunologic Abnormalities in Pathogen-Free Cats Experimentally Infected with Feline Immunodeficiency Virus" *Journal of Virology*, 1990, pp. 5652-5655, vol. 64, No. 11.

Azocar, J. et al. "Susceptibility of Human Cell Lines to Feline Leukemia Virus and Feline Sarcoma Virus" *J. Natl Cancer Inst.*, 1979, pp. 1179-1184, vol. 63, No. 5.

Bishop, S. A. et al. "Vaccination with Fixed Feline Immunodeficiency Virus (FIV) Infected Cells: Protection, Breakthrough and Specificity of Response" *Vaccine*, 1996, pp. 1243-1250, vol. 14, No. 3.

Butera, S. T. et al. "Survey of Veterinary Conference Attendees for Evidence of Zoonotic Infection by Feline Retroviruses" *J. Am. Vet. Med. Assoc.*, 2000, pp. 1475-1479, vol. 217, No. 10.

"HIV and Other Retroviruses" CDC Report, HIV and Retrovirology Branch, Division of AIDS, STD, and TB Laboratory Research, pp. 1-20, cdc.gov/ncidod/dastlr/retrovirology/default.htm.

Egberink, H. F. et al., "Use of Western Blot and Radioimmunoprecipitation for Diagnosis of Feline Leukemia and Feline Immunodeficiency Virus Infections" *J. Am. Vet. Med. Assoc.*, 1991, pp. 1339-1342, vol. 199, No. 10.

Goudsmit, J. et al. "LAV/HTLV-III gag Gene Product p24 Shares Antigenic Determinants with Equine Infectious Anemia Virus but Not with Visna Virus or Caprine Arthritis Encephalitis Virus" *Intervirology*, 1986, pp. 169-173, vol. 26.

Hohdatsu, T. et al. "Genetic Subtyping and Epidemiological Study of Feline Immunodeficiency Virus by Nested Polymerase Chain Reaction-Restriction Fragment Length Polymorphism Analysis of the gag Gene" *J. Virol. Methods*, 1998, pp. 107-111, vol. 70.

Hosie, M. J. et al. "Serological Responses of Cats to Feline Immunodeficiency Virus" *AIDS*, 1990, pp. 215-220, vol. 4.

Jarrett, O. et al. "Determinants of the Host Range of Feline Leukaemia Viruses" *J. Gen. Virol*, 1973, pp. 169-175, vol. 20.

Johnston, J. C. et al. "Minimum Requirements for Efficient Transduction of Dividing and Nondividing Cells by Feline Immunodeficiency Virus Vectors" *Journal of Virology*, 1999, pp. 4991-5000, vol. 73, No. 6.

Johnston, J. et al. "Productive Infection of Human Peripheral Blood Mononuclear Cells by Feline Immunodeficiency Virus: Implications for Vector Development" *Journal of Virology*, 1999, pp. 2491-2498, vol. 73, No. 3.

Khabbaz, R. F. et al. "Brief Report: Infection of a Laboratory Worker with Simian Immunodeficiency Virus" *The New England Journal of Medicine*, 1994, pp. 172-177, vol. 330, No. 3.

Khabbaz, R. F. et al. "Simian Immunodeficiency Virus Needlestick Accident in a Laboratory Worker" *The Lancet*, 1992, pp. 271-273, vol. 340, No. 8813.

Kakinuma, S. et al. "Nucleotide Sequence of Feline Immunodeficiency Virus: Classification of Japanese Isolates into Two Subtypes Which Are Distinct from Non-Japanese Subtypes" *Journal of Virology*, 1995, pp. 3639-3646, vol. 69, No. 6.

Kohler, G. et al. "Derivation of Specific Antibody-Producing Tissue Culture and Tumor Lines by Cell Fusion" *Eur. J. Immunol.*, 1976, pp. 511-519, vol. 6.

Louwagie, J. et al. "Phylogenetic Analysis of gag Genes from 70 International HIV-1 Isolates Provides Evidence for Multiple Genotypes" *AIDS*, 1993, pp. 769-780, vol. 7, No. 6.

Matsuo, K. et al. "Highly Conserved Epitope Domain in Major Core Protein p24 is Structurally Similar Among Human, Simian and Feline Immunodeficiency Viruses" *Journal of General Virology*, 1992, pp. 2445-2450, vol. 73.

Merrifield, R. B. "Solid Phase Peptide Synthesis. I. The Synthesis of a Tetrapeptide" *J. Amer. Chem. Soc.*, 1963, pp. 2149-2154, vol. 85.

Morrison, S. L. et al. "Chimeric Human Antibody Molecules: Mouse Antigen-Binding Domains with Human Constant Region Domains" *Proc. Natl. Acad. Sci. USA*, 1984, pp. 6851-6855, vol. 81.

Murphy, F. A. et al. "Virus Taxonomy" In *Virology*, Second Edition, 1990, pp. 9-35, Raven Press, Ltd., New York.

Norway, R. M. et al. "Thymic Lesions in Cats Infected with a Pathogenic Molecular Clone or an ORF-A/2-Deficient Molecular Clone of Feline Immunodeficiency Virus" *Journal of Virology*, 2001, pp. 5833-5841, vol. 75, No. 13.

Olmsted, R. A. et al. "Molecular Cloning of Feline Immunodeficiency Virus" *Proc. Natl. Acad. Sci. USA*, 1989, pp. 2448-2452, vol. 86, No. 7.

Olmsted, R. A. et al. "Nucleotide Sequence Analysis of Feline Immunodeficiency Virus: Genome Organization and Relationship to Other Lentiviruses" *Proc. Natl. Acad. Sci. USA*, 1989, pp. 8088-8092, vol. 86, No. 20.

Ou, C. Y. et al. "DNA Amplification for Direct Detection of HIV-1 in DNA of Peripheral Blood Mononuclear Cells" *Science*, 1988, pp. 295-297, vol. 239, No. 4837.

Pedersen, N. C. et al. "Isolation of a T-Lymphotropic Virus From Domestic Cats with an Immunodeficiency-Like Syndrome" *Science*, 1987, pp. 790-793, vol. 235, No. 4790.

Poeschla, E. M. et al. "CXCR4 Is Required by a Nonprimate Lentivirus: Heterologous Expression of Feline Immunodeficiency Virus in Human, Rodent, and Feline Cells" *Journal of Virology*, 1998, pp. 6858-6866, vol. 72, No. 8.

Pu, R. et al. "MHC-Restricted Protection of Cats Against FIV Infection by Adoptive Transfer of Immune Cells from FIV-Vaccinated Donors" *Cellular Immunology*, 1999, pp. 30-43, vol. 198.

Pu, R. et al. "Dual-subtype FIV Vaccine Protects Cats Against In Vivo Swarms of Both Homologous and Heterologous Subtype FIV Isolates" *AIDS*, 2001, pp. 1225-1237, vol. 15.

Richardson, J. et al. "Shared Usage of the Chemokine Receptor CXCR4 by Primary and Laboratory-Adapted Strains of Feline Immunodeficiency Virus" *Journal of Virology*, 1999, pp. 3661-3671, vol. 73, No. 5.

(56) References Cited

OTHER PUBLICATIONS

Rigby, M. A. et al. "Evolution of Structural Proteins of Feline Immunodeficiency Virus: Molecular Epidemiology and Evidence of Selection for Change" *Journal of General Virology*, 1993, pp. 425-437, vol. 74.

Rigby, M. A. et al. "Immunogenicity of a Peptide From a Major Neutralising Determinant of the Feline Immunodeficiency Virus Surface Glycoprotein" *Vaccine*, 1996, pp. 1095-1102, vol. 14, No. 12.

Saiki, R. K. et al. "Enzymatic Amplification of βGlobin Genomic Sequences and Restriction Site Analysis for Diagnosis of Sickle Cell Anemia" *Science*, 1985, pp. 1350-1354, vol. 230, No. 4732.

Sarma, P. S. et al. "Feline Leukemia and Sarcoma Viruses: Susceptibility of Human Cells to Infection" *Science*, 1970, pp. 1098-1100, vol. 168, No. 3935.

Sodora, D. L. et al. "Identification of Three Feline Immunodeficiency Virus (FIV) env Gene Subtypes and Comparison of the FIV and Human Immunodeficiency Virus Type 1 Evolutionary Patterns" *Journal of Virolog*, 1994, pp. 2230-2238, vol. 68, No. 4.

Talbott, R. L. et al. "Nucleotide Sequence and Genomic Organization of Feline Immunodeficiency Virus" *Proc. Natl. Acad. Sci. USA*, 1989, pp. 5743-5747, vol. 86, No. 15.

Willett, B. J. et al. "Shared Usage of the Chemokine Receptor CXCR4 by the Feline and Human Immunodeficiency Viruses" *Journal of Virology*, 1997, pp. 6407-6415, vol. 71, No. 9.

Willett, B. J. et al. "Common Mechanism of Infection by Lentiviruses" *Nature*, 1997, p. 587, vol. 385, No. 6617.

Yamamoto, J. K. et al. "Feline Immunodeficiency Syndrome—A Comparison Between Feline T-Lymphotropic Lentivirus and Feline Leukemia Virus" *Leukemia*, 1988, p. 204S-215S, vol. 2, No. 12 Supplement.

Yamamoto, J. K. et al. "Pathogenesis of Experimentally Induced Feline Immunodeficiency Virus Infection in Cats" *Am. J. Vet. Res.*, 1998, pp. 1246-1258, vol. 49, No. 8.

Yamamoto, J. K. et al. "Epidemiologic and Clinical Aspects of Feline Immunodeficiency Virus Infection in Cats From the Continental United States and Canada and Possible Mode of Transmission" *J. Am. Vet. Med. Assoc.*, 1989, pp. 213-220, vol. 194, No. 2.

Yamamoto, J. K. et al. "Experimental Vaccine Protection Against Homologous and Heterologous Strains of Feline Immunodeficiency Virus" *Journal of Virology*, 1993, pp. 601-605, vol. 67, No. 1.

Johnston, J. B. et al. "Xenoinfection of Nonhuman Primates by Feline Immunodeficiency Virus" *Current Biology*, 2001, pp. 1109-1113, vol. 11, No. 14.

Abbas, A. K. et al., In *Cellular and Molecular Immunology*, 4th edition, 2000, pp. 196-199, W.B. Saunders Company, Philadelphia.

Nishino, Y et al. "Major Core Proteins, p24s, of Human, Simian, and Feline Immunodeficiency Viruses are Partly Expressed on the Surface of the Virus-Infected Cells" *Vaccine*, 1992, pp. 677-683, vol. 10, No. 10.

Steinman, R. et al. "Biochemical and Immunological Characterization of the Major Structural Proteins of Feline Immunodeficiency Virus" *Journal of General Virology*, 1990, pp. 701-706, vol. 71.

Strandstrom, H.V. et al. "Studies with Canine Sera that Contain Antibodies which Recognize Human Immunodeficiency Virus Structural Proteins" *Cancer Research*, 1990, p. 5628s-5630s, vol. 50.

Elyar, U.S. et al. "Perspectives on FIV vaccine development" *Vaccine*, 1997, 15(12/13):1437-1444.

Uhl, E.W. et al. "FIV vaccine development and its importance to veterinary and human medicine: a review FIV vaccine 2002 update and review" *Veterinary Immunology and Immunopathology*, 2002, 90:113-132.

Desrosiers, R.C., "Prospects for an AIDS vaccine," *Nature Medicine*, Mar. 2004, pp. 221-223, vol. 10, No. 3.

Gallo, R.C., "The end or the beginning of the drive to an HIV-preventive vaccine: a view from over 20 years," *The Lancet*, 2005, pp. 1894-1898, vol. 366.

Girard, M.P. et al., "A review of vaccine research and development: The human immunodeficiency virus (HIV)," *Vaccine*, 2006, pp. 4062-4081, vol. 24.

Walker, B.D. et al., "Toward an AIDS Vaccine," 2008, *Science*, pp. 760-764, vol. 320.

Li, Y. et al. "Complete nucleotide sequence, genome organization, and biological properties of human immunodeficiency virus type 1 in vivo: evidence for limited defectiveness and complementation" *J. Virol.*, 1992, 66(11):6587-6600.

\* cited by examiner

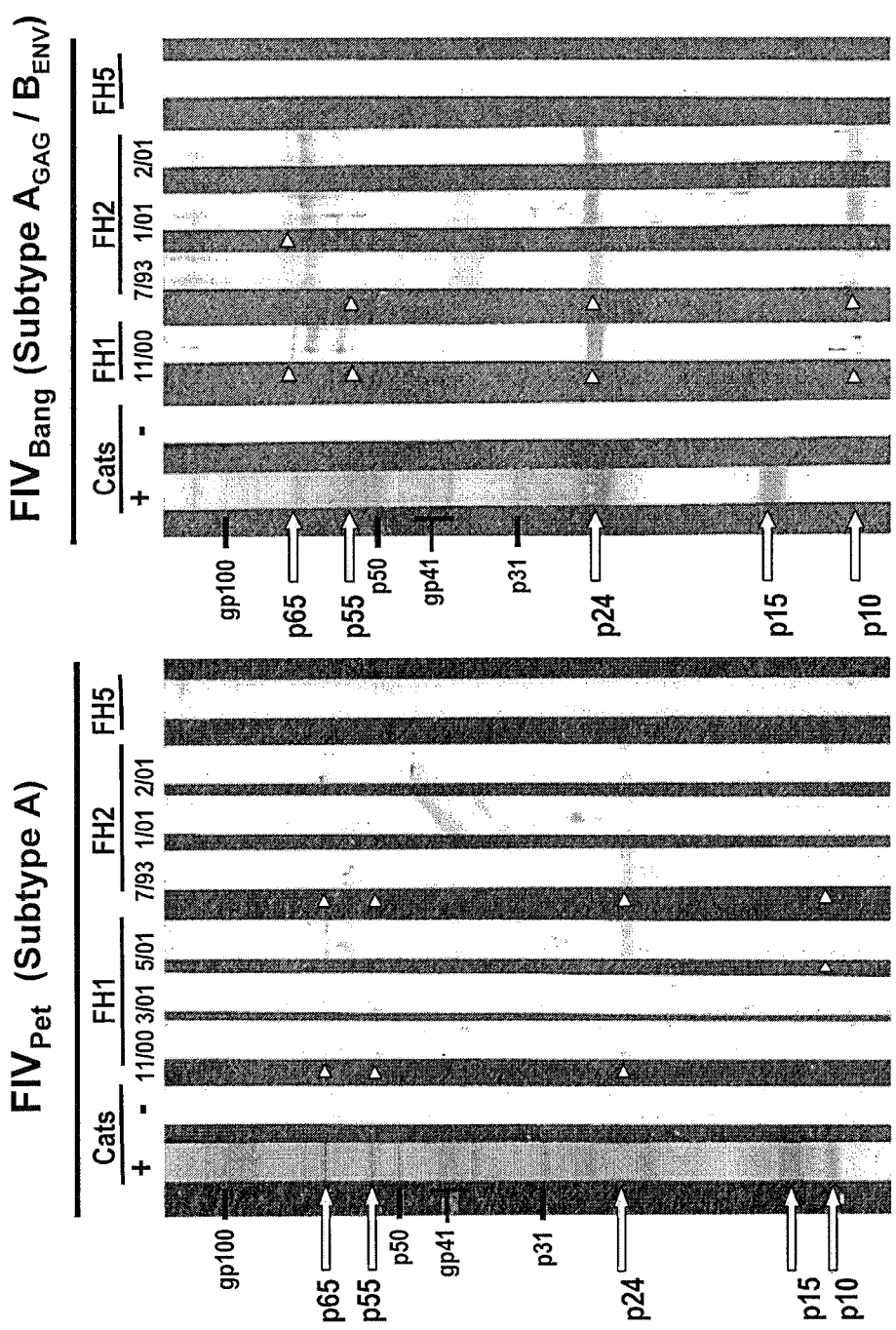

```
FC1concensus  201:EILDETLKQMTAEYDRTHPDGPRPLPYFTAAEIMGLTQEQQAEPRFAPARMQCRAWYLEALGKLAAIKAKSPRAVQLKQGAKEDYSSFIDRLFAQID
FC1 #4             :------------I--D---------------------------------------------------------R--------P---------------
    #5             :------------I--D---------------------------------------------------------R--------P---------------
    #6             :------------I--D---------------------------------------------------------R--------P--*------------
    #10            :---------------------------------------------------------------------------------------------------
    #12            :---------------------------------------------------------------------------------------------------
    #13            :---------------------------------------------------------------------------------------------------
    #14            :-----------------------------------------------------------------N---------------------------------
    #15            :---------------------------------------------------------------------------------------------------
    #16            :---------------------------------------------------------------------------------------------------

FH1 #1             :---------------------------------------------------------------------------------------------------
    #3             :---------------------------------------------------------------------------------------------------
    #10            :---------------------------------------------------------------------------------------------------
    #20            :---------------------------------------------------------------------------------------------------
    #22            :-----------------------------------------R---------------------------------------------------------
    #24            :---------------------------------------------------------------------------------------------------
    #41            :---------------------------------------------------------------------------------------------------
    #42            :---------------------------------------------------------------------------------------------------
    #43            :---------------------------------------------------------------------------------------------------

QEQNTAEVKLYLKQSLSIANANPDCKRAMSHLKPESTLEEKLRACQEVGSPGYKMQLLAEALTRVQTVQTRGSRPTCFNCKKPGHLAKQCREAKRCNNCG 400
------------------------------------------------------------------------------------------------- 399
---------------------------------------------------------------------------------------------------
---------------------------------------------------------------------------------------------------
---------------------------------------------------------------------------------------------------
---------------------------------------------------------------------------------------------------
---------------------------------------------------------------------------------------------------
---------------------------------------------------------------------------------------------------
---------------------------------------------------------------------------------------------------
---------------------------------------------------------------------------------------------------

```
FC1concensus  401:KPGHLAANCWQRGKKTPGNGKMGPAAAPVNQVQQMVPSAPPMEDRKLLDL 450
FC1     #4       :------------------P----------------------------- 
        #5     400:---------------------------------------------- 449
        #6       :-------------------------------------------------
        #10      :-------------------------------------------------
        #12      :-------------------------------------------------
        #13      :-------------------------------------------------
        #14      :-------------------------------------------------
        #15      :-------------------------------------------------
        #16      :-------------------------------------------------
FH1     #1       :-------------------------------------------------
        #3       :-------------------------------------------------
        #10      :-------------------------------------------------
        #20      :---------------------------------G---------------
        #22      :---------------------------------G---------------
        #24      :-------------------------------------------------
        #41      :------------------------A------------------------
        #42      :------------------------A------------------------
        #43      :_____
```

FIG. 2J

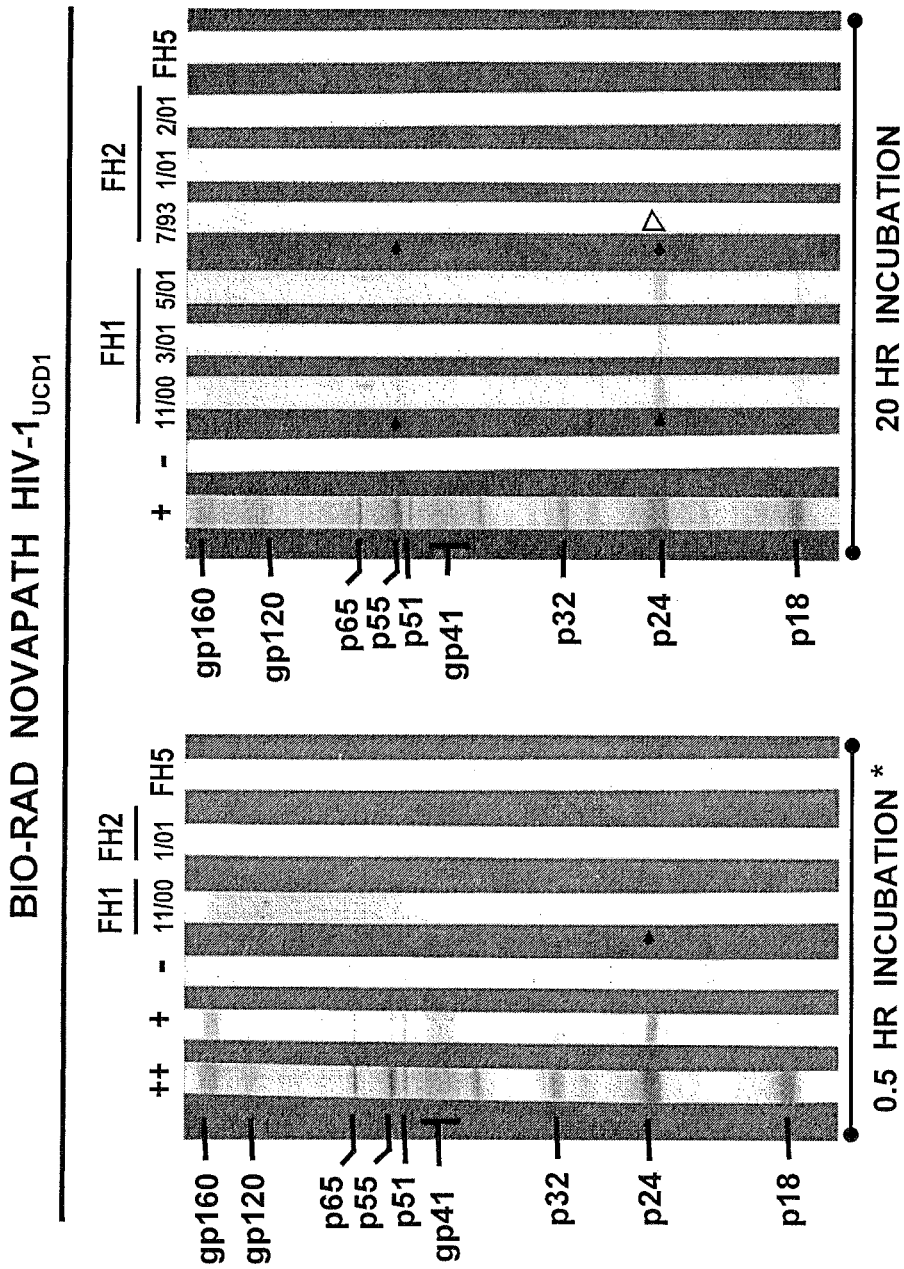

```
         1001:CAGAGAGTACTTTAGAGAGAAAAACTGAGAGCCCTGTCAAGAGGTAGGATCACCAGGATATAAAATGCAGTTGTTAGCAGAAGCTCTTACAAGGGTTCAGAC
FH1      ----------------------------------------------------------------------------------------------------
FC1      ----------------------------------------------------------------------------------------------------
PETALUMA ----A-----CC----A-----GT------T-------AA----C----------------------------------------AC-C--G-------AA-----AGT
UK8      ----A--T-CC----A-----GT------T-------------A--------------C-----------------------------AC-C--G-------AA-----AGT
PPR      ----A-----CC----A-----GT------T-------------A--------------C-----------------------------AC-C--G-------AA-----AGT
SENDAI-1 ----A-----CC----A-----GT------T-----------A---------------------------------------------------------AA-------
BANGSTON ----A-----CC----A-----GT------T-------------A--------------C-----------------------------AC-C--G-------AA-----AGT
AOMORI-1 ----A------------------------------G---------A----------------------------------------------------------------
AOMORI-2 ----A------------------------------G---------A----------------------------------------------------------------
SENDAI-2 ----A------------------------------G---------A----------------------------------------------------------------
TM2      ----A------------------------------G---------A------------------------------------A--C-G--G-----------------A--
YOKOHAMA ----A------------------------------G---------A----------------------------------------------------------------
SHIZUOKA ----A-----CC----A-----GT------T-----------AA--------------T----G---------------------------AC-T--G-------AA-----A--
FUKUOKA  ----A-----CC----A--G--GT------T-----------AA---------------------------------------------------------------

AGTTCAAACAAGAGGAT

```
         1201:AAACCTGGTCACTTAGCTGCTAATTGCTGGCAAAGAGTAAAAAACCCCGGGAAACGGGAAGATGGGCCAGCTGCAGCCCCGTAAACCAAGTGCAGC
FH1
FC1            ---------------------------------------------------------------------------------------------
PETALUMA       ---------TG--------C------T------G--AA--G---G-ATT---------T------GC-----G-----------A--G--T--A--
UK8            -G-------T--------C-GA-----GG-T-----------G-A-T----------T------GC-----G-----------A---------
PPR            ---------T--------C--A--T------G-T--------G--ATT---------T------GC-----G-----------A--G--T-----
SENDAI-1       ---------------------------------------------------------------------------------------------
BANGSTON       --G------T--------C--A--T------G-T--------G-ATT-----------------GC-----G-----------A--G--T-----
AOMORI-1       ---------------------------------------------------------------------------------------------
AOMORI-2       ---------------------------------------------------------------------------------------------
SENDAI-2       ---------------------------------------------------------------------------------------------
TM2            ------------------------------G--------GG-------T--------A---G---------G-----------A---------
YOKOHAMA       ---------------------------------------------------------------------------------------------
SHIZUOKA       -G-------C-T--G----C--A--T------G--A-C-G---TG-TT-----------------------G-----------A---------
FUKUOKA        ---------------------------------------------------------------------------------------------

AAATGGT***GCCATCTGCACCTCCAATGGAAGACAGGAAATTGTTAGATTTATAA 1353
                ***                                                 
--GCA--AAT---------------------G--G-AACT----GATTTA-A-
-GGCA--AAT---------------------G--G--ACT----GATTTA-A-
---CA--AAT---------------------G--A-AATT----GATTTA-A-A

--GCA--AATA--------------T----A--G--G-AACT----GATTTA-A-

----A--***A----------------------G--G-AACT---AGATTTA-A-

--GCA--***----------T------G------G--A-TTG--AGATTTA-A-
```

FIG. 4G

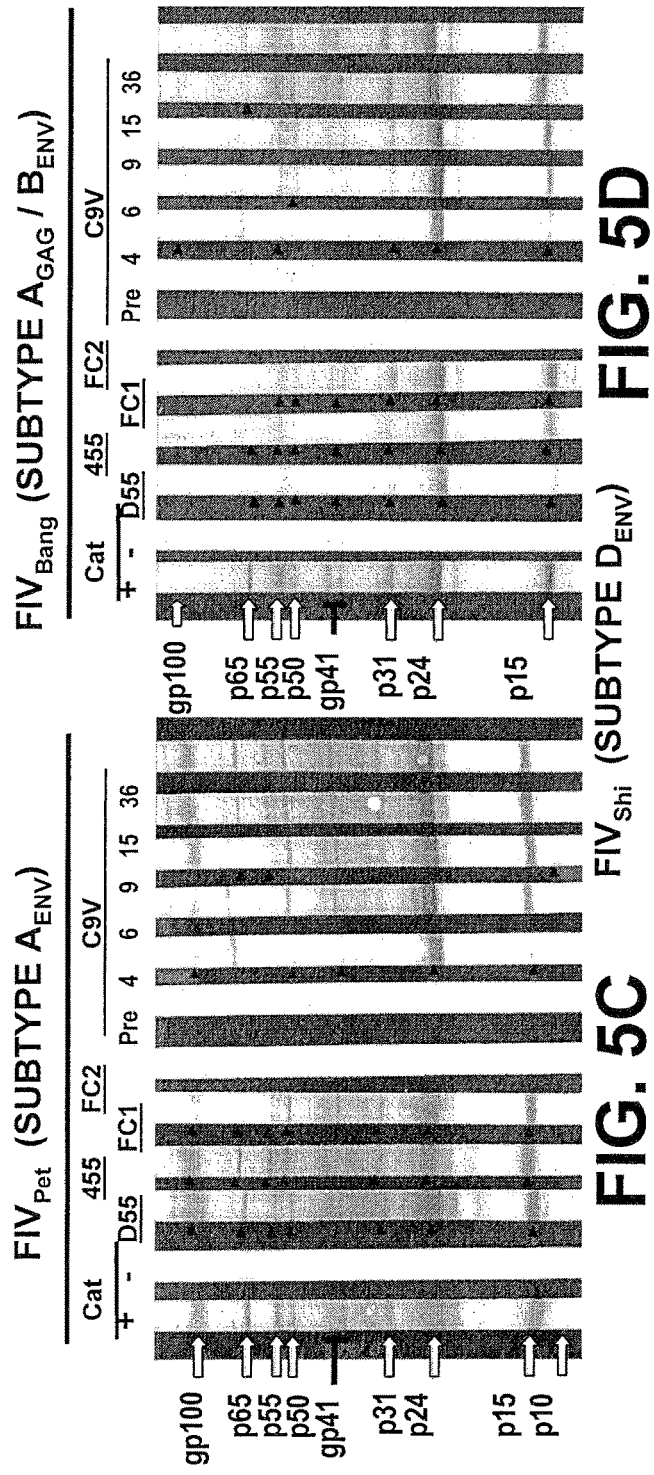
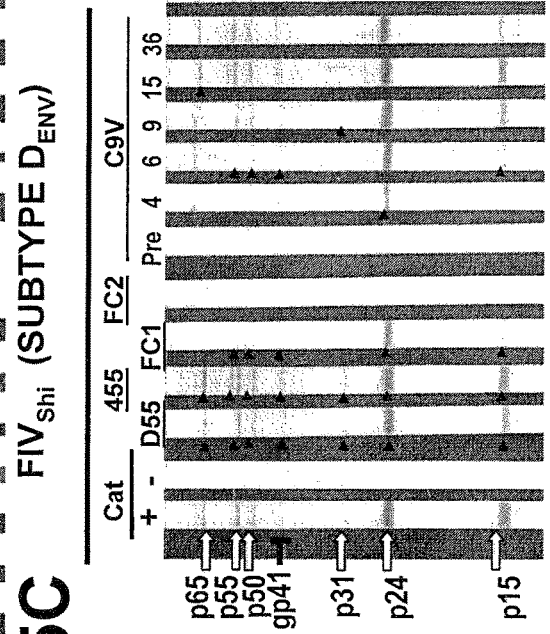
FIG. 5C
FIG. 5D
FIG. 5E

```
Consensus    --C-GC-GCTGAA-A-ATGTA--CTCA-ATGGGATTAGA-AC-AG-CCATCT---A--GA-----GG-GGAAA-G---G 385
Pet gag      TGCTGCAGCTGAAATATGTATTCTCAAATGGGATTAGACACTAGGCCATCTATGAAAGAAGCAGGTGGAAAAGAGG 385
Bang         TGCTGCAGCTGAAAACATGTATACTCAGATGGGATTAGACACCAGGCCATCTACAAGAGAAGCAGGAGGAAAGAGG 385
JSY3 gag 0   TGCTGCAGCTGAAAATATGTACACTCAGATGGGATTAGACACTAGACCATCTATGAGAGAAGCAGGAGGAAAGAGG 385
UK8 gag      TGCTGCAGCTGAAAATATGTATATCAGATGGGATTAGACACTAGACCATCTACAAAGGAAGCTGGAGGAAAAGAGG 385
Shizuoka     TACTGCCGCTGAAAATATGTATGCTCAGATGGGATTAGATACTAGACCATCTTTAAAGGAGGCAGGAGGAAAGGTAG 133
Aomori 1     CACAGCAGCTGAAAATATGTATGCTCAGATGGGATTAGACACCAGACCATCTATAAAAGAAAGTGGGGAAAAGAAG 133
TM2 gag      CACAGCAGCTGAAAATATGTATGCTCAGATGGGATTAGACACCAGACCATCTGTAAAAGAAAGTGGGGAAAAGAAG 385
RT Forward   -------------------------------------------------------------------------- 0
RT Probe     -------------------------------------------------------------------------- 0
RT Reverse   -------------------------------------------------------------------------- 0
FC1 GAG      CGCAGCAGCTGAACACATGTATGCTCAGATGGGATTAGATACCAGACCATCTATAAAAGAAAGTGGGGAAAAGAAG 385
A9=4         -------------------------------------------------------------------------- 0
B4=5         -------------------------------------------------------------------------- 0

Consensus    A--G---CCTCCACAGGC-T-TCCTAT-CAAACA--AAATGGAG-ACCA-A--A-GTAGC-CT-GA-CC-AAAATGGT 462
Pet gag      AAGGC-CCTCCACAGGCCATATCCTATTCCTATTCAAACAGTAACAGTAAATGGAGTACCACACAATATGTAGCACTTGACCACTTGACCACTTGACCCAAAAATGGT 461
Bang         AAAGC-CCTCCACAGGCCATATCCTATTCCTATTCAAACAGTAACAGTAAATGGAGTACCACACAATATGTAGCACTTGACCACTTGACCACTTGACCCAAAAATGGT 461
JSY3 gag 0   AAAGC-CCTCCACAGGCCATATCTCCTATTCAAACAGCAAATGGAGCACCACAATATGGAGCACCACACAATATGTAGCACTTGACCACTTGACCACTTGACCCAAAAATGGT 461
UK8 gag      AAGGC-CCTCCACAGGCCATATCCTATTCAAACAGCAAATGGAGCACCACAATATGGAGCACCACAATATGTAGCTCTTGACCCTGACCCAAAAATGGT 461
Shizuoka     A-GGAGCCTCCACAGGCCATATCCTATCCAAACAGTAAATGGAGCACCACACAATATGTAGCCCTGGATCCTAAAATGGT 209
Aomori 1     AAGGA-CCTCCACAGGCTTATCCTATTCAAACAGTAAATGGAGCACCACAGTATGGAGCCCTTGATCCAAAAATGGT 209
TM2 gag      AAGGA-CCTCCACAGGCTTATCCTATTCAAACAGTAAATGGAGCACCACAGTATGGAGCCCTTGATCCAAAAATGGT 461
RT Forward   ---AGC-CCTCCACAGGCATCTC------------------------------------------------------ 19
RT Probe     --------------------------ATTCAAACAGCAAATGGAGCACCACAATATG-------------------- 31
RT Reverse   --------------------------------------------------------TTGACCCAAAAATGGT 16
FC1 GAG      AAGGA-CCTCCACAGGCTTATCCTATTCAAACAGTAAATGGAGCACCAGTGTAGCCCTTGACCACTTGACCACTTGACCCAAAAATGGT 461
A9=4         -TAGC-CCTCCACAGGCATATCCTATTCAAACAGTAAATGGAGTACCATAACACGTAGCACTTGACCCTGACCACTTGACCCAAAAATGGT 75
B4=5         --AGC-CCTCCACAGGCATATCCTATTCAAACAGTAAATGGAGTACCACACAATATGTAGCGCTTGACCCTTGACCCAAAAATGGT 74
```

IMMUNOGENIC COMPOSITIONS COMPRISING FIV AND HIV GAG ANTIGENS

CROSS-REFERENCE TO RELATED APPLICATIONS

This application is a continuation of U.S. application Ser. No. 13/476,835, filed May 21, 2012, which is a continuation of U.S. application Ser. No. 12/407,730, filed Mar. 19, 2009, now U.S. Pat. No. 8,182,820, which is a continuation of U.S. application Ser. No. 10/080,772, filed Feb. 22, 2002, now abandoned, which claims the benefit of U.S. Provisional Application Ser. No. 60/270,745, filed Feb. 22, 2001.

GOVERNMENT SUPPORT

This invention was made with government support under Grant No. NIH R01-AI30904-9 awarded by National Institutes of Health. The government has certain rights in the invention.

The Sequence Listing for this application is labeled "2DF6559.TXT" which was created on Oct. 10, 2014 and is 144 KB. The entire contents of the Sequence Listing is incorporated herein by reference in its entirety.

BACKGROUND OF THE INVENTION

Domestic cats are subject to infection by several retroviruses, including feline leukemia virus (FeLV), feline sarcoma virus (FeSV), endogenous type C oncoronavirus (RD-114), and feline syncytia-forming virus (FeSFV). Of these, FeLV is the most significant pathogen, causing diverse symptoms including lymphoreticular and myeloid neoplasms, anemias, immune-mediated disorders, and an immunodeficiency syndrome that is similar to human acquired immune deficiency syndrome (AIDS). Recently, a particular replication-defective FeLV mutant, designated FeLV-AIDS, has been more particularly associated with immunosuppressive properties.

The discovery of feline T-lymphotropic lentivirus (now designated as feline immunodeficiency virus, FIV) was first reported in Pedersen et al. (1987). Characteristics of FIV have been reported in Yamamoto et al. (1988a); Yamamoto et al. (1988b); and Ackley et al. (1990). Seroepidemiologic data have shown that infection by FIV is indigenous to domestic and wild felines throughout the world. A wide variety of symptoms are associated with infection by FIV, including abortion, alopecia, anemia, conjunctivitis, chronic rhinitis, enteritis, gingivitis, hematochezia, neurologic abnormalities, periodontitis, and seborrheic dermatitis. The immunologic hallmark of domestic cats infected with FIV is a chronic and progressive depletion of feline $CD4^+$ peripheral blood lymphocytes, a reduction in the CD4:CD8 cell ratio and, in some cases, an increase in CD8-bearing lymphocytes. Based on molecular, biochemical and immunopathologic characteristics, FIV infection of cats is now considered to be a better feline AIDS model than FeLV-FAIDS.

Cloning and sequence analysis of FIV has been reported in Olmsted et al. (1989a); Olmsted et al. (1989b); and Talbott et al. (1989). Hosie and Jarret (1990) described the serological response of cats infected with FIV. FIV virus subtypes can be classified according to immunotype based on the level of cross-neutralizing antibodies elicited by each strain (Murphy and Kingsbury, 1990). Recently, viruses have been classified into subtypes according to genotype based on nucleotide sequence homology. Although HIV and FIV subtyping is based on genotype (Sodora et al., 1994; Rigby et al., 1993; and Louwagie et al., 1993), little is known about the correlation between the genotype and immunotype of subtypes. FIV viral isolates are currently classified into four FIV subtypes: A, B, C and D. (Kakinuma et al., 1995). The following abbreviations of FIV strains are used herein:

| Strain (subtype) | Abbreviation |
|---|---|
| Petaluma (A) | $FIV_{Pet}$ |
| Dixon (A) | $FIV_{Dix}$ |
| UK8 (A) | $FIV_{UK8}$ |
| Bangston (B) | $FIV_{Bang}$ |
| Aomori-1 (B) | $FIV_{Aom1}$ |
| Aomori-2 (B) | $FIV_{Aom2}$ |
| Shizuoka (D) | $FIV_{Shi}$ |

Infectious isolates and infectious molecular clones have been described for all FIV subtypes except for subtype C (Sodora et al., 1994). Subtype C FIV has only been identified from cellular DNA of cats from Canada (Sodora et al., 1994; Rigby et al., 1993; Kakinuma et al., 1995).

To date, there have been no reported cases of retroviral zoonosis between domestic cats and humans (Pedersen et al., 1987; Yamamoto et al., 1989; Yamamoto et al., 1988; Butera et al., 2000; CDC Report: HIV and Retrovirology). No cases of feline leukemia virus (FeLV), feline foamy virus (FeFV), and feline immunodeficiency virus (FIV) infections of humans have been reported, even in populations at high risk for viral exposure, such as veterinarians, animal caretakers, and scientists from feline retroviral laboratories (Yamamoto et al., 1989; Yamamoto et al., 1988; Butera et al., 2000). Human patients with leukemia and chronic fatigue syndrome selected for their disease association also tested negative for FeLV (Butera et al., 2000). However, many of the assays used in these studies were based on less sensitive antigen and antibody tests (Butera et al., 2000). In few of these studies, a more sensitive FeLV PCR (polymerase chain reaction) system for proviral DNA and a sensitive Western blot analysis for FIV antibodies were performed but their findings also supported previous reports of the lack of feline retroviral zoonosis (Yamamoto et al., 1988; Butera et al., 2000). In vitro studies have shown that all three of these feline retroviruses are capable of infecting primary human cells and human cell (Butera et al., 2000; Sarma et al., 1970; Azocar et al., 1979; Jarrett et al., 1973). Recent studies have also demonstrated that FIV infects human cells in vitro via the CXCR4 receptor, which has been shown to be a coreceptor for HIV-1 (Willett et al., 1997a; Willett et al., 1997b; Poeschla et al., 1998; Richardson et al., 1999; Johnston et al., 1999b). It has been reported that FIV vector sequences which included FIV rev-RRE and gag are more efficient in infecting human cells than those without FIV gag (Johnston et al., 1999).

Zoonotic infection of humans with SIV has been limited to individuals working with SIV or SIV-infected laboratory animals (Khabbaz et al., 1994; Khabbaz et al., 1992). All of the SIV-infected individuals are clinically asymptomatic with one having transient infection while the other showed persistent infection.

Disclosed herein is the surprising discovery of zoonotic retroviral infection of humans in vivo with FIV. It has also been discovered that zoonotic FIV infection can complicate the current HIV-1 antibody diagnostic tests that are used commercially to screen persons for infection with HIV.

BRIEF SUMMARY OF THE INVENTION

The subject invention concerns materials and methods for detecting, preventing and treating retroviral infections in humans and other non-feline animals susceptible to infection by retrovirus. It has been discovered that FIV can be transmitted from cats to humans and that the FIV can infect human cells in vivo. Persons infected with FIV produce an immune response against the virus, including the production of antibodies to FIV. It has also been discovered that antibodies generated by a person infected with FIV cross-react with HIV antigens. Thus, the methods and compositions of the subject invention can be used to detect, prevent and treat FIV infection in humans and other non-feline animals that are susceptible to FIV infection. The present invention includes materials and methods for diagnosing whether a person is infected with FIV or HIV. The methods and compositions of the invention can also be used to prevent and treat infection by HIV in humans.

BRIEF DESCRIPTION OF THE DRAWINGS

FIGS. 1A-1D show FIV Western blot analysis of subjects #FH1 and #FH2. $FIV_{Shi}$ (D) and $FIV_{Bang}$ (B) Western blots (FIGS. 1A-1C) were reacted with sera from subjects #FH1, #FH2, and #FH5 (control individual with minimum cat exposure) for 20 hours. Experimentally FIV-infected cat (Cat+) was used as the source of strongly reactive control serum and uninfected SPF cat (Cat−) was used as the source of non-reactive control serum. Key bands are highlighted with an arrowhead on the left. FIG. 1D: Virus neutralizing antibodies to FIV and HIV were detected in cultures. a Western blot of human sera on $FIV_{Shi}$.

Figure 2A:
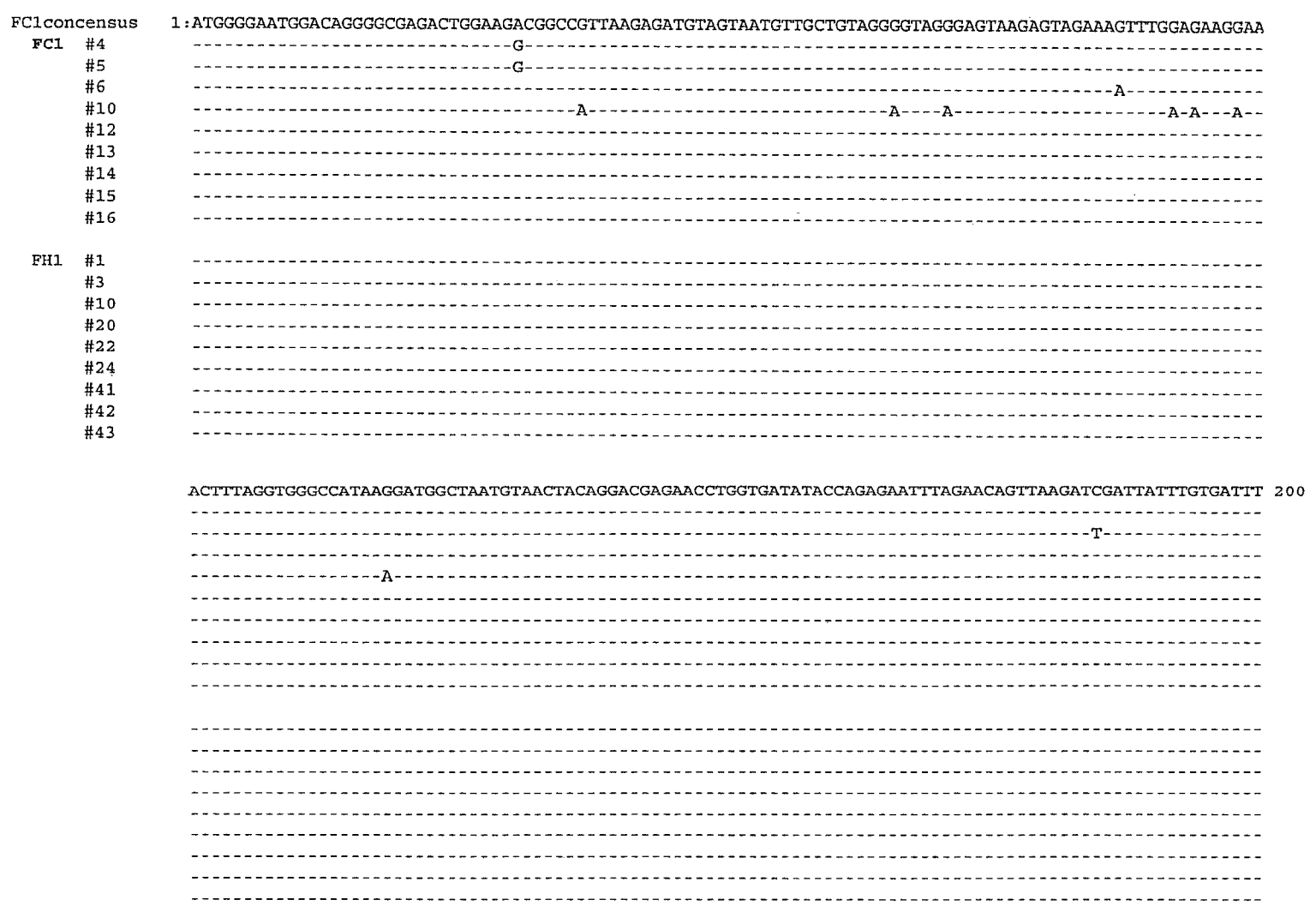
Figure 2B:
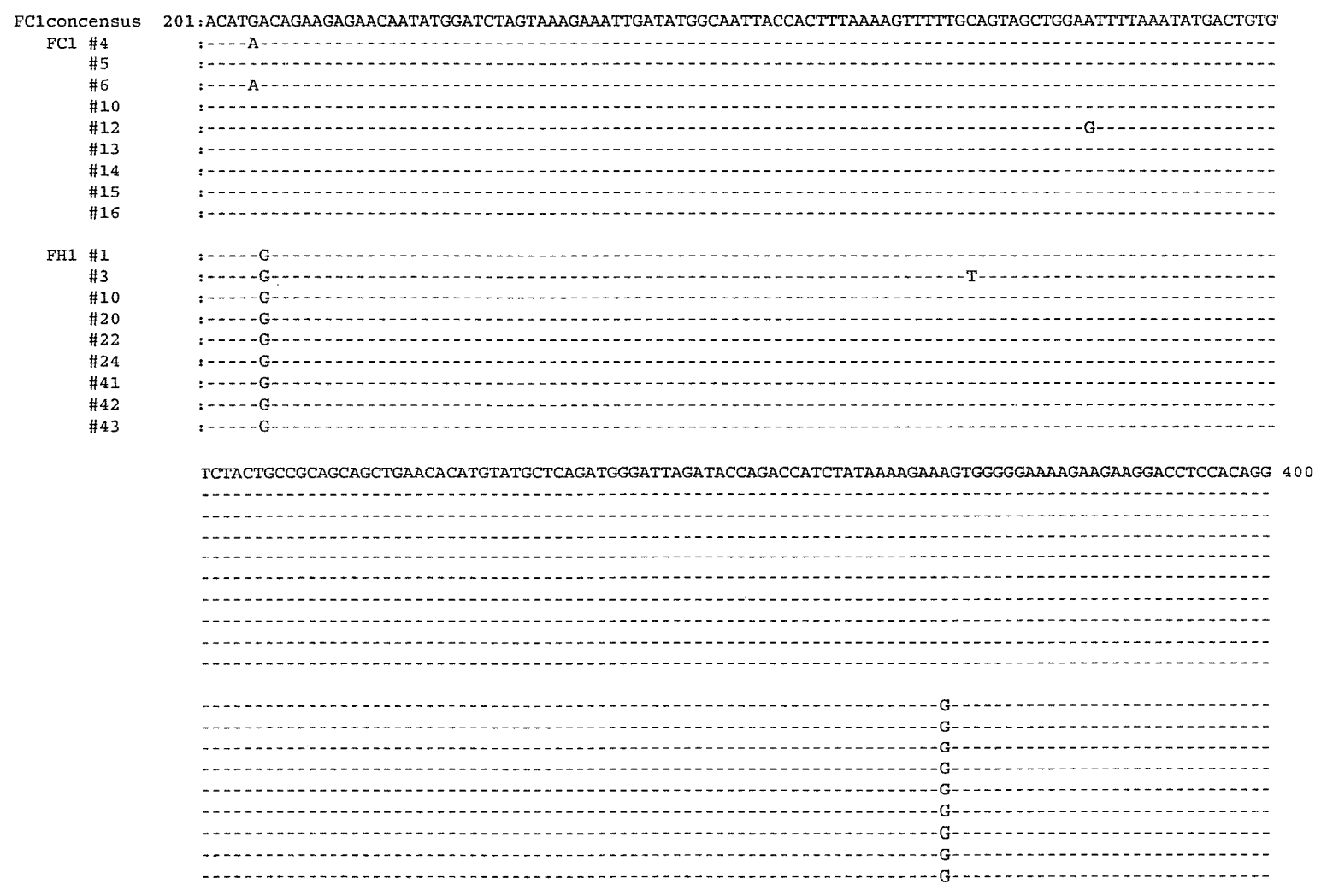
Figure 2C:
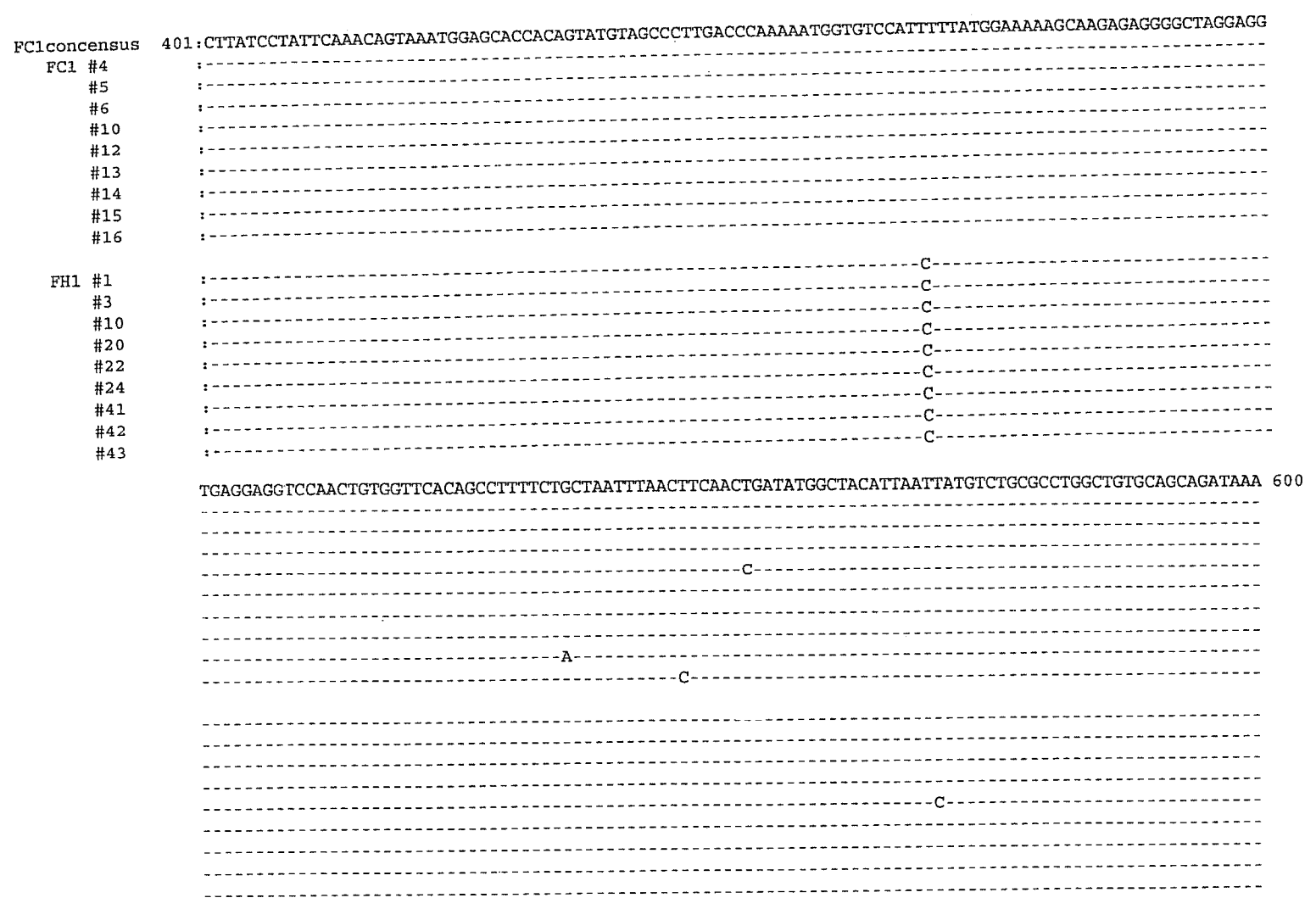
Figure 2D:
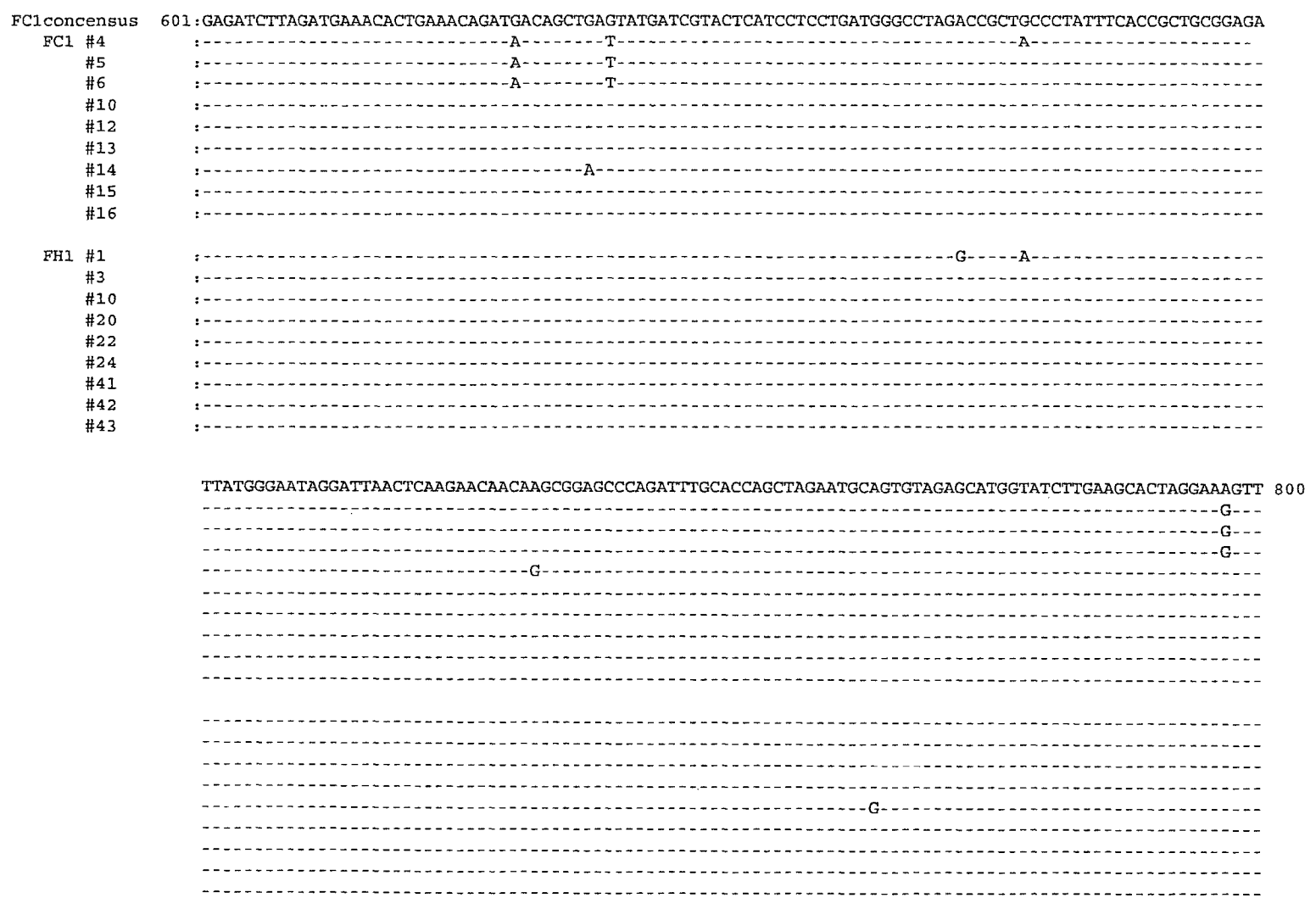
Figure 2E:
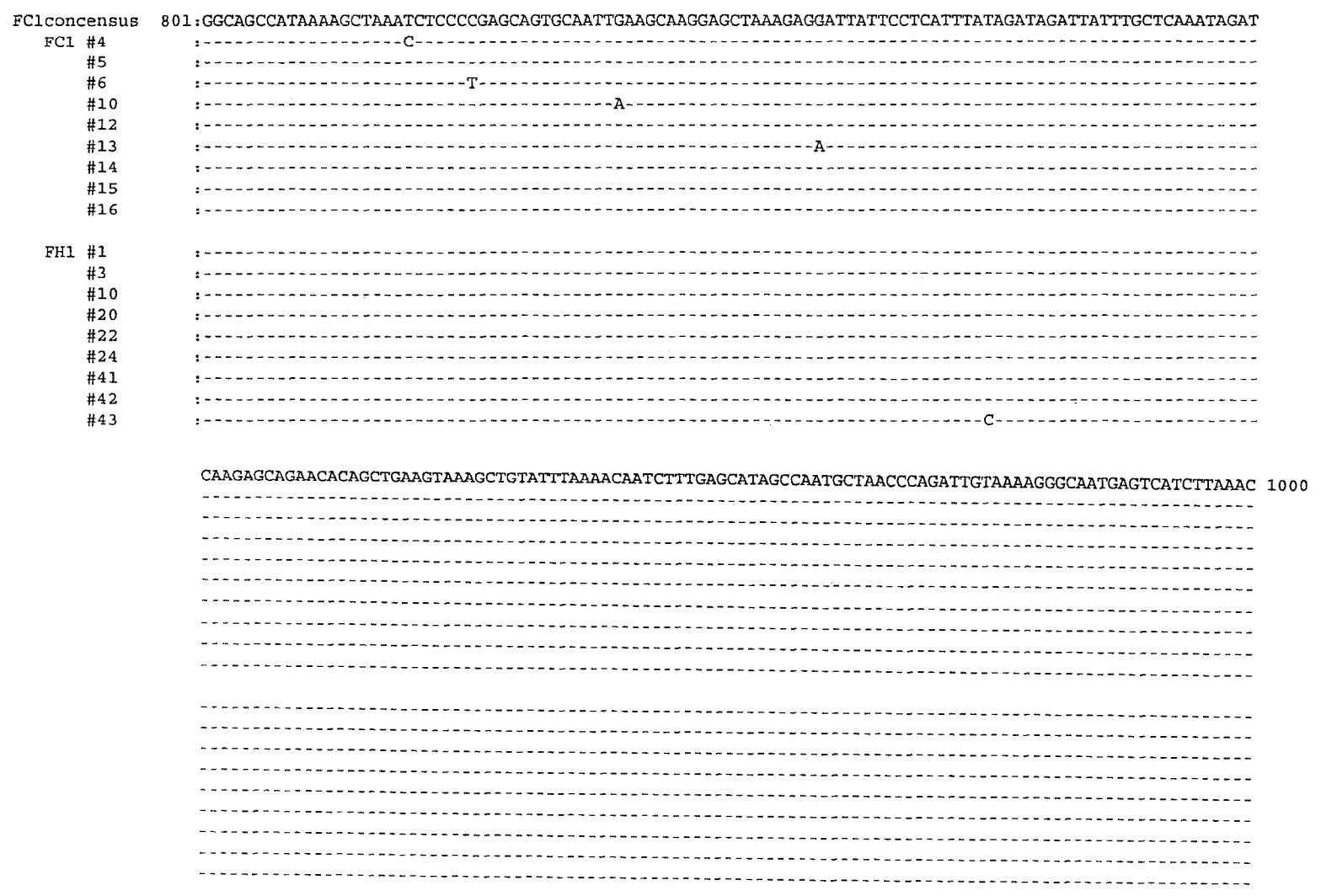
Figure 2F:
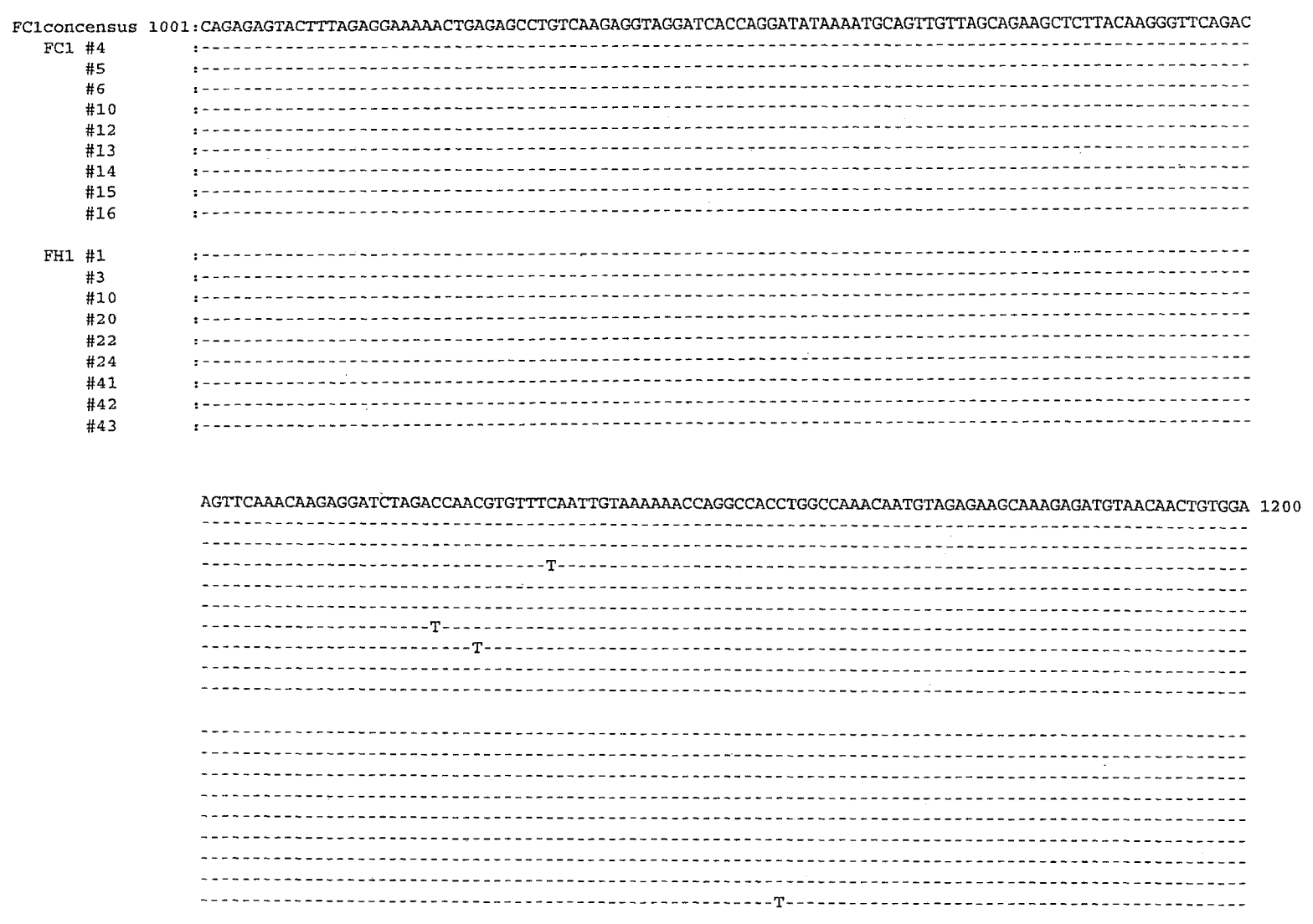
Figure 2G:
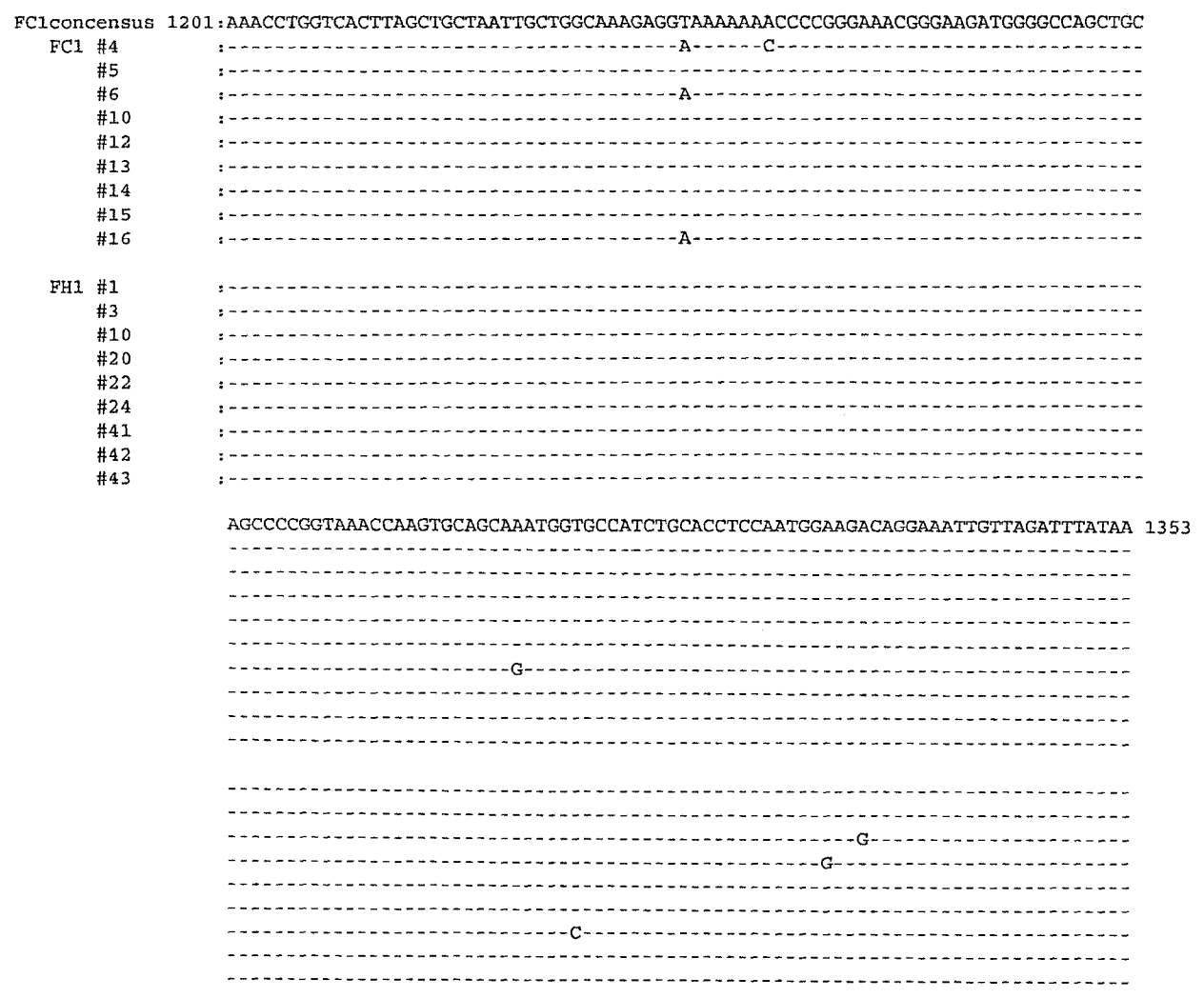
Figure 2H:
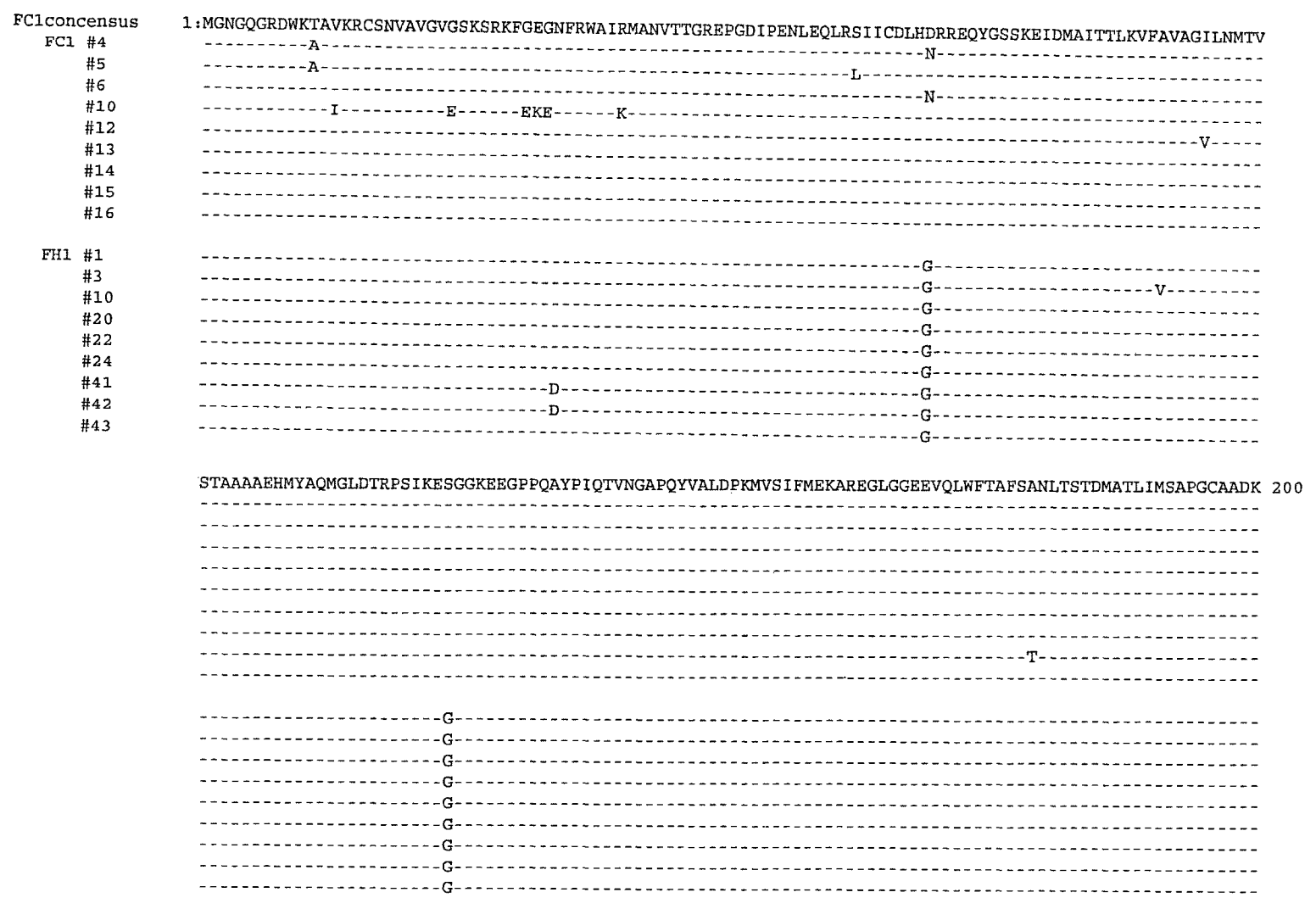

FIGS. 2A-2J show alignment of gag sequences of cat #FC1 and subject #FH1. FIGS. 2A-2G show alignment of gag nucleotide sequences. FIGS. 2H-2J show alignment of gag amino acid sequences. Gag sequences of the nine clones isolated from cat #FC1 and subject #FH1 are shown in comparison to the consensus sequence of cat #FC1 (top sequence). Hyphens denote nucleotide or amino acids identical to the consensus sequence derived from cat #FC1 and those, which differ from the consensus, are presented with the appropriate nucleotide or amino acid symbols. In FIGS. 2A-2G the nucleotide consensus sequence is SEQ ID NO: 3; FC1 #4 is SEQ ID NO: 4; FC1 #5 is SEQ ID NO: 5; FC1 #6 is SEQ ID NO: 6; FC1 #10 is SEQ ID NO: 7; FC1 #12 is SEQ ID NO: 8; FC1 #13 is SEQ ID NO: 9; FC1 #14 is SEQ ID NO: 10; FC1 #15 is SEQ ID NO: 11; FC1 #16 is SEQ ID NO: 12; FH1 #1 is SEQ ID NO: 13; FH1 #3 is SEQ ID NO: 14; FH1 #10 is SEQ ID NO: 15; FH1 #20 is SEQ ID NO: 16; FH1 #22 is SEQ ID NO: 17; FH1 #24 is SEQ ID NO: 18; FH1 #41 is SEQ ID NO: 19; FH1 #42 is SEQ ID NO: 20; and FH1 #43 is SEQ ID NO: 21. In FIGS. 2H-2J the amino acid consensus sequence is SEQ ID NO: 22; FC1 #4 is SEQ ID NO: 23; FC1 #5 is SEQ ID NO: 24; FC1 #6 is SEQ ID NO: 25; FC1 #10 is SEQ ID NO: 26; FC1 #12 is SEQ ID NO: 27; FC1 #13 is SEQ ID NO: 28; FC1 #14 is SEQ ID NO: 29; FC1 #15 is SEQ ID NO: 30; FC1 #16 is SEQ ID NO: 31; FH1 #1 is SEQ ID NO: 32; FH1 #3 is SEQ ID NO: 33; FH1 #10 is SEQ ID NO: 34; FH1 #20 is SEQ ID NO: 35; FH1 #22 is SEQ ID NO: 36; FH1 #24 is SEQ ID NO: 37; FH1 #41 is SEQ ID NO: 38; FH1 #42 is SEQ ID NO: 39; FH1 #43 is SEQ ID NO: 40.

FIGS. 3A-3C show HIV-1 Western blot analysis of subjects #FH1 and #FH2. Strongly reactive (++), weakly reactive (+), and non-reactive (−) control human sera from the Bio-Rad Novapath HIV-1 Immunoblot Kit and Cambridge Biotech HIV-1 Western Blot Kit were used as controls for respective HIV-1 Western blot strips. Serum from subject #FH5 with minimal exposure to cats, was used as additional negative control for Western blots from both companies. The durations of serum incubation are shown and FDA-approved recommended incubation periods are also designated with asterisk. Key bands are highlighted with an arrowhead on the left.

Figure 4A:
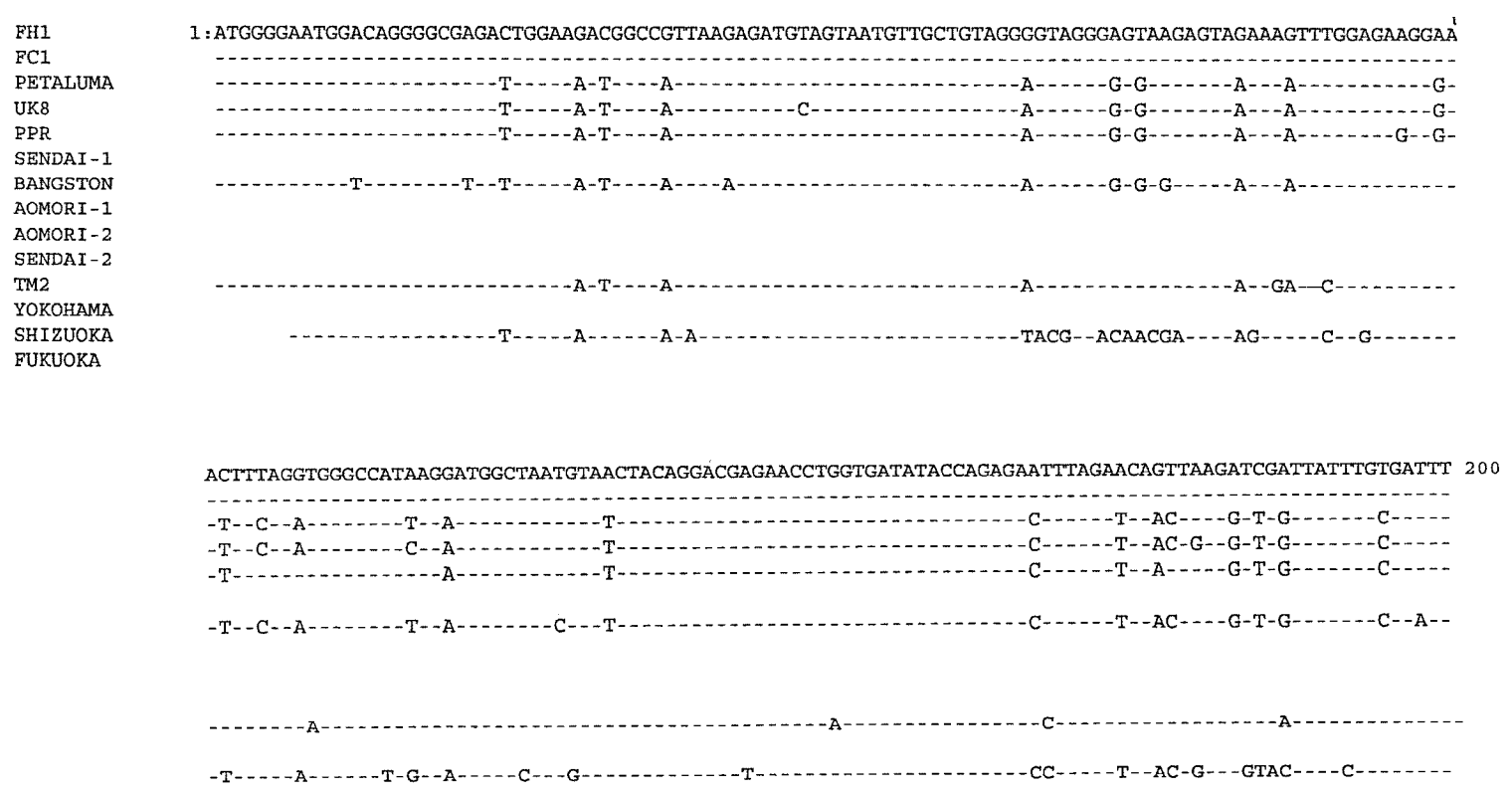
Figure 4B:
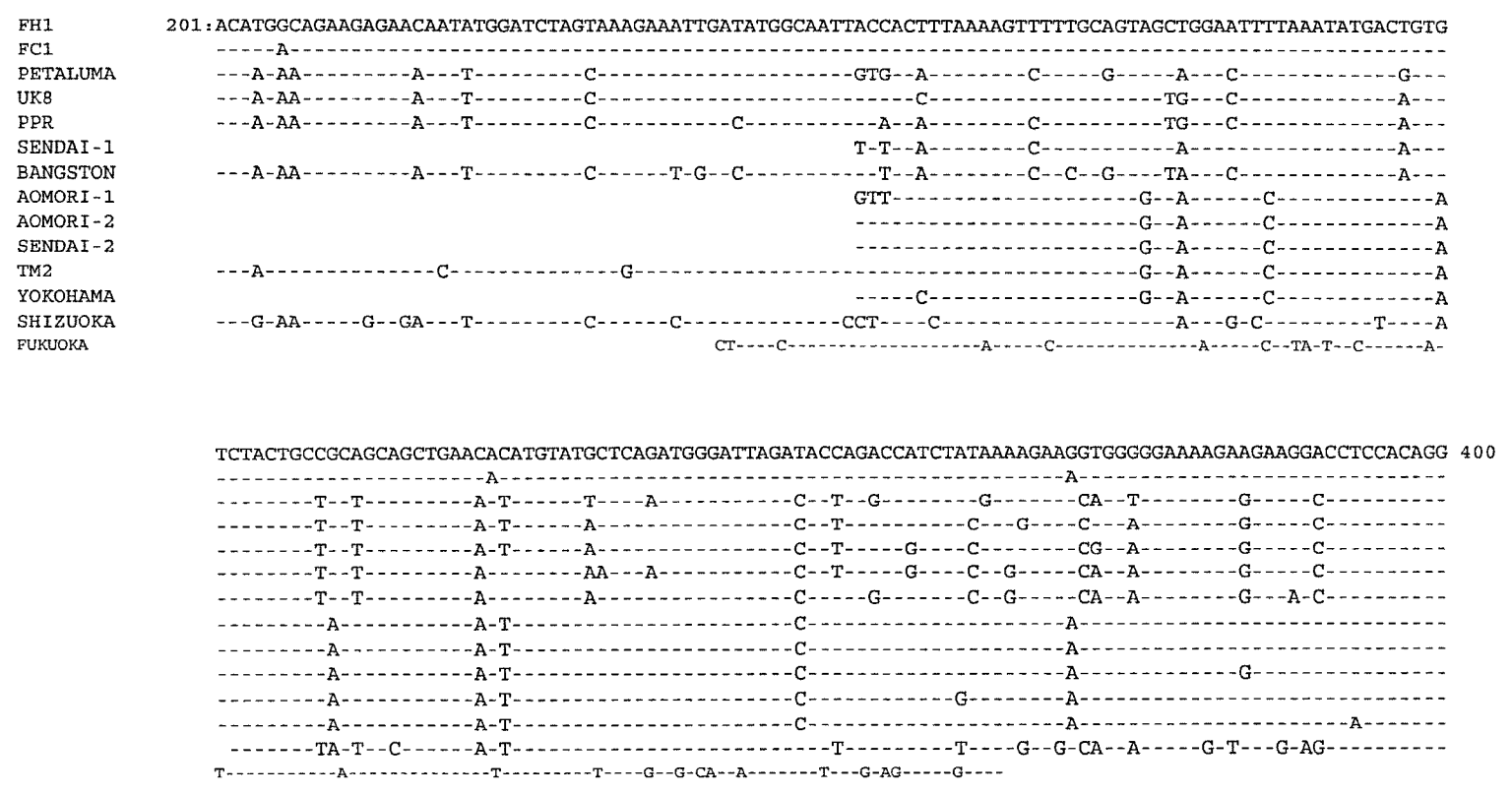
Figure 4C:
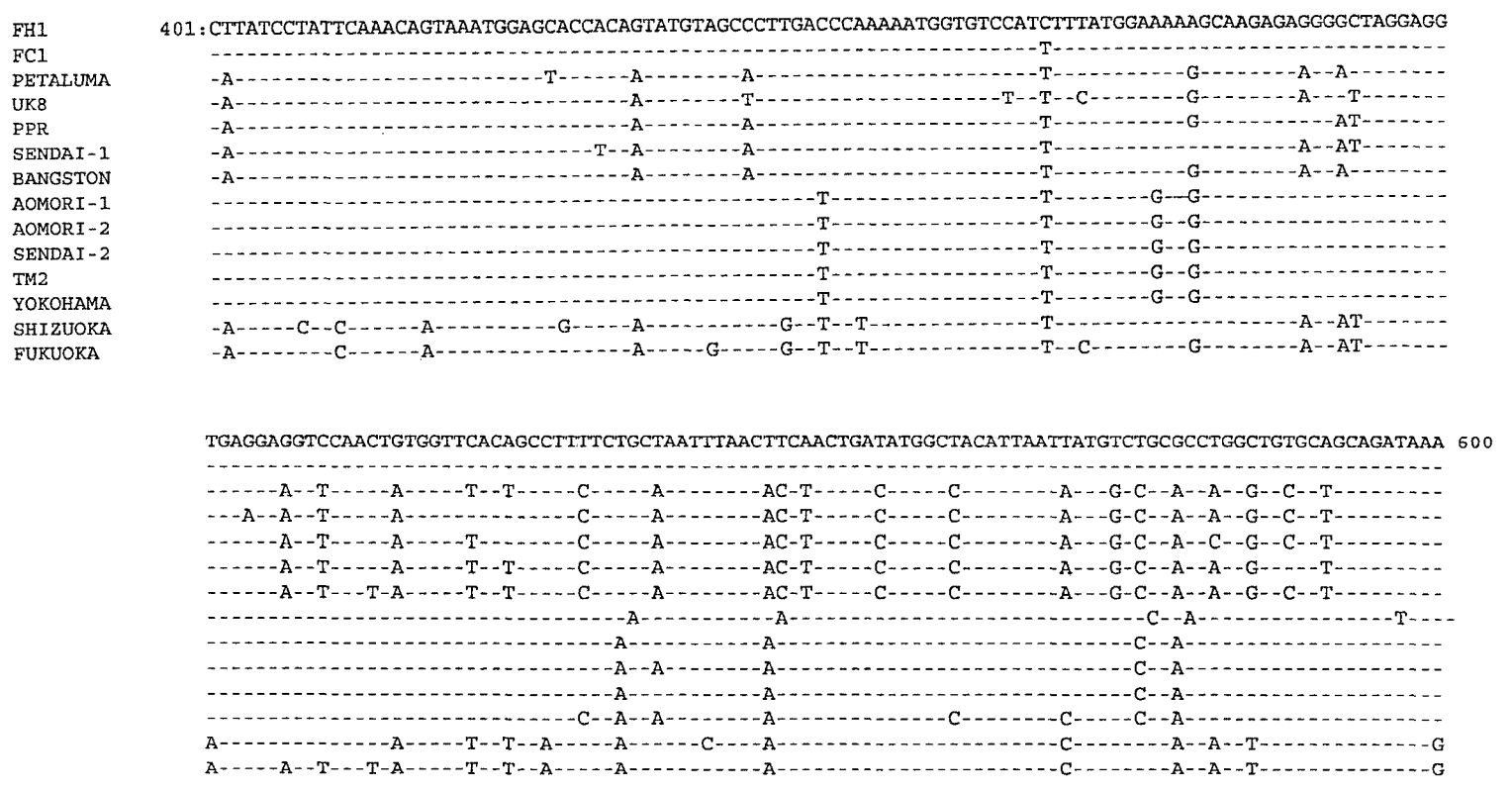
Figure 4D:
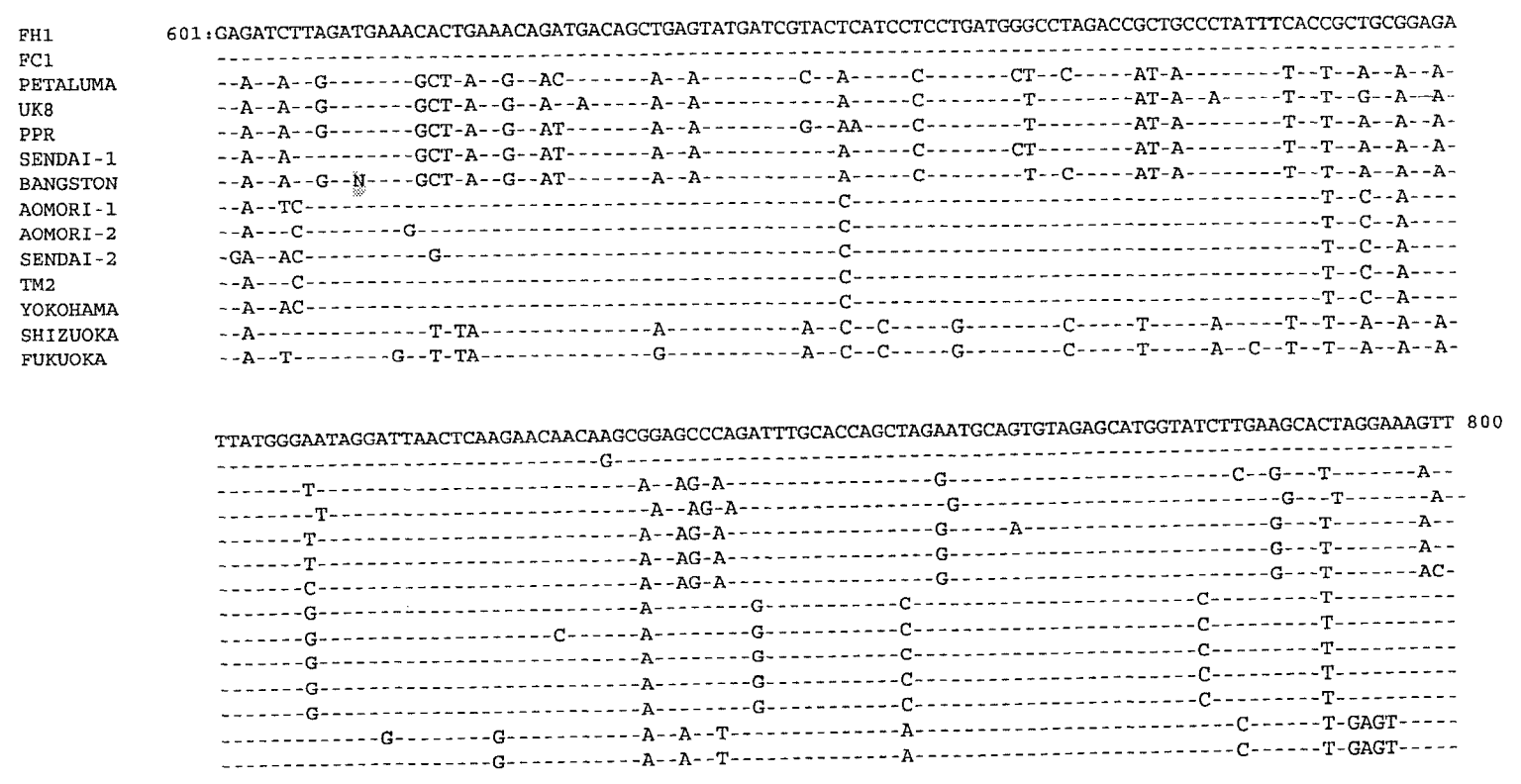
Figure 4E:
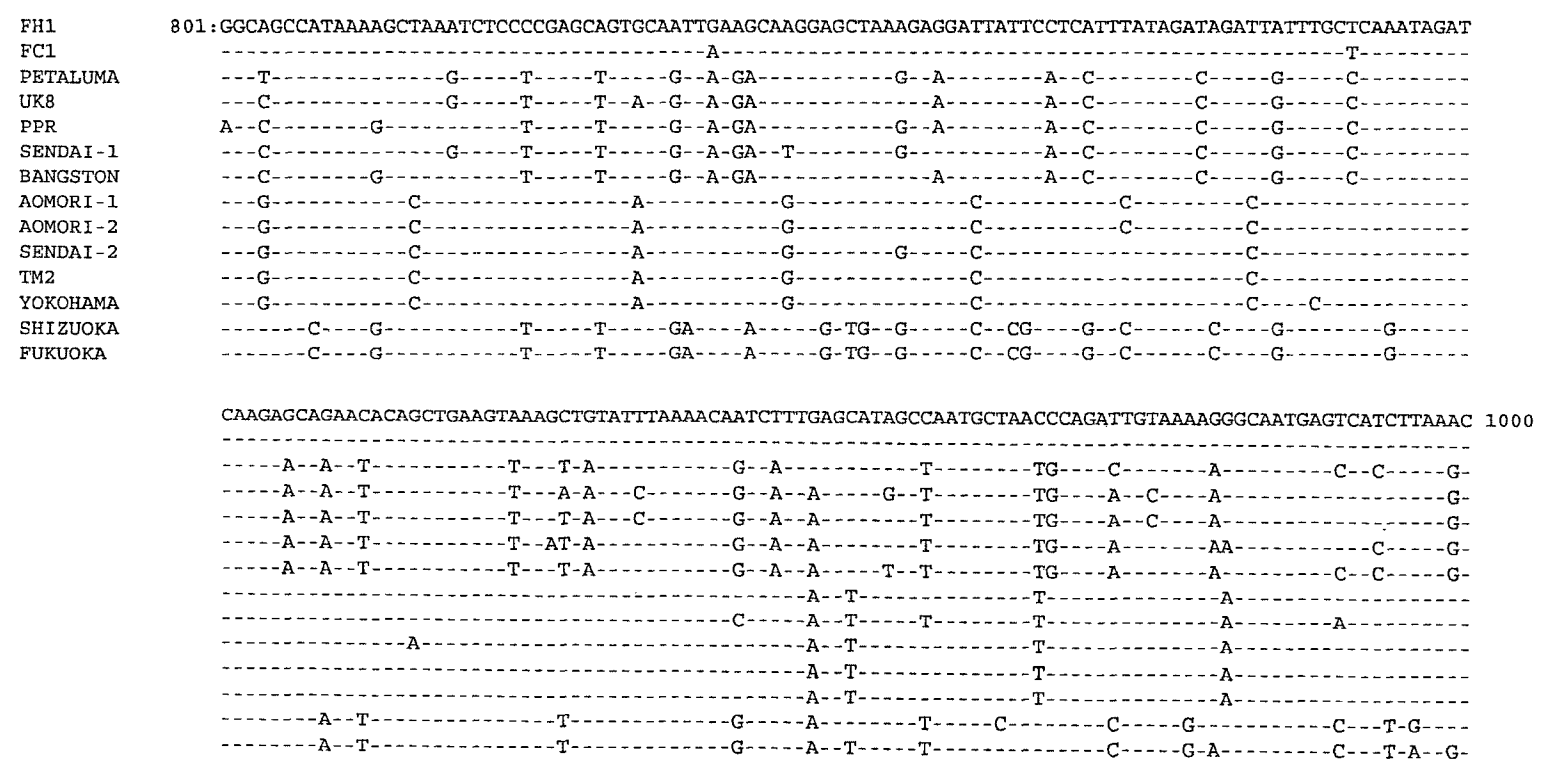

FIGS. 4A-4G show gag nucleotide sequence comparison of cat #FC1, subject #FH1 and FIV strains. Gag sequences of cat #FC1 (SEQ ID NO: 42) and subject #FH1 were compared to all FIV strains available in our laboratory (SEQ ID NO: 43 is $FIV_{PETALUMA}$; SEQ ID NO: 44 is $FIV_{UK8}$; SEQ ID NO: 45 is $FIV_{PPR}$; SEQ ID NO:46 is $FIV_{SENDAI-1}$; SEQ ID NO: 47 is $FIV_{Bang}$; SEQ ID NO: 48 is $FIV_{AOMORI-1}$; SEQ ID NO: 49 is $FIV_{AOMORI-2}$; SEQ ID NO: 50 is $FIV_{SENDAI-2}$, SEQ ID NO: 51 is $FIV_{TM2}$; SEQ ID NO: 52 is $FIV_{YOKOHAMA}$; SEQ ID NO: 53 is $FIV_{SHIZUOKA}$; and SEQ ID NO: 54 is $FIV_{FUKUOKA}$. The consensus sequence of subject #FH1 is shown at the top (SEQ ID NO: 41). Nucleotides identical to the consensus sequence of subject #FH1 (top sequence) are designated as a dot and those which differ from the consensus are presented with the appropriate nucleotide symbols. Gaps in sequence are presented as hyphens.

FIGS. 5A-5E show HIV-1 and FIV Western blot analysis of experimentally FIV-infected cats and pet cats. SPF cats #H3J, #D55, #455, and #X3D were experimentally infected with $FIV_{Pet}$ (subtype A), $FIV_{UK8}$ (subtype A), $FIV_{Shi}$ (subtype D), and $FIV_{Bang}$ (subtype $A_{gag}/B_{Env}$), respectively. $FIV_{Bang}$ has Gag sequence of FIV subtype A and Env sequence of FIV subtype B. These serum were reacted with HIV-1 Western blots (FIGS. 5A and 5B) or FIV Western blots (FIGS. 5C, 5D, and 5E). Serum samples of these cats before FIV infection were negative by both FIV and HIV-1 Western blot analyses (data not shown). Serum from pet cats #FC1 and #FC2 were also tested for their reactivity to HIV-1 and FIV antigens. Cat #C9V (7 months post-inoculation serum shown) is an SPF cat inoculated with FIV isolated from pet Cat #FC1. All sera were incubated at serum dilution of 1:100. All procedures are identical to those described in FIGS. 1 and 3 unless stated otherwise. Key bands are highlighted with an arrowhead on the left. FDA-approved serum incubation periods of 20 hours for Cambridge Biotech HIV-1 Western Blot Kit (FIG. 5A) and 0.5 hour for Bio-Rad Novapath HIV-1 Immunoblot Kit (FIG. 5B) were performed with the cat sera. Serum incubation for FIV Western blots was 20 hours (FIGS. 5C, 5D, and 5E).

FIGS. 7A and 7B show temporal development of cross-reactive antibodies to HIV-1. FIV and HIV-1 immunoblots are shown using selected sera from: FIG. 7A, FIV-infected cats from different weeks post-inoculation (wk pi or pi); and FIG. 7B, FIV-vaccinated cats from different weeks post-vaccination (post-vaccination number. Sera were compared to their pre-inoculation or pre-vaccination sera (Pre).

FIG. 8A: Cat sera were absorbed against inactivated FIV-infected cells followed by competition on HIV-1 immunoblots by inactivated FIV. Absorptions were also performed with PBS, uninfected cat FeT-J cells, and uninfected human H9/HuT-78 cells. FIG. 8B: Sera were absorbed against PBS, uninfected cells lysate, or inactivated HIV-infected HuT-78 cells prior to incubation with HIV-1 immunoblot strips. Absorptions were performed for 2 hours at room temperature before development with anti-cat reagents. FIG. 8C: FIV-vaccinated cat sera containing neutralizing antibodies to HIV-1 (Cat #C6G and #C9K) and sera from uninfected FeT-J cell immunized cats (Cats #C6E and #3G5) were tested at 1:100 dilution for reactivity to 5 μg/ml of either uninfected FeT-J cells, uninfected HuT-78 cells, or purified $FIV_{Pet}$. Vaccinated cat sera had reactivity to FIV surface Env gp95 (arrow head). No significant reactivities were detected to uninfected FeT-J and HuT-78 proteins at 95 kDa, 120 kDa, and 160 kDa, suggesting that serum reactivity to HIV-1 and FIV envelopes were not due to nonspecific reactivity to cellular proteins. In addition, cats immunized with uninfected FeT-J cells had no reactivity to cellular proteins at 95 kDa but had antibodies reactive to cellular proteins close to 120 kDa and 160 kDa. However, these anti-cellular antibodies were close but distinctly different from reactivity to HIV-1 gp120 and gp160. FIG. 8D: Serum from a cat immunized with uninfected FeT-J cells was absorbed against PBS, FeT-J, H9/HuT-78 cells, and FIV-infected Fet-J cells. Reactivities in serum from Cat #305 were readily absorbed against uninfected cat and human cells. Immunoglobulin levels of all absorbed sera were not significantly altered by infected-cell absorptions when compared to PBS and uninfected-cell absorbed sera. Seven % PAGE gels were used for developing immunoblots to increase resolution of high molecular weight proteins. Molecular weights (M) are presented in kDa.

FIG. 9A: Sera from cats immunized with dual-subtype FIV vaccine were tested by ELISA using recombinant HIV-1$_{BRU}$ p24, HIV-1$_{IIIB}$ gp160, and FIV p24. ELISA results at serum dilution of 1:300 are presented as mean difference between pre- and post-vaccination sera. FIG. 9B: PBMC from dual-subtype FIV vaccinated cats at 2 weeks post-5th vaccination were tested for interferon-γ production in response to recombinant HIV-1$_{BRU}$ p24, HIV-1$_{IIIB}$ gp160, and FIV p24. All PBMC stimulated with SEA were positive for IFNγ production (data not shown). The average of the triplicate samples are shown for IFNγ production. Standard deviations of the average IFNγ titer were less than 10% of the mean.

FIGS. 10A and 10B show sequence alignments for partial FIV gag sequence from subject #FH1 PBMC following Real-time PCR. The Consensus sequence is SEQ ID NO: 55; SEQ ID NO: 56 is a partial $FIV_{Pet}$ gag sequence; SEQ ID NO: 57 is a partial $FIV_{Bang}$ sequence; SEQ ID NO: 58 is a partial $FIV_{JSY3}$ gag sequence; SEQ ID NO: 59 is a partial $FIV_{UK8}$ gag sequence; SEQ ID NO: 60 is a partial $FIV_{shizuoka}$ sequence; SEQ ID NO: 61 is a partial $FIV_{AOMORI\ 1}$ sequence; SEQ ID NO: 62 is a partial $FIV_{TM2}$ gag sequence; SEQ ID NO: 63 is a partial FIV reverse transcriptase forward sequence; SEQ ID NO: 64 is a partial FIV reverse transcriptase probe sequence; SEQ ID NO: 65 is a partial FIV reverse transcriptase reverse sequence; SEQ ID NO: 66 is a FC1 gag sequence; SEQ ID NO: 67 is the A9=4 sequence; SEQ ID NO: 68 is the B4=5 sequence.

BRIEF DESCRIPTION OF THE SEQUENCES

Figures 1C, 1D:
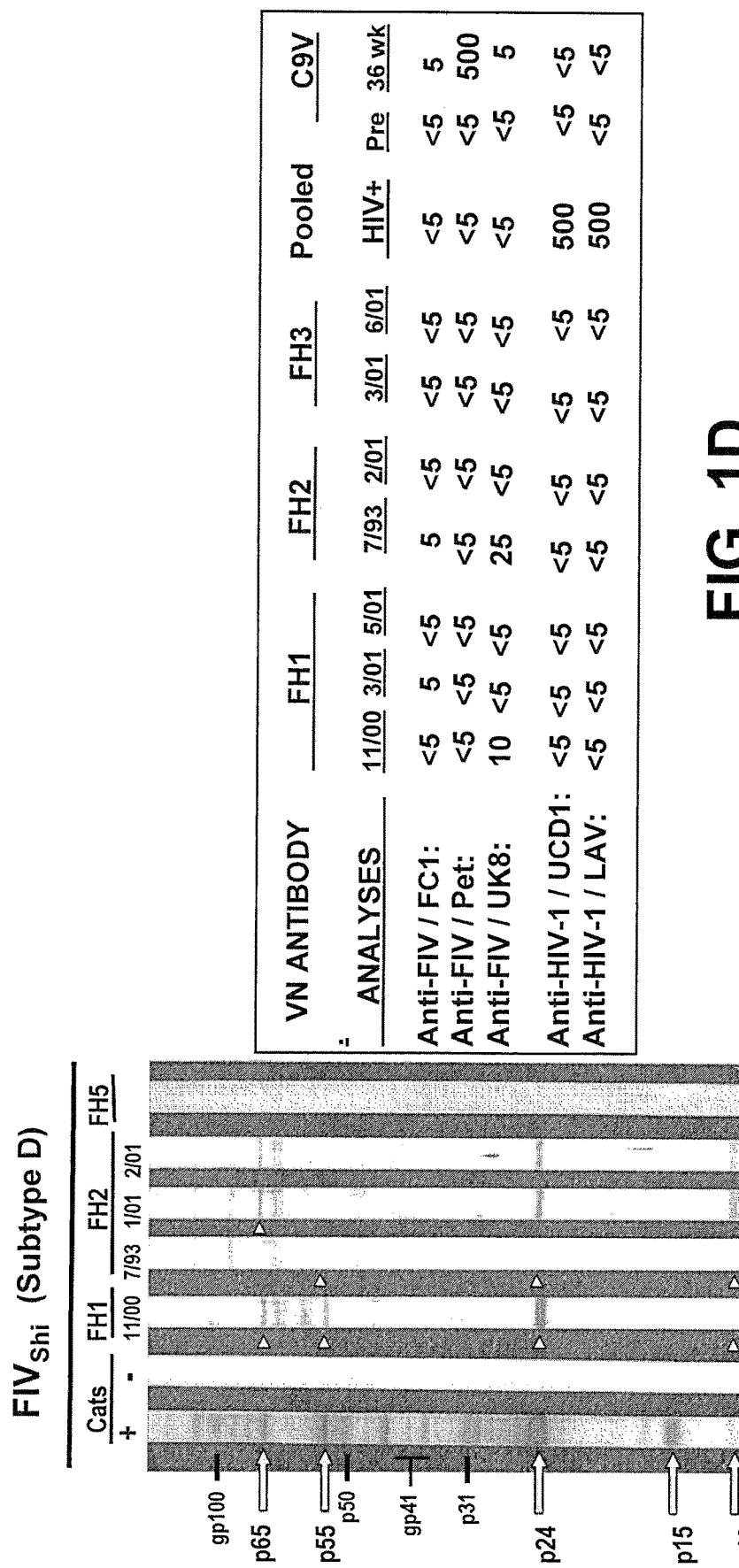

SEQ ID NO. 1 is a sense primer or amplification of FIV gag that can be used according to the present invention.

SEQ ID NO. 2 is a antisense primer or amplification of FIV gag that can be used according to the present invention.

SEQ ID NO: 3 is a nucleotide sequence of the present invention.

SEQ ID NO: 4 is a nucleotide sequence of the present invention.

SEQ ID NO: 5 is a nucleotide sequence of the present invention.

SEQ ID NO: 6 is a nucleotide sequence of the present invention.

SEQ ID NO: 7 is a nucleotide sequence of the present invention.

SEQ ID NO: 8 is a nucleotide sequence of the present invention.

SEQ ID NO: 9 is a nucleotide sequence of the present invention.

SEQ ID NO: 10 is a nucleotide sequence of the present invention.

SEQ ID NO: 11 is a nucleotide sequence of the present invention.

SEQ ID NO: 12 is a nucleotide sequence of the present invention.

SEQ ID NO: 13 is a nucleotide sequence of the present invention.

SEQ ID NO: 14 is a nucleotide sequence of the present invention.

SEQ ID NO: 15 is a nucleotide sequence of the present invention.

SEQ ID NO: 16 is a nucleotide sequence of the present invention.

SEQ ID NO: 17 is a nucleotide sequence of the present invention.

SEQ ID NO: 18 is a nucleotide sequence of the present invention.

SEQ ID NO: 19 is a nucleotide sequence of the present invention.

SEQ ID NO: 20 is a nucleotide sequence of the present invention.

SEQ ID NO: 21 is a nucleotide sequence of the present invention.

SEQ ID NO: 22 is an amino acid sequence of the present invention.

SEQ ID NO: 23 is an amino acid sequence of the present invention.

SEQ ID NO: 24 is an amino acid sequence of the present invention.

SEQ ID NO: 25 is an amino acid sequence of the present invention.

SEQ ID NO: 26 is an amino acid sequence of the present invention.

SEQ ID NO: 27 is an amino acid sequence of the present invention.

SEQ ID NO: 28 is an amino acid sequence of the present invention.

SEQ ID NO: 29 is an amino acid sequence of the present invention.

SEQ ID NO: 30 is an amino acid sequence of the present invention.

SEQ ID NO: 31 is an amino acid sequence of the present invention.

SEQ ID NO: 32 is an amino acid sequence of the present invention.

SEQ ID NO: 33 is an amino acid sequence of the present invention.

SEQ ID NO: 34 is an amino acid sequence of the present invention.

SEQ ID NO: 35 is an amino acid sequence of the present invention.

SEQ ID NO: 36 is an amino acid sequence of the present invention.

SEQ ID NO: 37 is an amino acid sequence of the present invention.

SEQ ID NO: 38 is an amino acid sequence of the present invention.

SEQ ID NO: 39 is an amino acid sequence of the present invention.

SEQ ID NO: 40 is an amino acid sequence of the present invention.

SEQ ID NO: 41 is a nucleotide sequence of the present invention.

SEQ ID NO: 42 is a nucleotide sequence of the present invention.

SEQ ID NO: 43 is a nucleotide sequence of the present invention.

SEQ ID NO: 44 is a nucleotide sequence of the present invention.

SEQ ID NO: 45 is a nucleotide sequence of the present invention.

SEQ ID NO: 46 is a nucleotide sequence of the present invention.

SEQ ID NO: 47 is a nucleotide sequence of the present invention.

SEQ ID NO: 48 is a nucleotide sequence of the present invention.

SEQ ID NO: 49 is a nucleotide sequence of the present invention.

SEQ ID NO: 50 is a nucleotide sequence of the present invention.

SEQ ID NO: 51 is a nucleotide sequence of the present invention.

SEQ ID NO: 52 is a nucleotide sequence of the present invention.

SEQ ID NO: 53 is a nucleotide sequence of the present invention.

SEQ ID NO: 54 is a nucleotide sequence of the present invention.

SEQ ID NO: 55 is a nucleotide sequence of the present invention.

SEQ ID NO: 56 is a nucleotide sequence of the present invention.

SEQ ID NO: 57 is a nucleotide sequence of the present invention.

SEQ ID NO: 58 is a nucleotide sequence of the present invention.

SEQ ID NO: 59 is a nucleotide sequence of the present invention.

SEQ ID NO: 60 is a nucleotide sequence of the present invention.

SEQ ID NO: 61 is a nucleotide sequence of the present invention.

SEQ ID NO: 62 is a nucleotide sequence of the present invention.

SEQ ID NO: 63 is a nucleotide sequence of the present invention.

SEQ ID NO: 64 is a nucleotide sequence of the present invention.

SEQ ID NO: 65 is a nucleotide sequence of the present invention.

SEQ ID NO: 66 is a nucleotide sequence of the present invention.

SEQ ID NO: 67 is a nucleotide sequence of the present invention.

SEQ ID NO: 68 is a nucleotide sequence of the present invention.

DETAILED DESCRIPTION OF THE INVENTION

The subject invention concerns materials and methods for detecting, preventing and treating infection by FIV in humans and other non-feline animals susceptible to infection by FIV. The present invention is based on the surprising discovery that FIV can be transmitted from cats to humans and can infect human cells in vivo. Human subjects have been identified that are FIV positive and appear to have been infected through contact with their pet cats. Infection of humans by FIV has been demonstrated by confirmation of the presence of FIV nucleotide sequences in human cells using polymerase chain reaction (PCR) and by Western blot detection of FIV proteins expressed in human cells. Sequence analysis confirms that the subject is infected with FIV. Both of the human subjects infected with FIV identified thus far are currently clinically and immunologically asymptomatic. It has also been demonstrated that antibodies to FIV cross-react with HIV proteins. In addition, antibodies from FIV vaccinated animals can neutralize HIV-1 virus. The subject invention also concerns materials and methods for preventing and treating infection by HIV in humans.

One aspect of the subject invention concerns methods for detecting FIV infection of human cells. One method of the present invention comprises detecting the presence of antibodies that bind to an FIV protein or peptide, or nucleotide sequences of FIV. FIV diagnostic tests of the invention include ELISA, Western blot, and PCR tests. Current commercially available HIV antibody tests cross react with FIV proteins and, therefore, can give "false positive" results in subjects which are not infected with HIV but which are infected with FIV. Thus, FIV diagnostic tests for humans are needed in facilities doing HIV testing, such as hospitals and blood banks, in order to screen false positives and indeterminant results obtained from current HIV tests. Methods for detecting and diagnosing FIV are known in the art and can be readily incorporated into assays for the testing of biological samples from humans for HIV infection. U.S. Pat. Nos. 5,037,753, 5,118,602, 5,275,813, 5,510,106, and 5,565,319 describe assays and compositions for detecting FIV. Materials and methods for detecting and diagnosing HIV are disclosed in U.S. Pat. Nos. 4,708,818, 5,055,391, 5,108,891, 5,135,684, and 5,922,533. Diagnostic HIV assays are also commercially available from Bio-Rad Laboratories, Hercules, Calif. Methods of testing biological samples from humans for FIV infection only (and not HIV) are also contemplated by the present invention. Methods for FIV detection include PCR assaying for proviral FIV nucleotide sequences, RT-PCR assaying for FIV RNA nucleotide sequences, oligonucleotide probe assays (including Real-time PCR), and antibody-based assays. Antibody-based assays include, for example, methods to detect the presence of antibodies to FIV, such as ELISA and Western blots, and methods to detect the presence and/or expression of FIV proteins in human biological samples. In one embodiment, a biological sample from a human that is being assayed for the presence of antibodies to HIV or HIV sequences is assayed for the presence of antibodies to FIV or FIV sequences.

The present invention concerns materials and methods for inducing an immune response to FIV in a human or non-feline animal that is susceptible to infection by FIV. The present invention also concerns materials and methods for inducing an immune response to HIV in a human. In one embodiment, an amount of an FIV immunogen effective to induce an immune response is administered to the human or animal. FIV immunogens that can be used include, for example, synthetic FIV peptide, natural or recombinant FIV protein or a fragment thereof, polynucleotide comprising a sequence that encodes an FIV protein or fragment thereof, polynucleotide comprising a sequence that encodes an FIV protein or a fragment thereof and an HIV protein (such as NeF protein) or a fragment thereof, inactivated or attenuated whole FIV viral isolate, FIV viral fragment, inactivated cells infected with FIV, and compositions comprising FIV and HIV proteins or fragments thereof.

The present invention also concerns materials and methods for preventing FIV infection in humans and other animals. Specifically contemplated are methods and vaccine compositions which can be administered to human subjects and other susceptible host animals which will prevent infection by FIV. In one embodiment, an amount of an FIV immunogen effective to induce an immune response is administered to the human or animal. FIV immunogens that can be used include, for example, synthetic FIV peptide, natural or recombinant FIV protein or a fragment thereof, polynucleotide comprising a sequence that encodes an FIV protein or fragment thereof, polynucleotide comprising a sequence that encodes an FIV protein or a fragment thereof and an HIV protein (such as NeF protein) or a fragment thereof, inactivated or attenuated whole FIV viral isolate, FIV viral fragment, inactivated cells infected with FIV, and compositions comprising FIV and HIV proteins or fragments thereof. In a preferred embodiment, the FIV immunogen comprises an epitope of an FIV protein, such as core gag protein or envelope protein, that is evolutionarily conserved between FIV and HIV. Persons that have higher exposure to cats, such as veterinarians, scientists that use cats for research purposes, cat breeders, etc., would be candidates for receiving a vaccine treatment. Other animals which can be treated according to methods of present invention include dogs, horses, and captive non-domesticated animals such as those found in zoos and circuses, including tigers and lions.

The subject invention also concerns materials and methods for treating persons and other animals that are infected with FIV. In one embodiment, an effective amount of a composition which can induce an immune response against FIV is administered to a person or animal in need of such treatment. In another embodiment, one or more antiretroviral drugs can be administered to the person or animal. Antiretroviral drugs which can be used in the present invention include, but are not limited to, nucleoside analogs, such as azidothymidine (AZT) and lamivudine (3TC), non-nucleoside inhibitors of retroviral reverse transcriptase, and retroviral protease inhibitors. Published international patent application WO 99/60988 describes the use of a combination of AZT, 3TC, and a retroviral protease inhibitor to treat FIV infection. In a further embodiment, polynucleotide sequences that are antisense to nucleotide sequences of FIV can be administered to the person or animal.

In another embodiment, a person or animal can be treated using one or more antibody that cross-reacts with both FIV and HIV antigens. Alternatively, a cocktail of one or more antibody that is specific to an FIV antigen and one or more antibody that is specific to an HIV antigen can be administered.

In another embodiment, a person or non-feline animal can be treated using an FIV immunogen that induces an immune response against FIV. FIV immunogens that can be used include, for example, synthetic FIV peptide, natural or recombinant FIV protein or a fragment thereof, polynucleotide comprising a sequence that encodes an FIV protein or fragment thereof, polynucleotide comprising a sequence that encodes an FIV protein or a fragment thereof and an HIV protein (such as NeF protein) or a fragment thereof, inactivated or attenuated whole FIV viral isolate, FIV viral fragment, inactivated cells infected with FIV, and composition comprising FIV and HIV proteins or fragments thereof.

In a further embodiment, antiretroviral drugs can be used in combination with FIV immunogen treatment or antibody therapy, or both, described above. Other animals which can be treated according to methods of present invention include dogs, horses, and captive non-domesticated animals such as those found in zoos and circuses, including tigers and lions.

The subject invention also concerns materials and methods for preventing HIV infection in humans that are not infected with HIV. In one embodiment, an FIV immunogen is administered to a person. In a preferred embodiment, the FIV immunogen induces an immune response against one or more subtypes of FIV. FIV immunogens that can be used include, for example, synthetic FIV peptide, natural or recombinant FIV protein or a fragment thereof, polynucleotide comprising a sequence that encodes an FIV protein or fragment thereof, polynucleotide comprising a sequence that encodes an FIV protein or a fragment thereof and an HIV protein (such as NeF protein) or a fragment thereof, inactivated or attenuated whole FIV viral isolate, FIV viral fragment, inactivated cells infected with FIV, and composition comprising FIV and HIV proteins or fragments thereof. In another embodiment, a person or animal can be administered an FIV immunogen and then subsequently receive a secondary administration of an HIV immunogen. Preferably, the FIV immunogen elicits an immune response against more than one FIV subtype. HIV immunogens can include core gag protein (p24) and envelope protein (gp100/gp120). In a preferred embodiment, the FIV immunogen comprises an epitope of an FIV protein, such as core gag protein or envelope protein, that is evolutionarily conserved between FIV and HIV.

The invention also concerns materials and methods for treating persons that are already infected with HIV. In one embodiment, an FIV immunogen is administered to a person. In a preferred embodiment, the FIV immunogen induces an immune response against one or more subtypes of FIV. FIV immunogens that can be used include, for example, synthetic FIV peptide, natural or recombinant FIV protein or a fragment thereof, polynucleotide comprising a sequence that encodes an FIV protein or fragment thereof, polynucleotide comprising a sequence that encodes an FIV protein or a fragment thereof and an HIV protein (such as NeF protein) or a fragment thereof, inactivated or attenuated whole FIV viral isolate, FIV viral fragment, inactivated cells infected with FIV, and composition comprising FIV and HIV proteins or fragments thereof. In another embodiment, a person or animal can be administered an FIV immunogen and then subsequently receive a secondary administration of an HIV immunogen. Preferably, the FIV immunogen elicits an immune response against more than one FIV subtype. HIV immunogens can include core gag protein (p24) and envelope protein (gp100/gp120).

In another embodiment, a person or animal infected with HIV can be treated using one or more antibody that cross-reacts with both an FIV protein or antigen and an HIV protein or antigen. Alternatively, a cocktail of one or more antibody that is specific to an FIV antigen and one or more antibody that is specific to an HIV antigen can be administered.

In a further embodiment, antiretroviral drugs can be used in combination with FIV immunogen treatment or antibody therapy, or both, described above. Antiretroviral drugs for treating HIV are known in the art and include nucleoside analogs such as azidothymidine (AZT) and lamivudine (3TC), non-nucleoside inhibitors of retroviral reverse transcriptase, and retroviral protease inhibitors.

The compositions of the invention, when administered to a human or other animals susceptible to FIV infection, can induce protective humoral and/or cellular immune responses against infection by FIV. Preferably, the composition can induce immune responses against multiple strains of FIV. More preferably, the compositions of the invention can induce immune responses against homologous and heterologous strains of FIV. The compositions can be, for example, composed of synthetic FIV peptide, natural or recombinant FIV protein or a fragment thereof, polynucleotide comprising a sequence that encodes an FIV protein or fragment thereof, polynucleotide comprising a sequence that encodes an FIV protein or a fragment thereof and an HIV protein (such as NeF protein) or a fragment thereof, inactivated or attenuated whole FIV viral isolate, FIV viral fragment, inactivated cells infected with FIV, and composition comprising FIV and HIV proteins or fragments thereof, or a combination of any of the above. In a preferred embodiment, the vaccine composition of the subject invention comprises peptides, proteins or strains of FIV from two different FIV subtypes. In one embodiment, FIV subtype A and FIV subtype D are represented in the composition. Preferably, the composition comprises peptides, proteins or viral isolates from three FIV strains, each strain from a different FIV subtype. More preferably, at least one FIV strain from each of FIV subtype A, subtype B and subtype D is included in the vaccine composition. Compositions directed to multiple subtypes of FIV are described in U.S. Pat. No. 5,846,825.

The compositions of the subject invention also encompass recombinant viral vector-based FIV constructs that may comprise, for example, FIV env, gag/pro, or env-gag/pro. Any suitable viral vector that can be used to prepare recombinant vector/FIV constructs is contemplated for use with the subject invention. For example, viral vectors derived from adenovirus, avipox, feline herpesvirus, vaccinia, canarypox, entomopox, swinepox and others known in the art can be used with the compositions and methods of the present invention. Recombinant polynucleotide vectors that encode and express FIV components can be constructed using standard genetic engineering techniques known in the art. In addition, the various compositions described herein can be used separately and in combination with each other. For example, primary immunizations of a person or other animal may utilize recombinant vector-based FIV constructs, having single or multiple subtype components, followed by secondary boosts with vaccine compositions comprising synthetic FIV peptides and/or recombinant FIV proteins. Other immunization protocols with the vaccine compositions of the invention are apparent to persons skilled in the art and are contemplated within the scope of the present invention.

Natural, recombinant or synthetic polypeptides of FIV viral proteins, and peptide fragments thereof, can also be used as compositions according to the subject methods. In a preferred embodiment, FIV polypeptides derived from multiple FIV subtypes are combined in a vaccine composition and are used to vaccinate a human or other susceptible animal in need of such treatment. For example, polypeptides based on the FIV envelope glycoprotein from at least two prototype FIV strains from different subtypes can be combined in the vaccine. The polypeptides may be homologous to one strain or may comprise "hybrid" or "chimeric" polypeptides whose amino acid sequence is derived from joining or linking polypeptides from at least two distinct FIV subtypes. Procedures for preparing FIV polypeptides are well known in the art. For example, FIV polypeptides can be synthesized using solid-phase synthesis methods (Merrifield, 1963). FIV polypeptides can also be produced using recombinant DNA techniques wherein a polynucleotide molecule encoding an FIV protein or peptide is expressed in a host cell, such as bacteria, yeast, or mammalian cell lines, and the expressed protein purified using standard techniques of the art.

According to the methods of the subject invention, the FIV vaccine compositions described herein are administered to a human or other animal susceptible to FIV infection in an effective amount and in a manner capable of inducing protective immunity against subsequent challenge or infection of the human or animal by FIV. The vaccines are typically administered parenterally, by injection, for example, either subcutaneously, intraperitoneally, or intramuscularly. Other modes of vaccine administration contemplated by the invention include oral or nasal administration. Usually, the vaccines are administered to a subject at least two times, with an interval of one or more weeks between each administration. However, other regimens for the initial and booster administrations of the vaccine are contemplated, and may depend on the judgment of the practitioner and the particular host animal being treated.

The vaccine compositions of the subject invention can be prepared by procedures well known in the art. For example, the vaccines are typically prepared as injectables, e.g., liquid solutions or suspensions. The vaccines are administered in a manner that is compatible with dosage formulation, and in such amount as will be therapeutically effective and immunogenic in the recipient. The optimal dosages and administration patterns for a particular vaccine formulation can be readily determined by a person skilled in the art.

Virus for use in a vaccine formulation may be inactivated or attenuated using methods known in the art. For example, whole virus and infected cells can be inactivated or attenuated by exposure to paraformaldehyde, formalin, phenol, UV light, elevated temperature and the like.

In one embodiment, a biological sample, such as blood, serum, saliva and the like, is obtained from a person and assayed for the presence of antibodies that can bind specifically to FIV or an FIV antigen. The sample can be assayed for antibodies that bind with all subtypes or strains of FIV or antigens thereof, as well as for antibodies that are specific to a particular subtype or strain of FIV or antigen thereof so as to facilitate diagnosis of the FIV subtype or strain infecting the subject. The sample can optionally be assayed for the presence of antibodies that bind to HIV or an HIV antigen. Assay techniques, e.g., ELISA and Western blotting, for detecting antibodies to FIV and HIV are known in the art. In another embodiment, a biological sample is assayed for the presence of FIV-specific nucleotide sequences and/or proteins. Standard PCR and nucleotide hybridization techniques can be used to amplify and detect the presence of FIV-specific nucleotide sequences in a sample. RT-PCR can be used to detect FIV RNA sequences. FIV oligonucleotide primers and probes for use in such techniques and which are substantially complementary with a portion of the FIV genomic sequence or FIV RNA sequences can be readily prepared based on known FIV sequences.

Polymerase chain reaction (PCR) is based on repeated cycles of denaturation of double-stranded DNA, followed by oligonucleotide primer annealing to the DNA template, and primer extension by a DNA polymerase (Mullis et al. U.S. Pat. Nos. 4,683,195, 4,683,202, and 4,800,159; Saiki et al. 1985). The oligonucleotide primers used in PCR are designed to anneal to opposite strands of the DNA, and are positioned so that the DNA polymerase-catalyzed extension product of one primer can serve as the template strand for the other primer. The PCR amplification process results in the exponential increase of discrete DNA fragments whose length is defined by the 5' ends of the oligonucleotide primers. Nucleotide hybridization methods are disclosed, for example, in U.S. Pat. No. 4,358,535.

The subject invention also concerns antibodies that cross-react with both FIV and HIV antigens. Antibodies can be prepared and isolated using standard methods known in the art. For example, a suitable animal can be immunized with an FIV immunogen via one or more intramuscular or subcutaneous injections, optionally with an adjuvant, over a period of time. Immunized animals can be periodically bled and antibodies isolated from the antisera. The anti FIV antibodies can then be screened for cross-reactivity with FIV. Antibodies of the present invention can be polyclonal or monoclonal. Monoclonal antibodies can be prepared according to the methods of Kohler and Milstein (1976). In those cases where a monoclonal antibody of the present invention is to be used in a human, the antibody can be Ahumanized@ to minimize immune reactions against the antibody by the human system. Techniques for humanizing antibodies are well known in the art and are described in U.S. Pat. Nos. 5,807,715, 5,693,762, 5,585,089, 5,530,101, and Morrison et al. (1984).

The subject invention also concerns compositions comprising at least one FIV protein and/or antigen or fragment thereof and at least one HIV protein and/or antigen or fragment thereof. In one embodiment, the composition comprises epitopes of FIV and HIV proteins that are evolutionarily conserved between the viruses. In a preferred embodiment, the composition comprises core gag protein and/or viral envelope protein.

The subject invention also concerns polynucleotide molecules that encode at least one FIV protein or fragment thereof and at least one HIV protein (such as NeF) or fragment thereof.

The subject invention also concerns materials and methods for preventing infection in humans and other animals by lentivirus such as CAEV and SIV.

All patents, patent applications, provisional applications and publications referred to or cited herein are incorporated by reference in their entirety to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1 B

Immunization of Humans with FIV

Western Blot Analysis: FIV-Petaluma ($FIV_{pet}$, subtype A), FIV-Shizuoka ($FIV_{Shi}$, subtype B) and FIV-Bangston ($FIV_{Bang}$, subtype D) Western blots were reacted with sera from subjects #FH1, #FH2, and #FH5 and from cats #FC1, #FC2, and #C9V at 1:100 dilution for 20 hours (room temperature). Subject #FH5 served as a control individual, having had minimal exposure to cats. Experimentally FIV-infected cats were used as the source of strongly reactive control sera. Uninfected specific pathogen-free (SPF) cats were used as the source of non-reactive control sera. Except for the FIV mini-Western blot strips and the duration of incubation, all reagents and methods for testing human sera were identical to those described in Bio-Rad Novapath HIV-1 Immunoblot Kit (Bio-Rad Laboratories, Hercules, Calif.). FIV mini-Western blot strips were produced using sucrose-gradient purified FIV at 1.5 μg/strip as previously described (Yamamoto et al., 1988a). Cat control sera were tested using the alkaline phosphate enzyme-linked anti-cat IgG antibodies (Chemicon International Inc., Temecula, Calif.) at 0.12 μg/ml and all procedures were performed in a total volume of 1.5 ml per strip. Aside from these modifications, the reagents and procedure for testing cat sera were identical to those described in the Bio-Rad Western blot kit.

Positive and negative control human sera from the Bio-Rad HIV-1 Immunoblot Kit and Cambridge HIV-1 Western Blot Kit (Cambridge Biotech, Rockville, Md.) were used as controls for the respective HIV-1 Western blot strips. Serum from subject #FH5 was used as an additional negative control for Western blots from both companies. Except for the duration of incubation, all reagents and methods for testing human sera were identical to those described in Bio-Rad=s and Cambridge=s HIV-1 Western blot kits. Serum from FIV-infected cats collected from 6 to 32 months post-infection were also tested with HIV-1 or FIV Western blots.

Molecular Analysis: Primary PBMC were cocultured with mitogen-stimulated PBMC from either a FIV-seronegative individual or an SPF cat. The mitogens used were Staphylococcal enterotoxin A (SEA, 0.5 μg/ml) or concanavalin A (Con A, 1 μg/ml). After 1.5 to 3 weeks of culture, RNA and genomic DNA were extracted from the cultured PBMCs by guanidine isothiocyanate-phenol procedure using TRIZOL Reagent (GIBCO BRL, Rockville, Md.) and QIAamp DNA blood Mini kit (QIAGEN, Valencia, Calif.), respectively. The levels of reverse transcriptase (RT) activity present in cultured fluids were measured by a RT assay (Yamamoto et al., 1988b). Viral RNA was extracted from plasma using QIAamp Viral RNA Mini kit (QIAGEN, Valencia, Calif.). After DNase treatment, RNA was reverse transcribed to cDNA with AMV RT and random hexamer primers. One μg of cDNA from cell associated RNA, cDNA from plasma RNA (in 62.5 μl of plasma), and genomic DNA from $1\times10^5$ cells were used for PCR analysis. Nested PCR for FIV gag was performed using primer sets as previously described (Hohdatsu et al. 1998). FIV whole gag genes were amplified by single PCR with sense primer GAGF (5=-CAACAAGGTAGGAGAGATTCTACA-3=) (SEQ ID NO:1) and antisense primer, GAGR (5=-TAAAATTGT-TATATCTGCTCCTGT-3') (SEQ ID NO:2). Primers used for detection of HIV-1 were previously described (Ou et al., 1988). Amplification products of the expected size were cloned into the pCR 2.1 TOPO cloning vector (Invitrogen, Carlsbad, Calif.) and sequenced (ICBR core lab, UF).

Sequences of FIV strains and other retroviruses were obtained from NCBI/GenBank and analyzed by CRYSTAL W program and Basic Local Alignment Search Tool (BLAST).

Whole blood from subject #FH1 was submitted to College of Veterinary Medicine at the University of Florida by the physician upon the subject=s request. Positive antibody reactivity was found by Western blot to FIV major core capsid p24 (Ca) protein and precursor Gag p55, with weak reactivity to FIV minor core nucleoprotein p10 and potential FIV RT p65 protein (FIGS. 1A-D). The reactivities observed on these blots are not likely to be non-specific, since reactivity to p24 was abrogated by preasborption of sera with FIV-infected cells (data not shown). Sera from #FH1 and #FH2 were able to neutralize FIV, but not HIV-1, in vitro. Antibody reactivity of #FH1 to FIV proteins could have been induced by antigenic stimulation via proteins shed by the subject=s FIV infected cat or could be the result of actual infection. Hence, PBMC and plasma from #FH1 were tested for FIV. Plasma was negative for FIV gag by nested RT-PCR and cells were negative by FIV proviral PCR. To determine the presence of infected cells, a sensitive coculture amplification technique was used in which PBMC from the subject were cocultured with concanvalin A (Con A)-stimulated PBMC from either a FIV-seronegative individual or a SPF laboratory cat. Only a human-human cocultured cell preparation was positive for a 300 bp sequence at the p24 region by nested RT-PCR. RT-PCR (without nesting) with FIV gag primers determined the presence of a 1500 bp band indicating detection of FIV gag RNA (FIGS. 2A-2D). The control culture consisting of cells from SPF cat or FIV-seronegative individual were negative by the same assays. Thus, the entire gag gene was found to reside in PBMC from the #FH1 subject. Culture fluids were negative for FIV by RT assay.

Figure 3A:
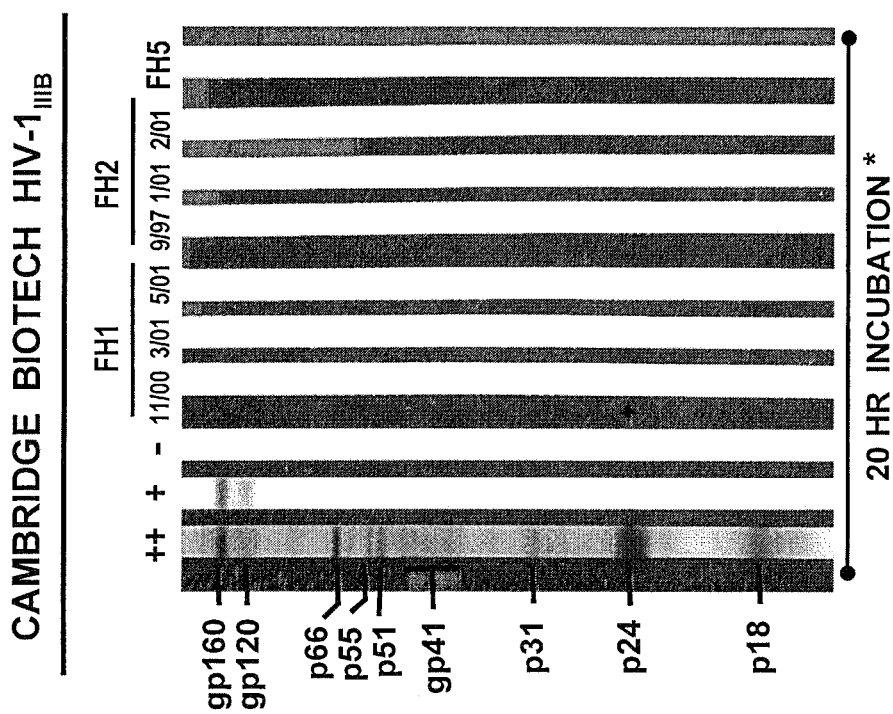

Since a full RNA gag sequence was derived from PBMC, serum from #FH1 was retested using FDA-approved HIV-1 Western blot assays (FIGS. 3A-C). The previous HIV-1 Western blot test performed by licensed diagnostic laboratories used the Western blot kit from Cambridge (HIV-1$_{IIIB}$, subtype B). Western blot strips from Bio-Rad Laboratories use HIV-1$_{UCD1}$ (subtype B) as the source of viral proteins. Serum from #FH1 reacted to both sets of strips at p24 and weakly at p55, but unlike FIV Western blot results, no minor core and RT reactions were observed. This pattern of serum reactivities to HIV and FIV proteins suggest that the subject=s antibodies were more likely induced by infection with FIV rather than HIV-1 (FIGS. 1A-D and 3A-C). Further, reactivities to HIV-1 p24 on both HIV-1$_{IIIB}$ and HIV-1$_{UDC1}$ strips, HIV-1 p55 only on HIV-1$_{UCD1}$, and FIV p10, p24, and p55 proteins, suggest that antibodies from #FH1 were reacting to evolutionarily retained epitopes on precursor Gag proteins and products. Antibody reactivities that cross lentiviral species have been reported (Matsuo et al., 1992; Olmsted et al., 1989a). Polyclonal rabbit antibodies to ruminant lentiviruses (caprine arthritis encephalitis virus, CAEV, and visna virus, VV) react to FIV major (p24) and minor (p10/17) core proteins on Western blot (Olmsted et al., 1989a). However, sera from FIV-infected cats have been reported to lack cross-reactive antibodies to HIV-1 and visa versa (Pedersen et al., 1987; Yamamoto et al., 1988b).

Upon determination of positive FIV serology and positive FIV gag nested RT-PCR of the subject #FH1, the source of the FIV infection was investigated. FIV was isolated and sequenced from the FIV-seropositive pet cat #FC1. FIV from cat #FC1 was readily isolated from PBMC by coculturing with Con-A-stimulated PBMC from an SPF cat, and the culture fluids were positive for FIV by RT assay. The cocultured cells were positive for FIV gag by both proviral PCR and RT-PCR. Control cultures consisting of cells from a SPF cat were negative by the same assays. Nested RT-PCR of plasma from Cat #FC1 also tested positive for FIV RNA gag. The ease in isolating FIV from PBMC and plasma suggests that the viral load in this cat was higher than subject #FH1. A comparison of the full gag sequences from subject #FH1=s human-human cocultured cells and her cat=s cat-cat cocultured cells revealed 99.6% nucleotide and 99.3% amino acid sequence homologies, demonstrating that this individual most likely contracted the FIV infection from her pet cat #FC1 (FIGS. 2A-2D). Based on sequence analysis at Gag/gag, sequence from Cat #FC1 belonged to FIV subtype B. Gag/gag sequences from Cat #FC1 had 83.1-94.2% nucleotide and 87.4-98.2% amino acid homology to subtype B FIV isolates (FIV$_{Aomori-1}$, FIV$_{Aomori-2}$, FIV$_{Sendai-2}$, FIV$_{Yokohama}$, FIV$_{TM2}$) but were clearly different from the FIV strains (<85.2% nucleotide and <88.6% amino acid homology) which were being produced in our laboratory (FIG. 4, amino acid sequences shown). Thus, the sequences derived from subject #FH1 and her cat, were not due to contamination from laboratory strains of FIV. These sequences had <55% nucleotide and amino acid sequence homologies to HIV-1, HIV-2, HTLV, SIV, EIAV, CAEV, VV, FeLV, and FeFV and were clearly distinct from the primate, ungulate, and other feline retroviruses (data not shown). Furthermore, BLAST analysis against NCBI/GenBank indicated that no known human protein sequences had any significant degree of homology to FIV Gag protein.

Since subject #FH2 has previously worked with HIV-1, she was tested for HIV-1 infection by PCR and HIV-1 antibodies by commercial HIV-1 Western blot analysis upon request by the subject. Based on standard HIV-1 Western blot analyses using Cambridge Biotech (20-hour serum incubation) and Bio-Rad Laboratories (30-minute serum incubation) tests, this subject was negative for HIV-1 antibodies. This finding was also confirmed by a licensed diagnostic laboratory. However, upon longer incubation period (20 hours) on Bio-Rad Western blot strip, faint antibody reactivity to p24 was observed repeatedly using serum collected from subject #FH2 on two different days in 2001 but slightly stronger reactivity to p24 was detected in serum collected after 1993. Both direct and coculture amplified PBMC from subject #FH2 were negative for HIV-1 by both PCR and RT-PCR with HIV-1 p24 ca primers. This result was confirmed by a licensed diagnostic laboratory using RT-PCR (Roche Amplicore HIV-1 Monitor Test). Sera from #FH2 were next tested for the presence of antibodies to FIV proteins. The more recent sera were strongly positive for antibodies reactive to FIV p10, p24, and p65 (potential FIV RT protein) and weakly positive for antibodies reactive to FIV p55 by Western blot analysis (FIGS. 1A-D). Her sera from 1993, collected before her participation in HIV research, reacted weakly to p55 of FIV-Petaluma (FIV$_{Pet}$), FIV-Shizuoka (FIV$_{Shi}$) and FIV-Bangston (FIV$_{Bang}$) and reacted strongly to all FIV p24 and p10. This observation together with our Gag/gag sequence results suggests that this subject is actively or defectively infected with FIV. In order to determine the source of FIV infection, her pet cat #FC2 was tested for FIV. Cat #FC2 was negative for FIV infection by RT and PCR and for FIV antibodies by Western blot analysis suggesting that her previous pet cat was more likely the source of FIV infection. This observation further indicates that subject #FH2 has been infected with FIV for at least 3 years since her previous pet cat died 3 years ago and possibly as long as 7.5 years since her serum from 1993 also reacted to FIV proteins and to HIV-1 p24 and p55.

Figures 5A, 5B:
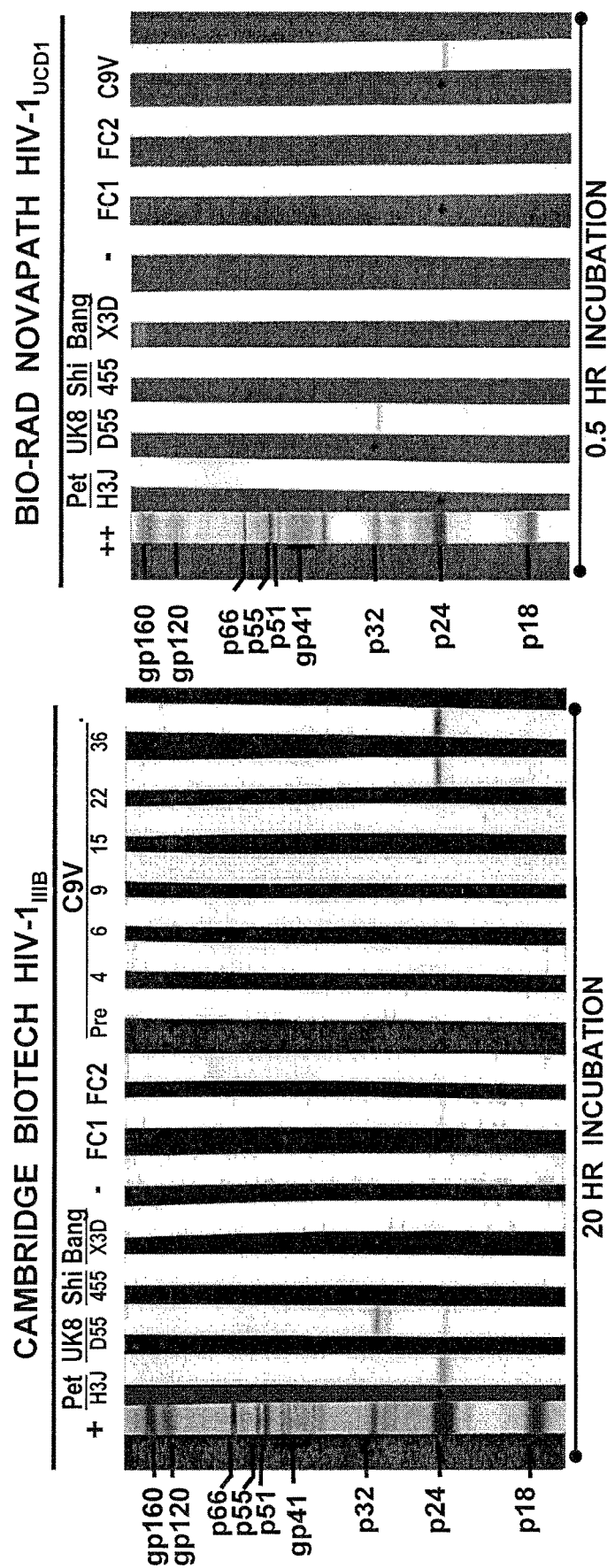

To determine if sera from FIV-infected cats can cross-react with HIV-1, HIV-1 Western blot analyses were performed on sera from SPF cats experimentally infected for prolonged period of time with four FIV strains currently being produced in our laboratory (FIGS. 5A and 5B). Sera from pet cats #FC1 and #FC2 were also tested along with sera from a SPF cat and a SPF cat (#C9V) infected with $FIV_{FC1}$ isolated from pet Cat #FC1. Sera from cats infected with either $FIV_{Pet}$ (cat #H3J) or $FIV_{UK8}$ (cat #D55) reacted strongly to HIV-1 p24 or p32 (HIV-1 integrase), respectively on both Bio-Rad HIV-$1_{UCD1}$ and Cambridge Biotech HIV-$1_{IIIB}$ Western blots. In addition, serum from $FIV_{UK8}$-infected cat #D55 reacted weakly to p24 on Cambridge Biotech HIV-$1_{IIIB}$ strip. Sera from Cat #FC1 reacted weakly to p24 of both HIV-$1_{IIIB}$ and HIV-$1_{UCD1}$. However, cat #C9V infected with $FIV_{FC1}$ was strongly reactive to p24 of both HIV-1 strains. Hence, $FIV_{FC1}$ core sequence which has 99.3% amino acid homology to FIV sequence isolated from subject #FH1, can readily induce cross-reactive antibodies to HIV-1. In contrast, sera from cat #FC2 and cats infected with $FIV_{Shi}$ (cat #455) and $FIV_{Bang}$ (cat #X3D) were non-reactive to HIV-1 proteins on both HIV-1 Western blots. All FIV-infected laboratory cats and cat #FC1 were strongly positive for FIV antibodies (FIGS. 5C and 5D). Although the numbers of serum samples are small, it is interesting to note that not all long-term FIV-infected cats produced anti-FIV antibodies that cross-reacted with HIV-1 p24 and p32. Nevertheless, these initial results indicate that sera from certain FIV-infected cats as well as a human subject positive by nested RT-PCR for FIV p24 ca or gag sequences do react to HIV-1 p24 protein. Thus, infection with FIV in humans results in antibodies that cross-reacts to HIV-1 p24 and HIV-1 p32.

Example 2 B

FIV Antigens Induce Cross-Reactive Immunity to HIV-1

Vaccinated and Infected Animals: Specific-pathogen-free cats were obtained from the investigator=s SPF breeding colony or purchased from Liberty Research (Waverly, N.Y.) and Cedar River Laboratories (Mason City, Iowa). All SPF cats tested negative for toxoplasma, feline leukemia virus, and FIV before experimental infection. These cats were immunized at 2-6 weeks intervals with $FIV_{Pet}$ and $FIV_{Shi}$ vaccines at combined or single dose of 250-500 µg for whole virus vaccine and $2.5$-$5 \times 10^6$ cells for inactivated infected-cell vaccines and sera collected at 2-4 weeks post vaccination (Pu et al., 2001). SPF cats were inoculated intravenously with 10-100 median cat infectious doses ($CID_{50}$) of either in vitro-derived or in vivo-derived inoculum as previously described (Pu et al., 2001).

Immunoblot, ELISA, and VN Antibody Analyses: Commercial HIV-1 (BioRad, Hercules, Calif.; Cambridge Biotech, Rockville, Md.) and HTLV-I and II (Cambridge Biotech) immunoblot strips were performed at 1:100 serum dilution using the methods described in the kits except for the anti-cat reagents and for the absorption/competition studies. Alkaline-phosphatase conjugated goat anti-cat IgG (Chemicon, Temecula, Calif.) at 0.3 µg/ml and biotinlylated anti-cat IgG (Vector, Burlingame, Calif.) at 0.4 µg/ml were used in place of the anti-human reagents for testing feline serum. ELISA assays were developed using commercial recombinant HIV-$1_{IIIB}$ gp160 (Chemicon), HIV-$1_{BRU}$ p24 (Biodesign, Kennebunk, Me.), and FIV p24 (Fort Dodge, Fort Dodge, Iowa) using a method as previously described (Yamamoto et al., 1993) with the following modifications. HIV-1 p24 and gp160 were coated on the plate at 300 and 150 ng/well, respectively. FIV 24 was coated at 50 ng/well. All samples for ELISA were performed in triplicates. The HIV VN antibody assay will be identical to the FIV VN antibody assay with the exception of SEA-stimulated human PBMC as indicator cells and HIV-$1_{LAV}$ (20 $TCID_{50}$) or HIV-$1_{UCD1}$ (0.1-50 $TCID_{50}$) as inocula (Pu et al., 2001; Yamamoto et al., 1993).

Absorption and Competition with Viral Antigens: Cat sera were absorbed three times for 1 hr each with either $2 \times 10^8$ infected or uninfected cells followed by competition with 250 µg of UV-inactivated virus or cell lysate directly on the immunoblot strips with the serum for 2 hr and the immunoblots were developed as before. FIV-infected ($FIV_{Shi}$-infected FeT-J and $FIV_{Bang}$-infected FeT-J cell combination), HIV-infected (HIV-$1_{UCD1}$ infected HuT-78 and HIV-$1_{LAV}$ infected H9 cell combination) and uninfected (FeT-J alone or HuT-78/H9 combination) cells were inactivated by 0.6% paraformaldehyde. HIV-infected cells were also UV-inactivated before paraformaldehyde treatment. IgG levels of the cell-absorbed and unabsorbed mock sera were determined by commercial feline IgG radial-immunodiffusion assay (Bethyl Laboratory, Montgomery, Tex.).

Cellular Immune Response: Virus-specific cellular immune responses of PBMC from vaccinated cats were determined by measuring the amount of interferon-γ produced in response to 10 µg/ml of recombinant FIV p24, HIV-$1_{BRU}$ p24, and HIV-$1_{IIIB}$ gp160 using the method previously described (Pu et al., 1999). In addition, cells stimulated with uninfected cell lysate (20 µg/ml), SEA (0.2 µg/ml, positive control), media diluent (negative control), and purified whole $FIV_{Pet}$ and $FIV_{Shi}$ (20 µg/ml) were also included as additional controls.

Figure 6A:
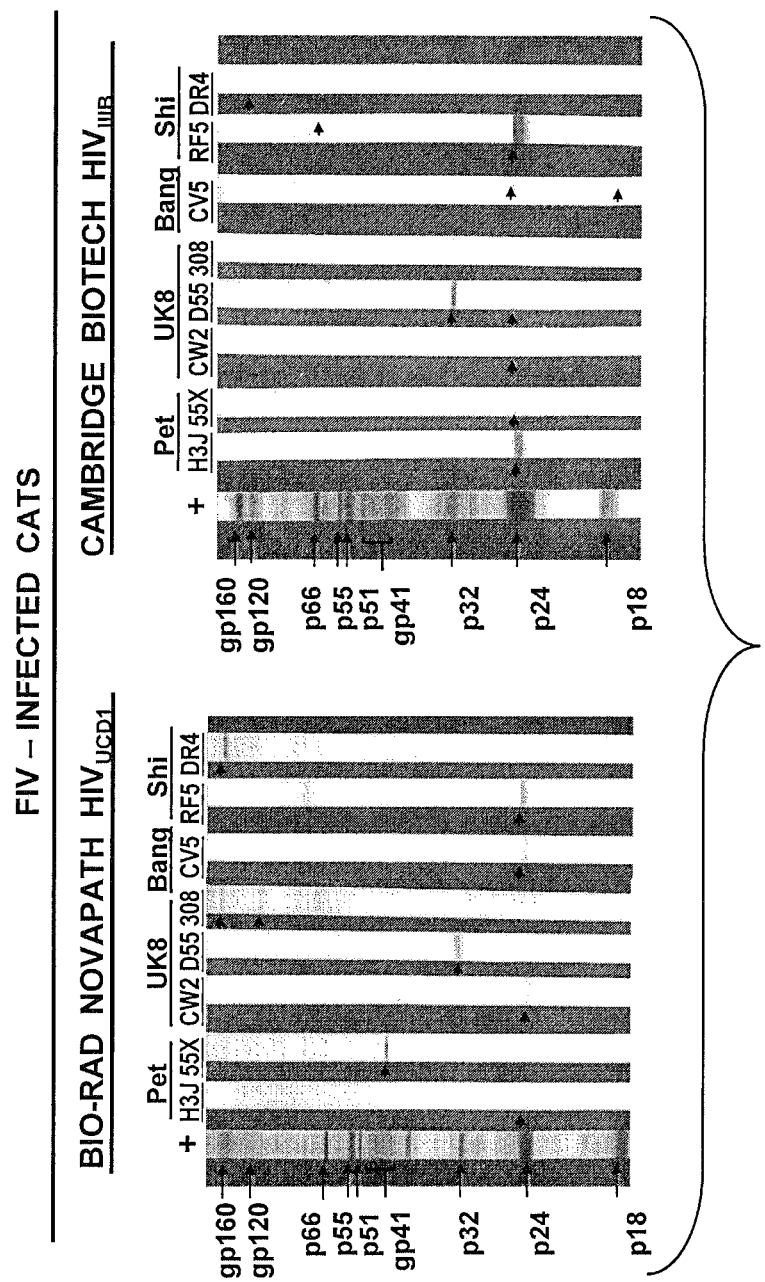
FIGS. 6A-6C show HIV-1 and HTLV-1/2 immunoblot analysis of FIV-infected and FIV-vaccinated cat sera. Sera from FIV-infected cats and FIV-vaccinated cats were tested for cross-reactive antibodies to HIV-1 with BioRad Novapath $HIV-1_{UCD1}$ and Cambridge Biotech $HIV-1_{IIIB}$ immunoblot kits (FIGS. 6A & 6B) and to HTLV-1/2 with Cambridge Biotech HTLV-1/2 immunoblot kit (FIG. 6C). Selected cat sera with unique banding patterns are shown to demonstrate the presence of cross-reactive antibodies with various patterns of reactivity to HIV-1 proteins. Serum samples of these cats before FIV inoculation were negative by both HIV-1 and HTLV-1/2 immunoblot analyses (data not shown).

Antibodies to FIV were developed in specific pathogen free (SPF) cats by either active infection with FIV strains or immunization with inactivated FIV vaccines. Sera from 41 FIV-infected cats at different time post-FIV inoculation were evaluated on BioRad HIV-$1_{UCD1}$ and Cambridge Biotech HIV-$1_{IIIB}$ immunoblots (Table 1, FIG. 6A). Overall, 18 of 41 (44%) infected cats had antibodies to HIV-1 core capsid p24, matrix p18, Gag p55, intergrase p32, transmembrane envelope gp41, surface envelope gp120 or precursor envelope gp160 (Table 1, FIG. 6A) with greatest reactivity to p24. Three of 10 cats infected with $FIV_{Pet}$ (subtype A), 7 of 11 cats infected with $FIV_{UK8}$ (subtype A), 5 of 11 cats infected with $FIV_{Bang}$ (subtype $A_{gag}/B_{env}$), and 3 of 9 cats infected with $FIV_{Shi}$ (subtype D) had cross-reactive antibodies to HIV-1. The majority of the cats (64%) infected with $FIV_{UK8}$ developed cross-reactive antibodies to HIV-1, while only three cats (30%) infected with $FIV_{Pet}$ developed cross-reactive antibodies to HIV-1. Both of these strains are subtype A FIV strains. Hence, strain specific cross-reactivity to HIV-1 may exist.

Figure 6B:
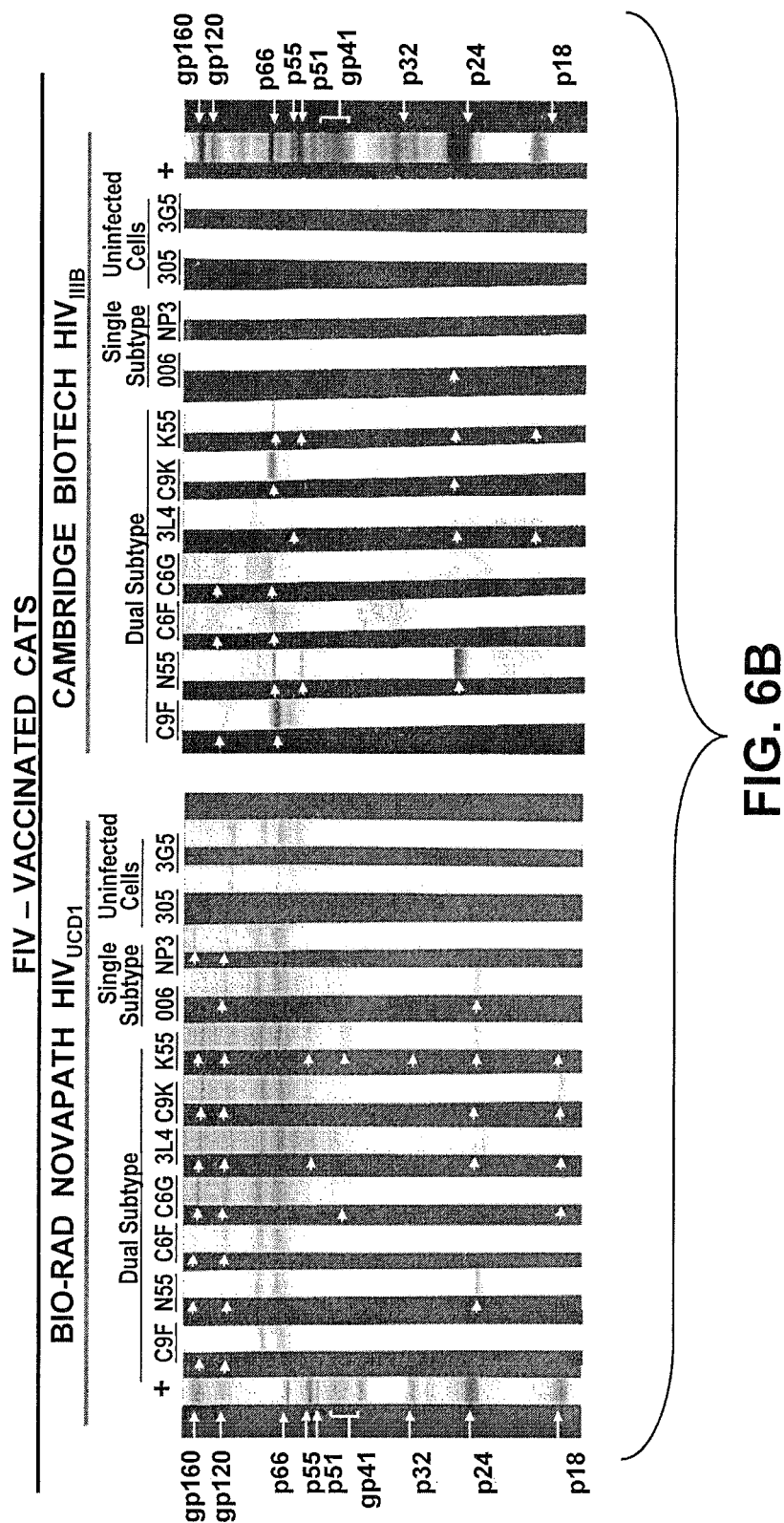
Figure 6C:
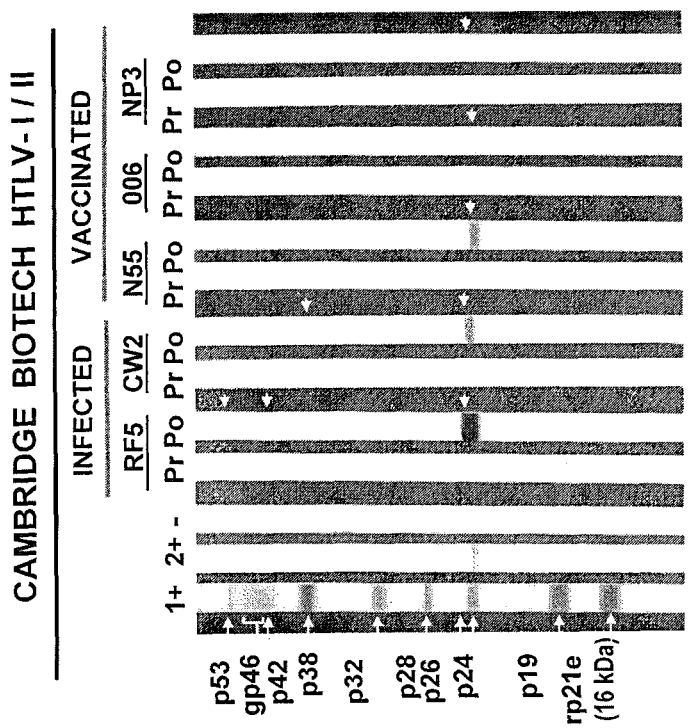

Similarly, sera from FIV-vaccinated cats were tested on BioRad HIV-$1_{UCD1}$ and Cambridge HIV-$1_{IIIB}$ immunoblots (Table 1, FIG. 6B). The vaccinated cat sera had greater reactivity and recognized more HIV-1 proteins than did sera from infected cats. Sera that reacted with HIV-$1_{IIIB}$ p24 consistently reacted to HIV-$1_{UCD1}$ p24 but not vice versa. Cross-reactivity to HIV-1 envelope products was observed mostly with HIV-$1_{UCD1}$ rather than HIV-$1_{IIIB}$. In contrast, sera reactive to HIV-1 polymerases p51 and p66 reacted to the viral polymerases from only HIV-$1_{IIIB}$. HIV-$1_{IIIB}$ and HIV-$1_{UCD1}$ are subtype B isolates that were produced in human H9 and HuT-78 cells, respectively. HIV-1$_{IIIB}$ and HIV-1$_{UCD1}$ has 97% amino acid sequence homology at p24 and 85% amino acid sequence homology at Env. Thus, the specificity of the cross-reactivity appears to differ based on the HIV-1 strain at polymerases and Env. Six FIV-infected and six FIV-vaccinated cats that reacted to HIV-1 immunoblot were tested against HTLV-I/II using Cambridge HTLV-I/II Western Blot Kit. Three vaccinated and two infected cats had cross-reactive antibodies to HTLV-I/II core p24 (FIG. 6C). One of the infected cat also had antibodies weakly reactive to HTLV Tax p38, while the other infected cat also had antibodies weakly reactive to HTLV precursor Gag p53 and Gag intermediate p42. As previously reported for lentiviruses (Olmsted et al., 1989a; Matsuo et al. 1992; Goudsmit et al., 1986), core sequences appear to be evolutionarily conserved even between retrovirus families (Egberink et al., 1991).

Figure 7A:
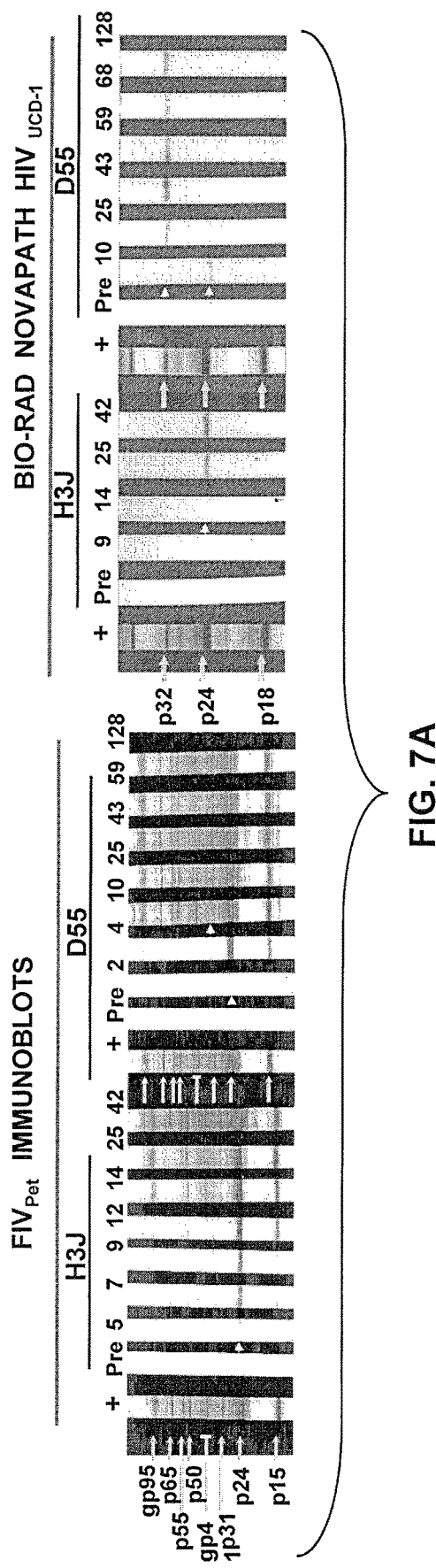
Figure 7B:
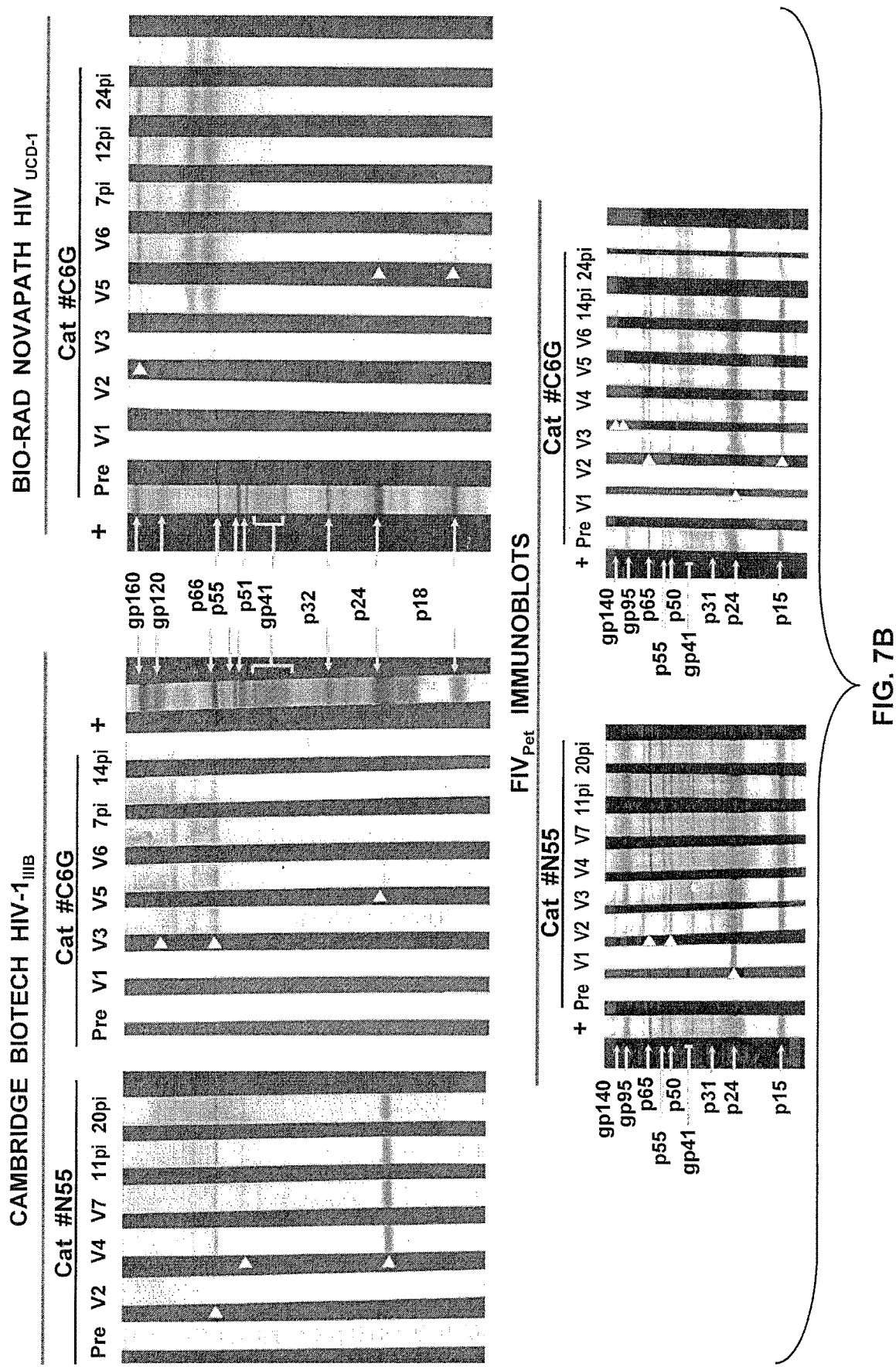

Since the post-infection sera that were tested were not necessarily collected at the optimal time for the presence of cross-reactivity antibodies to HIV-1, a study was performed using cat sera from different times post FIV infection (pi) (FIG. 7A). Cross-reactive antibodies to HIV-1 were detected in sera from all five cats at relatively early stage of FIV infection (10-14 wk pi), at which time only 1-2 bands developed (predominantly HIV-1 p24 protein), and persisted for a long-time. Comparing HIV and FIV immunoblots with sera from the same time points, antibodies that recognized FIV proteins developed earlier (2-6 wk pi) and reacted persistently at higher titers and to a broad spectrum of FIV proteins (FIG. 7A). Furthermore, FIV antibodies from infected cats that were negative for HIV-1 cross-reactivity were negative throughout 6-120 wk pi (data not shown). The temporal development of the cross-reactive antibodies to HIV-1 in FIV vaccine sera was next determined (FIG. 7B). The cross-reactive antibodies developed as early as second vaccination and persisted for a prolonged period of time. Similar to anti-p24 antibodies in the infected cat sera, the antibodies reactive to FIV p24 developed much earlier than those cross-reactive with HIV-1 p24 (FIGS. 7A and 7B). However, unlike the cross-reactive anti-p24 antibodies that developed before other reactive antibodies in the infected cat sera, the cross-reactive anti-p24 antibodies in the vaccinated cat sera were detected after the development of cross-reactive antibodies to Env (gp120, gp160) and polymerase (p66).

Figure 8A:
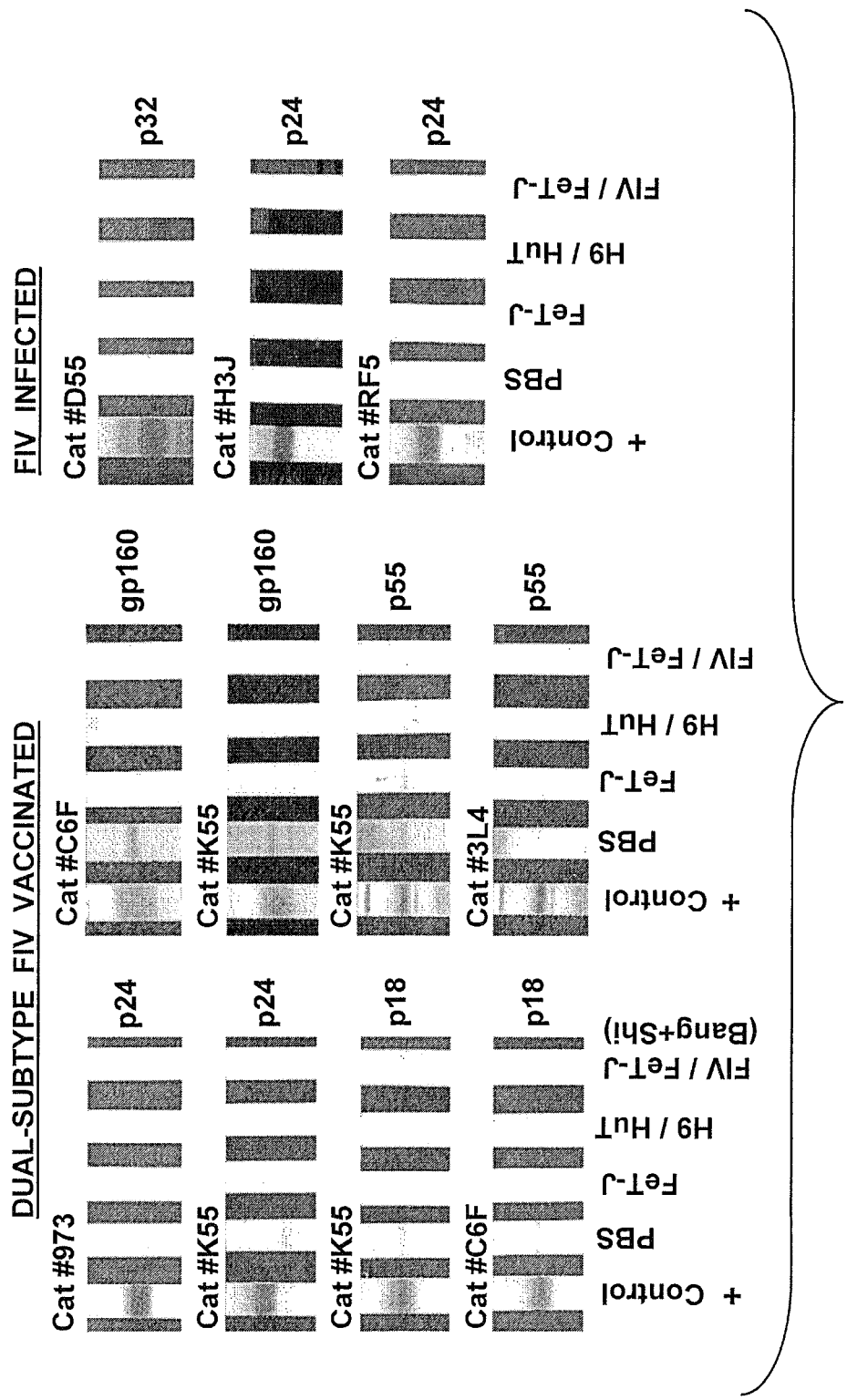
FIGS. 8A-8D show absorption of cat sera with viral antigens.
Figure 8B:
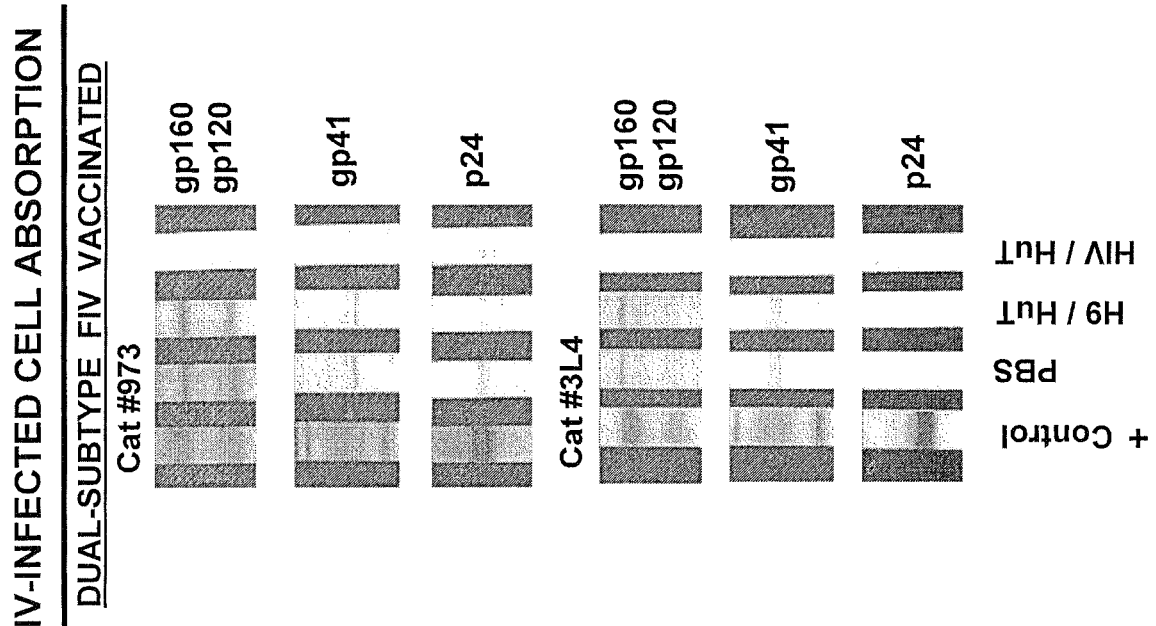
Figure 8D:
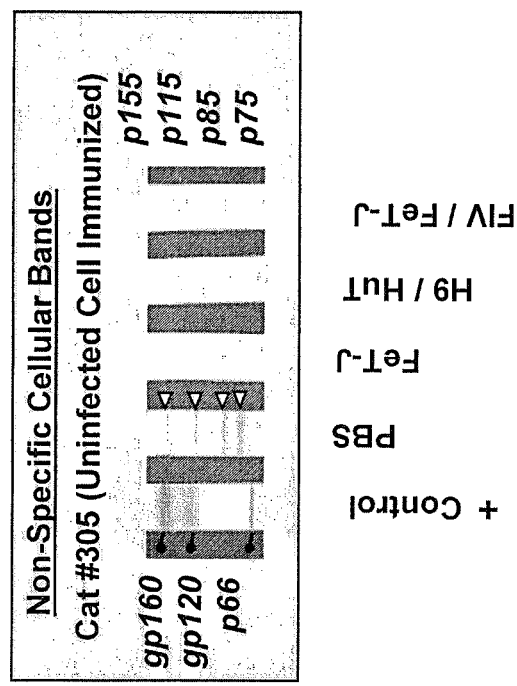
Figure 8C:
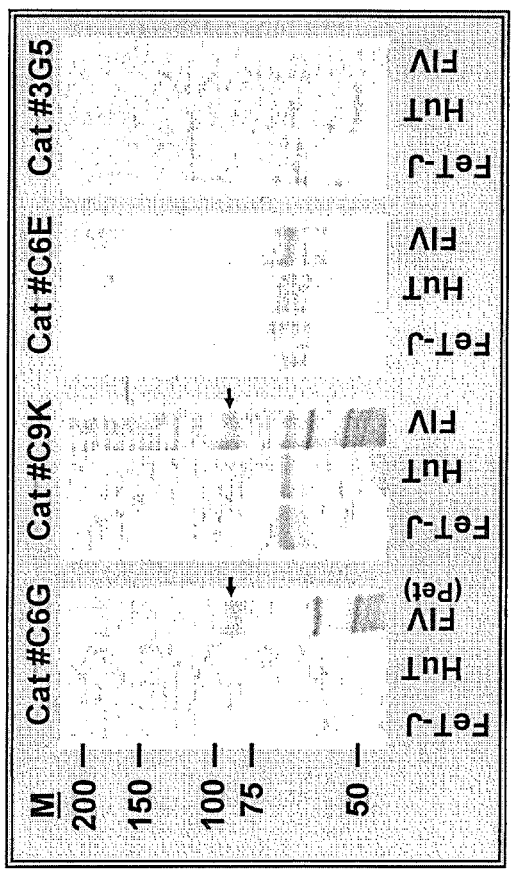
Figure 9A:
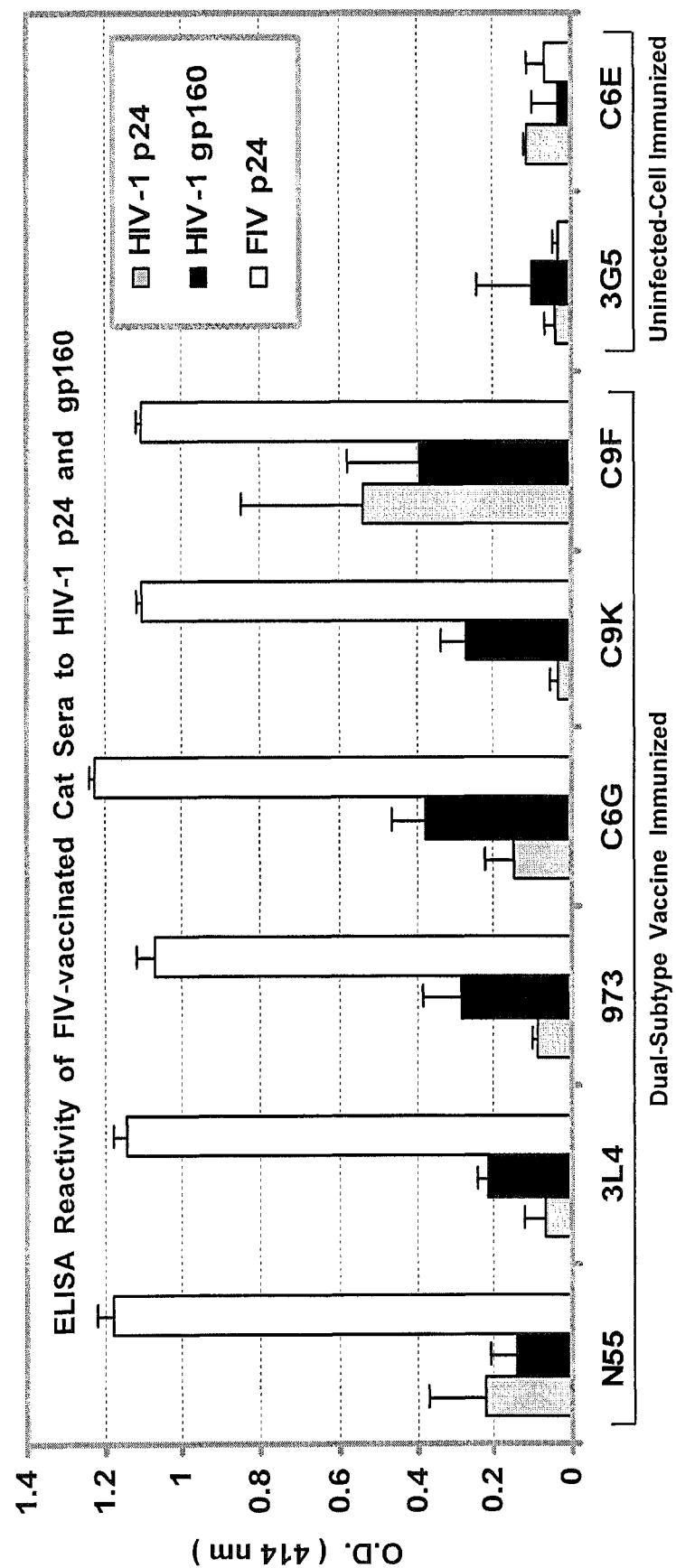
FIGS. 9A and 9B show reactivity of FIV-vaccinated cat sera and PBMC to HIV p24 and gp160.

In order to negate nonspecific reactivity caused by cellular antigens, selected sera from FIV-vaccinated and FIV-infected cats were preabsorbed extensively with either uninfected feline FeT-J cells or FIV-infected FeT-J cells. The dual-subtype vaccine viruses were produced in FeT-J cells or a cell line from FeT-J lineage (FL-4 cells) (Pu et al., 2001). Those sera preabsorbed with uninfected cells were then competed with uninfected FeT-J cell lysate, while those preabsorbed with FIV-infected FeT-J cells were competed with pelleted FIV preparation. The cross-reactivity with HIV-1 p24, p18, p32, gp41, gp120, gp160, and polymerase p51/p66 were not removed in HIV-1 immunoblots by uninfected cell absorption/competition but were completely removed by FIV-infected cell absorption/competition, demonstrating that the FIV-specific antibodies were reacting specifically with HIV-1 proteins (FIG. 8A). As an additional precaution, a separate set of these cat sera (cats #973 and #3L4) were preabsorbed with either uninfected human cells (H9/HuT-78 combination) or HIV-1-infected human T cells (HIV$_{LAV}$/H9 and HIV$_{UCD1}$/HuT-78 combination). Only preabsorption with HIV-1 infected cells was able to remove HIV-1 cross-reactivity from the FIV-specific sera (FIG. 8B). As an additional confirmation that FIV-specific sera cross-react with HIV-1, these cat sera were evaluated in ELISA for reactivity with recombinant HIV-1$_{BRU}$ p24 and recombinant HIV-1$_{IIIB}$ gp160. Both vaccinated cat sera and post-infection sera clearly cross-reacted with HIV-1$_{BRU}$ p24 and HIV-1$_{IIIB}$ gp160 (FIG. 9A). These results further confirm that the HIV-1 cross-reactivity of FIV-specific cat sera is reacting specifically to HIV-1 protein(s).

As a means of evaluating the importance of cross-reactive antibodies to HIV-1, reactive sera from dual-subtype vaccinated cats were tested for the presence of FIV and HIV-1 neutralizing antibody titers. The dual-subtype FIV vaccine has been shown to induce VN antibodies to homologous and heterologous FIV strains (Pu et al., 2001). Sera from six vaccinated cats (Cats #N55, #973, #C6G, #3L4, #C9K, and #C9F) with strong cross-reactive antibodies to HIV-1 Env were tested in a VN assay using human peripheral blood mononuclear cells (PBMC) as indicator cells and HIV-1$_{LAV}$ or HIV-1$_{UCD1}$ as inocula (Table 2). Controls included pooled serum from two HIV-1 positive individuals, serum from an HIV-negative individual, and sera from SPF cats immunized with uninfected FeT-J cells (Cat #3G5) or Fet-J lysates (Cat #C6E). Both proviral PCR levels and RT activity were used to detect HIV-1 levels in the antibody-treated cultures. One (Cat #C6G) of six vaccine sera tested positive for VN antibodies to HIV-1$_{LAV}$ (50 VN titer) and to HIV-1$_{UCD1}$ (10 VN titer). This sera was the strongest one of the four sera (Cats #C6G, #973, #C9K, and #C9F) that also reacted in the Cambridge HIV-1$_{IIIB}$ immunoblot at gp120 (Table 2, FIGS. 6B and 7B). These results are indicative of the importance of evolutionarily conserved epitopes in generating cross-reactive and neutralizing antibodies to HIV-1 Env.

Figure 9B:
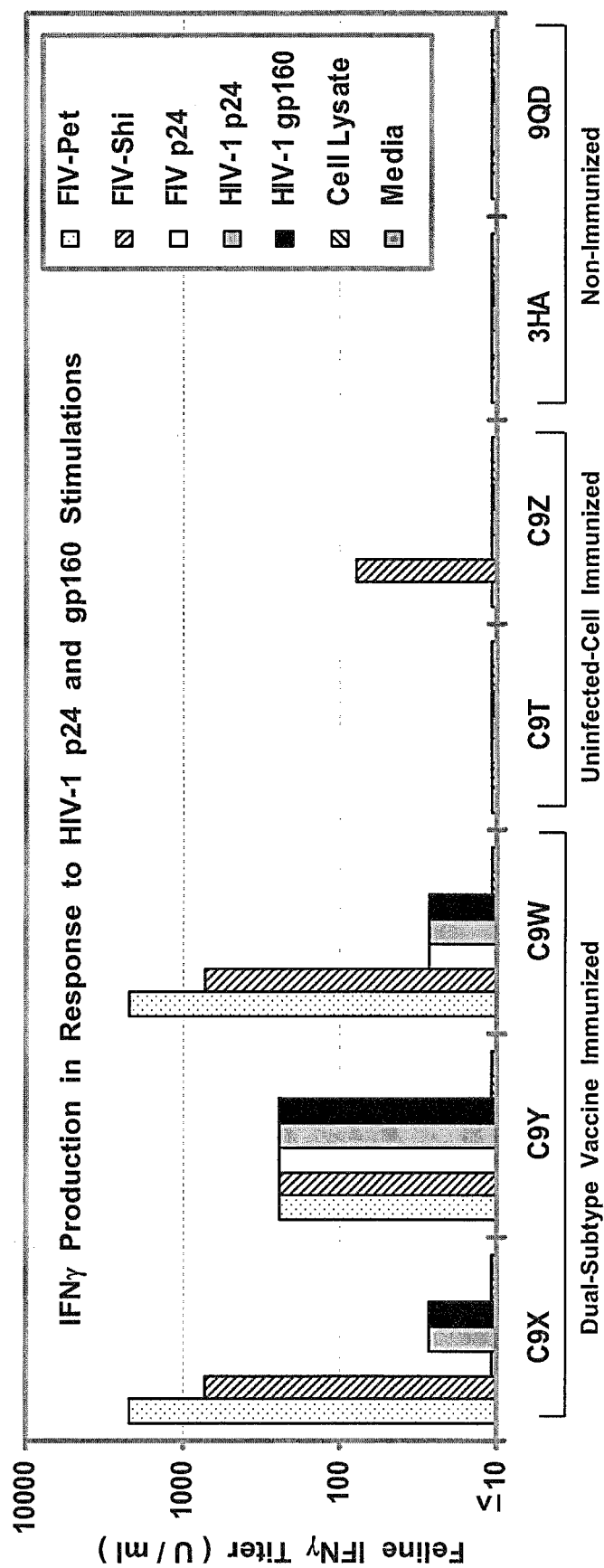

Since FIV-specific antibodies react to recombinant HIV-1 p24 protein, it is conceivable that this protein has epitopes for stimulating the necessary cellular immune components such as cytokines needed to develop these cross-reactive antibodies. The ability of FIV/HIV-1 evolutionarily conserved epitopes to generate cellular immunity was evaluated. In previous studies, PBMC from dual-subtype FIV vaccinated cats produced high levels of interferon-γ (IFNγ) production upon stimulation with inactivated whole FIV antigens (Pu et al., 2001; Pu et al. 1999). IFNγ is a TH1 cytokine that is also essential in the production of IgG (Abbas et al., 2000). Thus, the ability of PBMC from dual-subtype vaccinated cats to produce IFNγ in response to either HIV-1$_{BRU}$ p24, FIV p24, or inactivated whole FIV stimulations was evaluated (FIG. 9B). Equivalent amounts of uninfected FeT-J cells were used as nonspecific control stimulants, while Staphylococcal enterotoxin A (SEA, 1 µg/ml) was used as positive control stimulant. Significant titers of IFNγ (243-2187 U/ml) were detected upon stimulation with inactivated whole FIV$_{Pet}$ and FIV$_{Shi}$ in all vaccinated cats (FIG. 9B). In contrast, IFNγ production in response to stimulation with FIV or HIV p24 proteins was low in two vaccinated cats (#C9X and #C9W) but significant in Cat #C9Y (256 U/ml).

Example 3

Partial gag Sequence Analysis Following Real-Time PCR

Partial FIV gag were isolated from cocultures of #FH1 PBMC with either human PBMC (B4) or feline PBMC (A9)

using Real-time PCR followed by regular PCR. Positive PCR products after Real-time PCR were used as samples for regular PCR. All the primers and probe for Real-time PCR and regular PCR were described in Norway et al. (2001). After regular PCR, amplification products of the expected size were isolated from agarose gel and cloned into the pCR 2.1 TOPO cloning vector according to the manufacturer=s instructions (Invitrogen, Carlsbad, Calif.) and sequenced (ICBR core lab, UF) (FIG. 10). These results confirm the presence of FIV sequences in the #FH1 subject=s cells. The conditions under which the assay was performed minimized any possibility of cross-contamination.

Example 4

Vaccines

Vaccines compositions of the present invention comprising FIV proteins and peptides, recombinant viral vector-based FIV constructs, attenuated or inactivated FIV viral isolates, and the like, having antigenic or immunogenic properties, can be prepared by procedures well known in the art. For example, such vaccines can be prepared as injectables, e.g., liquid solutions or suspensions. Solid forms for solution in, or suspension in, a liquid prior to injection also can be prepared. Optionally, the preparation also can be emulsified. The active antigenic ingredient or ingredients can be mixed with excipients which are pharmaceutically acceptable and compatible with the active ingredient. Examples of suitable excipients are water, saline, dextrose, glycerol, ethanol, or the like, and combinations thereof. In addition, if desired, the vaccine can contain minor amounts of auxiliary substances such as wetting or emulsifying agents, pH buffering agents, or adjuvants such as aluminum hydroxide or muramyl dipeptide or variations thereof. Also, cholera toxin subunit B or other agents which stimulate antibody production at mucosal sites can be used. In the case of peptides, coupling to larger molecules such as KLH or tetanus toxoid sometimes enhances immunogenicity. The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers include, for example, polyalkalene glycols or triglycerides. Suppositories can be formed from mixtures containing the active ingredient in the range of about 0.5% to about 10%, preferably about 1 to about 2%. Oral formulations can include such normally employed excipients as, for example, pharmaceutical grades of mannitol, lactose, starch, magnesium stearate, sodium saccharine, cellulose, magnesium carbonate, and the like. These compositions can take the form of solutions, suspensions, tablets, pills, capsules, sustained release formulations or powders and contain from about 10% to about 95% of active ingredient, preferably from about 25% to about 70%.

Compositions can be formulated into the vaccine as neutral or salt forms. Pharmaceutically acceptable salts include the acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered can depend on the subject to be treated and the degree of protection desired. Precise amounts of active ingredient required to be administered depend on the judgment of the practitioner and can be peculiar to each individual. However, suitable dosage ranges are of the order of about several hundred micrograms active ingredient per individual. Suitable regimes for initial administration and booster shots are also variable, but are typified by an initial administration followed in one or two week intervals by a subsequent injection or other administration.

It should be understood that the examples and embodiments described herein are for illustrative purposes only and that various modifications or changes in light thereof will be suggested to persons skilled in the art and are to be included within the spirit and purview of this application and the scope of the appended claims.

TABLE 1

HIV-1 IMMUNOBLOT REACTIVITY OF FIV-INFECTED AND FIV-VACCINATED CAT SERA[a]

| | Vaccinated Cat Sera | | Infected Cat Sera[a] | | | | |
|---|---|---|---|---|---|---|---|
| | Dual | Single | | | | | |
| Viral Protein | Subtype | Subtype | FIV | Pet | UK8 | Bang | Shi |
| Total Tested | 13 | 12 | 41 | 10 | 11 | 11 | 9 |
| Total Positive | 13 | 11 | 18 | 3 | 7 | 5 | 3 |
| % Positive | 100% | 92% | 44% | 30% | 64% | 45% | 33% |
| p24 | 11 | 6 | 16 | 1 | 7 | 5 | 3 |
| p18 | 8 | 1 | 2 | 0 | 1 | 1 | 0 |
| p55 | 2 | 0 | 4 | 0 | 1 | 1 | 2 |
| p32 | 3 | 0 | 2 | 0 | 2 | 0 | 0 |
| p51 | 2 | 1 | 0 | 0 | 0 | 0 | 0 |
| p66 | 9 | 8 | 2 | 1 | 0 | 0 | 1 |
| gp41 | 6 | 3 | 4 | 1 | 0 | 1 | 2 |
| gp120 | 5 | 4 | 2 | 1 | 1 | 0 | 0 |
| gp160 | 1 | 0 | 1 | 0 | 1 | 0 | 0 |

[a]Nine of 19 (47%) cats infected with in vitro-derived inocula and 9 of 22 (41%) cats infected with in vivo-derived inocula developed antibodies to HIV-1. Hence, both in vitro and in vivo-derived inocula were equally effective at inducing cross-reactive antibodies to HIV-1. Inoculation dose (10-100 CID$_{50}$) had no statistically significant effect on the frequency or level of HIV cross-reactivity (individual data not shown). Except for the antibodies to gp120 and gp160, a serum was considered antibody positive for specific HIV protein if it was positive on either HIV-1$_{IIIB}$ or HIV-1$_{UCD1}$ immunoblot analysis. A serum was considered positive for either gp120 or gp160 if it was positive on both HIV-1$_{IIIB}$ and HIV-1$_{UCD1}$ immunoblot analyses. Thirteen of 13 dual-subtype vaccinated and 11 of 12 single-subtype vaccinated had either antibodies to gp120 or gp160 in HIV-1$_{UCD1}$ immunoblot analysis (data not shown). Data from a stricter analysis are shown for envelope antibodies because of the presence of antibodies to cellular proteins that reacted close to but clearly different from gp120 and gp160.

TABLE 2

SUMMARY OF THE SERUM VN TITERS AND SERUM REACTIVITY TO VIRAL ENV

| CAT # (TYPE OF IMMUNIZATION) | HIV-1 IMMUNOBLOT (gp120/gp160) | | HIV-1$_{IIIB}$ gp160 ELISA TITER | VN ANTIBODY TITER TO | | | | |
|---|---|---|---|---|---|---|---|---|
| | | | | HIV-1 | | FIV | | |
| | UCD1 | IIIB | | UCD1 | LAV | Pet | Bang | Shi |
| C6G (Virus Vaccine) | +/+ | +/− | >1200 | 10 | 50 | 50 | 50 | >500 |
| C9K (Virus Vaccine) | +/+ | +/− | 1200 | <5 | 5 | 50 | 5 | 500 |
| C9F (Virus Vaccine) | +/+ | +/− | 1200 | <5 | <5 | 5 | 5 | 500 |
| 3L4 (FIV-Cell Vaccine) | +/+ | −/− | 1200 | <5 | <5 | >1000 | >500 | <10 |
| N55 (FIV-Cell Vaccine) | +/+ | −/− | 600 | <5 | <5 | 100 | 500 | <10 |
| 973 (FIV-Cell Vaccine) | +/+ | +/− | >1200 | <5 | <5 | 100 | 50 | <10 |
| 3G5 (Uninfected Whole Cell) | −/− | −/− | <300 | <5 | <5 | <5 | <5 | <5 |
| C6E (Uninfected Cell Lysate) | −/− | −/− | <300 | <5 | <5 | <5 | <5 | <5 |
| Pooled HIV-Positive Serum | +/+ | +/+ | >1200 | >500 | 50 | 5 | 5 | 5 |
| HIV-Negative Serum | −/− | −/− | <300 | <5 | <5 | <5 | <5 | <5 |

REFERENCES

WO 99/60988
U.S. Pat. No. 4,358,535
U.S. Pat. No. 4,361,537
U.S. Pat. No. 4,683,195
U.S. Pat. No. 4,683,202
U.S. Pat. No. 4,708,818
U.S. Pat. No. 4,800,159
U.S. Pat. No. 4,861,720
U.S. Pat. No. 5,037,753
U.S. Pat. No. 5,055,391
U.S. Pat. No. 5,108,891
U.S. Pat. No. 5,118,602
U.S. Pat. No. 5,135,684
U.S. Pat. No. 5,160,701
U.S. Pat. No. 5,275,813
U.S. Pat. No. 5,510,106
U.S. Pat. No. 5,530,101
U.S. Pat. No. 5,565,319
U.S. Pat. No. 5,585,089
U.S. Pat. No. 5,693,762
U.S. Pat. No. 5,807,715
U.S. Pat. No. 5,846,825
U.S. Pat. No. 5,922,533
Abbas, A. K. et al. (2000) *Cellular and Molecular Immunology*, 4th edition, pp. 196-199 (WB Saunders Co., Philadelphia).
Ackley, C. D., J. K. Yamamoto, N. B. Levy, N. C. Pedersen, M. D. Cooper (1990) A Immunologic Abnormalities in Pathogen-free Cats Experimentally Infected with Feline Immunodeficiency Virus, @ *J. Virol.* 64:5652-5655.
Azocar, J., M. Essex (1979) A Susceptibility of Human Cell Lines to Feline Leukemia Virus and Feline Sarcoma Virus, @ *J. Natl Cancer Inst* 63:1179-1184.
Butera, S. T., J. Brown, M. E. Callahan, S. M. Owen, A. L. Matthews, D. D. Weigner, L. E. Chapman, P. A. Sandstrom (2000) A Survey of Veterinary Conference Attendees for Evidence of Zoonotic Infection by Feline Retroviruses@ *J Am Vet Med Assoc.* 217(10):1475-1479.
Division of AIDS, STD, TB Laboratory Research, CDC. CDC report: HIV and Retrovirology, Division of AIDS, STD, and TB Laboratory Research, CDC. www.cdc.gov/ncidod/dastlr/Retrovirology/default.htm. Gaskell, R M and Bennett M Feline and Canine Infectious Diseases (Sutton J. B., Ed), Blackwell Science, Cambridge.
Egberink, H. F. et al. (1991) A Use of Western Blot and radioimmunoprecipitation for Diagnosis of Feline Leukemia and Feline Immunodeficiency Virus Infections@ *J Am Vet Med Assoc* 199:1339-1342.
Goudsmit, J. et al. (1986) A LAV/HTLV-III gag Gene Product p24 Shares Antigenic Determinants with Equine Infectious Amenia Virus but not with Visna Virus or Caprine Arthritis Encephalitis Virus@ *Intervirology* 26:169-173.
Hohdatsu, T. et al. (1998) A Genetic Subtyping and Epidemiological Study of Feline Immunodeficiency Virus by Nested Polymerase Chair Reaction-Restriction Fragment Length Polymorphism Analysis of the Gag Gene *J. Virol. Methods* 70:107-111.
Hosie, M. J., O. Jarrett (1990) A Serological Responses of Cats to Feline Immunodeficiency Virus@ *AIDS* 4:215-220.
Jarrett, O., H. M. Laird, D. Hay (1973) A Determinants of the Host Range of Feline Leukaemia Viruses, @ *J. Gen Virol* 20:169-175.
Johnston, J. C., M. Gasmi, L. E. Lim, J. H. Elder, J. K Yee, D. J. Jolly, K. P. Campbell, B. L. Davidson, S. L. Sauter (1999a) A Minimum Requirements for Efficient Transduction of Dividing and Nondividing Cells by Feline Immunodeficiency Virus Vectors@ *J Virol.* 73(6):4991-5000.
Johnston, J. et al. (1999b) A Productive Infection of Human Peripheral Blood Mononuclear Cells by Feline Immunodeficiency Virus: Implications for Vector Development@ *J Virol* 73:2491-2498.
Khabbaz, R. F., W. Heneine, J. R. George, B. Parekh, T. Rowe, T. Woods, W. M. Switzer, H. M. McClure, M. Murphey-Corb, T. M. Folks (1994) A Brief Report: Infection of a Laboratory Worker with a Simian Immunodeficiency Virus, @ *N. Engl. J. Med* 330:172-177.
Khabbaz, R. F., T. Rowe, M. Murphey-Corb, W. M. Heneine, C. A. Schable, J. R. George, C. P. Pau, B. S. Parekh, M. D. Lairmore, J. W. Curran, J. E. Kaplan, G. Schochetman, T. M. Folks (1992) A Simian Immunodeficiency Virus Needlestick Accident in a Laboratory Worker,@ *Lancet* 340:271-273.
Kakinuma, S., K. Motokawa, T. Hohdatsu, J. K. Yamamoto, H. Koyama, H. Hashimoto (1995) A Nucleotide Sequence of Feline Immunodeficiency Virus: Classification of Japanese Isolates into Two Subtypes Which Are Distinct from Non-Japanese Subtypes@ *Journal of Virology* 69(6):3639-3646.

Kohler and Milstein (1976) Eur. J. Immunol. 6:511-519.

Louwagie, J., F. E. McCutchan, M. Peeters, T. P. Brennan, E. Sanders-Buell, G. A. Eddy, G. van den Grosen, K. Fransen, G. M. Gershy-Damet, R. Deleys, D. S. Burke (1993) A Phylogenetic Analysis of gag Genes From 70 International HIV-1 Isolates Provides Evidence for Multiple Genotypes@ AIDS 7:769-780.

Matsuo, K, Y. Nishino, T. Kimura, R. Yamaguchi, A. Yamazaki, T. Mikami, K. Ikuta (1992) A Highly Conserved Epitope Domain in Major Core Protein p24 is Structurally Similar Among Human, Simian and Feline Immunodeficiency Viruses@ J Gen Virol. 73(Pt 9):2445-2450.

Merrifield, R. B. (1963) "Solid Phase Peptide Synthesis. I. The Synthesis of a Tetrapeptide" J. Amer. Chem. Soc. 85:2149-2156.

Morrison, et al. (1984) A Chimeric Human Antibody Molecules: Mouse Antigen-binding Domains with Human Constant Region Domains@ PNAS USA 81:6851-6855.

Murphy, F., D. W. Kingsbury (1990) A Virus Taxonomy@ In Fields Virology, 2nd Ed., B. N. Fields, D. M. Knipe et al., eds, Raven Press, New York, Chapter 2, pp. 9-36.

Norway, R. M. et al. (2001) A Thymic Lesions in Cats Infected with a Pathogenic Molecular Clone or an ORT-A/2-deficient Molecular Clone of Feline Immunodeficiency Virus@ J Virol 75:5833-5841.

Olmsted, R. A., A. K. Barnes, J. K. Yamamoto, V. M. Hirsch, R. H. Purcell, P. R. Johnson (1989a) A Molecular Cloning of Feline Immunodeficiency Virus@ Proc. Nat. Acad. Sci. 86:2448-2452.

Olmsted, R. A., V. M. Hirsch, R. H. Purcell, P. R. Johnson (1989b) A Nucleotide Sequence Analysis of Feline Immunodeficiency Virus: Genome Organization and Relationship to Other Lentivirus @ Proc. Natl. Acad. Sci. USA 86:8088-8092.

Ou, C. Y. et al. (1988) A DNA Amplification for Direct Detection of HIV-1 in DNA of Peripheral Blood Mononuclear Cells@ Science 239:295-297.

Pedersen, N. C., E. W. Ho, M. L. Brown, J. K. Yamamoto (1987) A Isolation of a T-lymphotropic Virus From Domestic Cats with an Immunodeficiency-like Syndrome@ Science 235:790-793.

Poeschla, E. M., D. J. Looney (1998) A CXCR4 is Required by a Nonprimate Lentivirus: Heterologous Expression of Feline Immunodeficiency Virus in Human, Rodent, and Feline Cells@ J. Virol. 72:6858-6866.

Pu, R. et al. (1999) A MHC-restricted Protection of Cats Against FIV Infection by Adoptive Transfer of Immune Cells from FIV-vaccinated Donors@ Cell Immunol 198:30-43.

Pu, R. et al. (2001) A Dual-subtype FIV Vaccine Protects Cats Against In Vivo Swarms of Both Homologous and Heterologous Subtype FIV Isolates@ AIDS 15:1225-1237.

Richardson, J., G. Pancino, R. Merat, T. Leste-Lasserre, A. Moraillon, J. Schneider-Mergenner, M. Alizon, P. Sonigo, N. Heveke (1999) A Shared Usage of the Chemokine Receptor CXCR4 by Primary and Laboratory-adapted Strains of Feline Immunodeficiency Virus@ J. Virol. 73:3661-3671.

Rigby, M. A., E. C. Holmes, M. Pistello, A. Mackay, A. J. Leigh-Brown, J. C. Neil (1993) A Evolution of Structural Proteins of Feline Immunodeficiency Virus: Molecular Epidemiology and Evidence of Selection for Change@ J. Gen. Virol. 74:425-436.

Saiki, Randall K., Stephen Scharf, Fred Faloona, Kary B. Mullis, Glenn T. Horn, Henry A. Erlich, Norman Arnheim (1985) A Enzymatic Amplification of β-Globin Genomic Sequences and Restriction Site Analysis for Diagnosis of Sickle Cell Anemia@ Science 230:1350-1354.

Sarma, P. S., R. J. Huebner, J. F. Basker, L. Vernon, R. V. Gilden (1970) A Feline Leukemia and Sarcoma Viruses: Susceptibility of Human Cells to Infection, @ Science 168:1098-1100.

Sodora, D. L., E. G. Shpaer, B. E. Kitchell, S. W. Dow, E. A. Hoover, J. I. Mullins (1994) A Identification of Three Feline Immunodeficiency Virus (FIV) env Gene Subtype and Comparison of the FIV and Human Immunodeficiency Virus Type 1 Evolutionary Patterns@ J. Virol. 68:2230-2238.

Talbott, R. L., E. E. Sparger, K. M. Lovelace, W. M. Fitch, N. C. Pedersen, P. A. Luciw, J. H. Elder (1989) A Nucleotide Sequence and Genomic Organization of Feline Immunodeficiency Virus@ Proc. Natl. Acad. Sci. USA 86:5743-5747.

Willett, B. J., L. Picard, M. J. Hosie, J. D. Turner, K. Adema, P. R. Clapham (1997a) A Shared Usage of the Chemokine Receptor CXCR4 by the Feline and Human Immunodeficiency Viruses@ J. Virol. 71:6407-6415.

Willett, B. J., M. J. Hosie, J. C. Neil, J. D. Turner, J. A. Hoxie (1997b) A Common Mechanism of Infection by Lentiviruses@ Nature 385:587.

Yamamoto, J. K., N. C. Pedersen, E. W. Ho, T. Okuda, G. H. Theilen (1988a) A Feline Immunodeficiency Syndrome—A Comparison Between Feline T-lymphotropic Lentivirus and Feline Leukemia Virus@ Leukemia, December Supplement 2:204S-215S.

Yamamoto, J. K., E. Sparger, E. W. Ho, P. H. Andersen, T. P. O=Connor, C. P. Mandell, L. Lowenstine, N. C. Pedersen (1988b) A Pathogenesis of Experimentally Induced Feline Immunodeficiency Virus Infection in Cats@ Am. J. Vet. Res. 49:1246-1258.

Yamamoto, J. K., H. Hansen, E. W. Ho, T. Y. Morishita, T. Okuda, T. R. Sawa, R. M. Nakamura, N. C. Pedersen (1989) A Epidemiologic and Clinical Aspects of Feline Immunodeficiency Virus Infection (FIV) Infection in Cats from the Continental United States and Canada and Possible Mode of Transmission@ J. Am. Vet. Med. Assoc. 194(2):213-220.

Yamamoto, J. K. et al. (1993) A Experimental Vaccine Protection Against Homologous and Heterologous Strains of Feline Immunodeficiency Virus@ J. Virol. 67:601-605.

I claim:

1. An immunogenic composition comprising a) an FIV p24 protein, and b) an HIV-1 p24 protein, wherein said FIV p24 protein and/or said HIV-1 p24 protein comprises an epitope that is evolutionarily conserved between FIV and HIV-1 such that an antibody that binds to said FIV p24 epitope also binds to said HIV-1 p24 epitope, and wherein said immunogenic composition comprises an amount of said FIV p24 protein and said HIV-1 p24 protein effective to induce an immune response in an animal immunized with said immunogenic composition.

2. An immunogenic composition comprising a) an FIV p24 protein, and b) an HIV-1 p24 protein, wherein said FIV p24 protein and HIV-1 p24 protein each comprise an epitope that binds an antibody, and wherein said antibody binds to said epitope on said FIV p24 protein and said antibody also binds to said epitope on said HIV-1 p24 protein, and wherein said immunogenic composition comprises an amount of said FIV p24 protein and said HIV-1 p24 protein effective to induce an immune response in an animal immunized with said immunogenic composition.

3. The immunogenic composition according to claim 2, wherein said FIV p24 protein comprises FIV protein from two or more different FIV subtypes.

4. The immunogenic composition according to claim 3, wherein said two or more subtypes are subtype A and subtype D.

5. The immunogenic composition according to claim 2, wherein said composition is a liquid solution, powder, suspension, tablet, pill, capsule, or sustained release formulation.

6. The immunogenic composition according to claim 2, wherein said composition further comprises one or more of water, saline, dextrose, glycerol, or ethanol.

7. The immunogenic composition according to claim 2, wherein said composition further comprises one or more of an emulsifying agent, a pH buffering agent, or an adjuvant.

8. The immunogenic composition according to claim 7, wherein said adjuvant is aluminum hydroxide or muramyl dipeptide.

9. The immunogenic composition according to claim 2, further comprising an adjuvant.

* * * * *

SEQUENCE LISTING

```
<160> NUMBER OF SEQ ID NOS: 68

<210> SEQ ID NO 1
<211> LENGTH: 24
<212> TYPE: DNA
<213> ORGANISM: Artificial Sequence
<220> FEATURE:
```

<223> OTHER INFORMATION: synthetic oligonucleotide GAGF

<400> SEQUENCE: 1
caacaaggta ggagagattc taca         24

<210> SEQ ID NO 2
<211> LENGTH: 24
<212> TYPE: DNA
<213> ORGANISM: Artificial Sequence
<220> FEATURE:
<223> OTHER INFORMATION: synthetic oligonucleotide GAGR

<400> SEQUENCE: 2
taaaattgtt atatctgctc ctgt         24

<210> SEQ ID NO 3
<211> LENGTH: 1353
<212> TYPE: DNA
<213> ORGANISM: Feline immunodeficiency virus

<400> SEQUENCE: 3

```
atggggaatg acaggggcg agactggaag acggccgtta agagatgtag taatgttgct    60
gtagggtag ggagtaagag tagaaagttt ggagaaggaa actttaggtg ggccataagg   120
atggctaatg taactacagg acgagaacct ggtgatatac cagagaattt agaacagtta   180
agatcgatta tttgtgattt acatgacaga agagaacaat atggatctag taagaaaatt   240
gatatggcaa ttaccacttt aaaagttttt gcagtagctg gaattttaaa tatgactgtg   300
tctactgccg cagcagctga acacatgtat gctcagatgg gattagatac cagaccatct   360
ataaaagaaa gtggggaaa agaagaagga cctccacagg cttatcctat tcaaacagta   420
aatggagcac acagtatgt agcccttgac ccaaaaatgg tgtccatttt tatgaaaaa    480
gcaagagagg ggctaggagg tgaggaggtc caactgtggt tcacagcctt ttctgctaat   540
ttaacttcaa ctgatatggc tacattaatt atgtctgcgc ctggctgtgc agcagataaa   600
gagatcttag atgaaacact gaaacagatg acagctgagt atgatcgtac tcatcctcct   660
gatgggccta accgctgcc ctatttcacc gctgcggaga ttatgggaat aggattaact   720
caagaacaac aagcggagcc cagatttgca ccagctagaa tgcagtgtag agcatggtat   780
cttgaagcac taggaaagtt ggcagccata aaagctaaat ctccccgagc agtgcaattg   840
aagcaaggag ctaaagagga ttattcctca tttatagata gattatttgc tcaaatagat   900
caagagcaga acacagctga agtaaagctg tatttaaaac aatctttgag catagccaat   960
gctaacccag attgtaaaag gcaatgagt catcttaaac cagagagtac tttagaggaa  1020
aaactgagag cctgtcaaga ggtaggatca ccaggatata aaatgcagtt gttagcagaa  1080
gctcttacaa gggttcagac agttcaaaca agaggatcta gaccaacgtg tttcaattgt  1140
aaaaaaccag gccacctggc caaacaatgt agagaagcaa agagatgtaa caactgtgga  1200
aaacctggtc acttagctgc taattgctgg caaagaggta aaaaaccccc gggaaacggg  1260
aagatggggc cagctgcagc cccggtaaac caagtgcagc aaatggtgcc atctgcacct  1320
ccaatggaag acaggaaatt gttagattta taa                              1353
```

<210> SEQ ID NO 4
<211> LENGTH: 1353
<212> TYPE: DNA
<213> ORGANISM: Feline immunodeficiency virus

<400> SEQUENCE: 4

```
atggggaatg gacaggggcg agactggaag gcggccgtta agagatgtag taatgttgct    60
gtaggggtag ggagtaagag tagaaagttt ggagaaggaa actttaggtg ggccataagg   120
atggctaatg taactacagg acgagaacct ggtgatatac cagagaattt agaacagtta   180
agatcgatta tttgtgattt acataacaga agagaacaat atggatctag taagaaaatt   240
gatatggcaa ttaccacttt aaaagttttt gcagtagctg gaattttaaa tatgactgtg   300
tctactgccg cagcagctga acacatgtat gctcagatgg gattagatac cagaccatct   360
ataaaagaaa gtgggggaaa agaagaagga cctccacagg cttatcctat tcaaacagta   420
aatggagcac cacagtatgt agcccttgac ccaaaaatgg tgtccatttt tatggaaaaa   480
gcaagagagg ggctaggagg tgaggaggtc caactgtggt tcacagcctt ttctgctaat   540
ttaacttcaa ctgatatggc tacattaatt atgtctgcgc ctggctgtgc agcagataaa   600
gagatcttag atgaaacact gaaacagata acagctgatt atgatcgtac tcatcctcct   660
gatgggccta gaccgctacc ctatttcacc gctgcgagaa ttatgggaat aggattaact   720
caagaacaac aagcggagcc cagatttgca ccagctagaa tgcagtgtag agcatggtat   780
cttgaagcac taggaaggtt ggcagccata aaagctaaac ctccccgagc agtgcaattg   840
aagcaaggag ctaaagagga ttattcctca tttatagata gattatttgc tcaaatagat   900
caagagcaga cacagctgac agtaaagctg tatttaaaac aatctttgag catagccaat   960
gctaacccag attgtaaaag gcaatgagt catcttaaac cagagagtac tttagaggaa  1020
aaactgagag cctgtcaaga ggtaggatca ccaggatata aaatgcagtt gttagcagaa  1080
gctcttacaa gggttcagac agttcaaaca agaggatcta gaccaacgtg tttcaattgt  1140
aaaaaaccag gccacctggc caaacaatgt agagaagcaa agagatgtaa caactgtgga  1200
aaacctggtc acttagctgc taattgctgg caaagaggaa aaaaaccccc gggaaacggg  1260
aagatggggc cagctgcagc cccggtaaac caagtgcagc aaatggtgcc atctgcacct  1320
ccaatggaag acaggaaatt gttagattta taa                                1353

<210> SEQ ID NO 5
<211> LENGTH: 1353
<212> TYPE: DNA
<213> ORGANISM: Feline immunodeficiency virus

<400> SEQUENCE: 5
atggggaatg gacaggggcg agactggaag gcggccgtta agagatgtag taatgttgct    60
gtaggggtag ggagtaagag tagaaagttt ggagaaggaa actttaggtg ggccataagg   120
atggctaatg taactacagg acgagaacct ggtgatatac cagagaattt agaacagtta   180
agattgatta tttgtgattt acatgacaga agagaacaat atggatctag taagaaaatt   240
gatatggcaa ttaccacttt aaaagttttt gcagtagctg gaattttaaa tatgactgtg   300
tctactgccg cagcagctga acacatgtat gctcagatgg gattagatac cagaccatct   360
ataaaagaaa gtgggggaaa agaagaagga cctccacagg cttatcctat tcaaacagta   420
aatggagcac cacagtatgt agcccttgac ccaaaaatgg tgtccatttt tatggaaaaa   480
gcaagagagg ggctaggagg tgaggaggtc caactgtggt tcacagcctt ttctgctaat   540
ttaacttcaa ctgatatggc tacattaatt atgtctgcgc ctggctgtgc agcagataaa   600
gagatcttag atgaaacact gaaacagata acagctgatt atgatcgtac tcatcctcct   660
gatgggccta gaccgctgcc ctatttcacc gctgcggaga ttatgggaat aggattaact   720
```

```
caagaacaac aagcggagcc cagatttgca ccagctagaa tgcagtgtag agcatggtat      780
cttgaagcac taggaaggtt ggcagccata aaagctaaat ctccccgagc agtgcaattg      840
aagcaaggag ctaaagagga ttattcctca tttatagata gattatttgc tcaaatagat      900
caagagcaga acacagctga agtaaagctg tatttaaaac aatctttgag catagccaat      960
gctaacccag attgtaaaag gcaatgagt catcttaaac cagagagtac tttagaggaa     1020
```



```
caagaacaac aagcggagcc cagatttgca ccagctagaa tgcagtgtag agcatggtat      780
cttgaagcac taggaaggtt ggcagccata aaagctaaat ctccccgagc agtgcaattg      840
aagcaaggag ctaaagagga ttattcctca tttatagata gattatttgc tcaaatagat      900
caagagcaga acacagctga agtaaagctg tatttaaaac aatctttgag catagccaat      960
gctaacccag attgtaaaag gcaatgagt catcttaaac cagagagtac tttagaggaa     1020
aaactgagag cctgtcaaga ggtaggatca ccaggatata aaatgcagtt gttagcagaa     1080
gctcttacaa gggttcagac agttcaaaca agaggatcta gaccaacgtg tttcaattgt     1140
aaaaaaccag ccacctggc caaacaatgt agagaagcaa agagatgtaa caactgtgga     1200
aaacctggtc acttagctgc taattgctgg caaagaggta aaaaaacccc gggaaacggg     1260
aagatggggc cagctgcagc cccggtaaac caagtgcagc aaatggtgcc atctgcacct     1320
ccaatggaag acaggaaatt gttagattta taa                                  1353

<210> SEQ ID NO 6
<211> LENGTH: 1353
<212> TYPE: DNA
<213> ORGANISM: Feline immunodeficiency virus

<400> SEQUENCE: 6
atggggaatg gacaggggcg agactggaag acggccgtta agagatgtag taatgttgct       60 gtagggtag ggagtaagag tagaaaattt ggagaaggaa actttaggtg ggccataagg      120
atggctaatg taactacagg acgagaacct ggtgatatac cagagaattt agaacagtta      180
agatcgatta tttgtgattt acataacaga agagaacaat atggatctag taagaaaatt      240
gatatggcaa ttaccacttt aaaagttttt gcagtagctg gaattttaaa tatgactgtg      300
tctactgccg cagcagctga acacatgtat gctcagatgg gattagatac cagaccatct      360 ataaagaaa gtgggggaaa agaagaagga cctccacagg cttatcctat tcaaacagta      420 aatgagcac acagtatgt agcccttgac ccaaaaatgg tgtccatttt tatgaaaaaa      480
gcaagagagg ggctaggagg tgaggaggtc caactgtggt tcacagcctt ttctgctaat      540
ttaacttcaa ctgatatggc tacattaatt atgtctgcgc ctggctgtgc agcagataaa      600
gagatcttag atgaaacact gaaacagata acagctgatt atgatcgtac tcatcctcct      660
gatgggccta daccgctgcc ctatttcacc gctgcgagaa ttatgggaat aggattaact      720
caagaacaac aagcggagcc cagatttgca ccagctagaa tgcagtgtag agcatggtat      780
cttgaagcac taggaaggtt ggcagccata aaagctaaat ctcccctgagc agtgcaattg      840 aagcaaggag ctaaagagga ttattcctca tttatagata gattatttgc tcaaatagat      900
caagagcaga acacagctga agtaaagctg tatttaaaac aatctttgag catagccaat      960
gctaacccag attgtaaaag gcaatgagt catcttaaac cagagagtac tttagaggaa     1020
aaactgagag cctgtcaaga ggtaggatca ccaggatata aaatgcagtt gttagcagaa     1080
gctcttacaa gggttcagac agttcaaaca agaggatcta gaccaacgtg tttttaattgt     1140 aaaaaaccag ccacctggc caaacaatgt agagaagcaa agagatgtaa caactgtgga     1200
aaacctggtc acttagctgc taattgctgg caaagaggta aaaaaacccc gggaaacggg     1260
aagatggggc cagctgcagc cccggtaaac caagtgcagc aaatggtgcc atctgcacct     1320
ccaatggaag acaggaaatt gttagattta taa                                  1353

<210> SEQ ID NO 7
<211> LENGTH: 1353
```

```
<212> TYPE: DNA
<213> ORGANISM: Feline immunodeficiency virus

<400> SEQUENCE: 7
atggggaatg  gacaggggcg  agactggaag  acggccatta  agagatgtag  taatgttgct      60
gtaggagtag  agagtaagag  tagaaagttt  gaaaagaaa   actttaggtg  ggccataaag    120
atggctaatg  taactacagg  acgagaacct  ggtgatatac  cagagaattt  agaacagtta    180
agatcgatta  tttgtgattt  acatgacaga  agagaacaat  atggatctag  taagaaaatt    240
gatatggcaa  ttaccacttt  aaaagttttt  gcagtagctg  gaattttaaa  tatgactgtg    300
tctactgccg  cagcagctga  acacatgtat  gctcagatgg  gattagatac  cagaccatct    360
ataaaagaaa  gtgggggaaa  agaagaagga  cctccacagg  cttatcctat  tcaaacagta    420
aatggagcac  cacagtatgt  agcccttgac  ccaaaaatgg  tgtccatttt  tatggaaaaa    480
gcaagagagg  ggctaggagg  tgaggaggtc  caactgtggt  tcacagcctt  ttctgctaat    540
ttaacttcaa  ccgatatggc  tacattaatt  atgtctgcgc  ctggctgtgc  agcagataaa    600
gagatcttag  atgaaacact  gaaacagatg  acagctgagt  atgatcgtac  tcatcctcct    660
gatgggccta  daccgctgcc  ctatttcacc  gctgcggaga  ttatgggaat  aggattaact    720
caagaacaac  aggcggagcc  cagatttgca  ccagctagaa  tgcagtgtag  agcatggtat    780
cttgaagcac  taggaaagtt  ggcagccata  aaagctaaat  ctccccgagc  agtgcaatta    840
aagcaaggag  ctaaagagga  ttattcctca  tttatagata  gattatttgc  tcaaatagat    900
caagagcaga  cacagctgaa  gtaaagctg   tatttaaaac  aatctttgag  catagccaat    960
gctaacccag  attgtaaaag  ggcaatgagt  catcttaaac  cagagagtac  tttagaggaa   1020
aaactgagag  cctgtcaaga  ggtaggatca  ccaggatata  aaatgcagtt  gttagcagaa   1080
gctcttacaa  gggttcagac  agttcaaaca  agaggatcta  gaccaacgtg  tttcaattgt   1140
aaaaaaccag  gccacctggc  caaacaatgt  agagaagcaa  agagatgtaa  caactgtgga   1200
aaacctggtc  acttagctgc  taattgctgg  caaagaggta  aaaaaacccc  gggaaacggg   1260
aagatggggc  cagctgcagc  cccggtaaac  caagtgcagc  aaatggtgcc  atctgcacct   1320
ccaatggaag  acaggaaatt  gttagattta  taa                                  1353

<210> SEQ ID NO 8
<211> LENGTH: 1353
<212> TYPE: DNA
<213> ORGANISM: Feline immunodeficiency virus

<400> SEQUENCE: 8
atggggaatg  gacaggggcg  agactggaag  acggccgtta  agagatgtag  taatgttgct      60
gtaggggtag  ggagtaagag  tagaaagttt  ggagaaggaa  actttaggtg  ggccataagg    120
atggctaatg  taactacagg  acgagaacct  ggtgatatac  cagagaattt  agaacagtta    180
agatcgatta  tttgtgattt  acatgacaga  agagaacaat  atggatctag  taagaaaatt    240
gatatggcaa  ttaccacttt  aaaagttttt  gcagtagctg  gagttttaaa  tatgactgtg    300
tctactgccg  cagcagctga  acacatgtat  gctcagatgg  gattagatac  cagaccatct    360
ataaaagaaa  gtgggggaaa  agaagaagga  cctccacagg  cttatcctat  tcaaacagta    420
aatggagcac  cacagtatgt  agcccttgac  ccaaaaatgg  tgtccatttt  tatggaaaaa    480
gcaagagagg  ggctaggagg  tgaggaggtc  caactgtggt  tcacagcctt  ttctgctaat    540
ttaacttcaa  ctgatatggc  tacattaatt  atgtctgcgc  ctggctgtgc  agcagataaa    600
```

```
gagatcttag atgaaacact gaaacagatg acagctgagt atgatcgtac tcatcctcct    660
gatgggccta daccgctgcc ctatttcacc gctgcggaga ttatgggaat aggattaact    720
caagaacaac aagcggagcc cagatttgca ccagctagaa tgcagtgtag agcatggtat    780
cttgaagcac taggaaagtt ggcagccata aaagctaaat ctccccgagc agtgcaattg    840
aagcaaggag ctaagagga ttattcctca tttatagata gattatttgc tcaaatagat    900
caagagcaga acacagctga agtaaagctg tatttaaaac aatctttgag catagccaat    960
gctaacccag attgtaaaag gcaatgagt catcttaaac cagagagtac tttagaggaa    1020
aaactgagag cctgtcaaga ggtaggatca ccaggatata aaatgcagtt gttagcagaa    1080
gctcttacaa gggttcagac agttcaaaca agaggatcta gaccaacgtg tttcaattgt    1140
aaaaaaccag gccacctggc caaacaatgt agagaagcaa agagatgtaa caactgtgga    1200
aaacctggtc acttagctgc taattgctgg caaagaggta aaaaaacccc gggaaacggg    1260
aagatggggc cagctgcagc cccggtaaac caagtgcagc aaatggtgcc atctgcacct    1320
ccaatggaag acaggaaatt gttagattta taa    1353

<210> SEQ ID NO 9
<211> LENGTH: 1353
<212> TYPE: DNA
<213> ORGANISM: Feline immunodeficiency virus

<400> SEQUENCE: 9
atggggaatg acaggggcg agactggaag acggccgtta agagatgtag taatgttgct    60
gtaggggtag ggagtaagag tagaaagttt ggagaaggaa actttaggtg ggccataagg    120
atggctaatg taactacagg acgagaacct ggtgatatac cagagaattt agaacagtta    180
agatcgatta tttgtgattt acatgacaga agagaacaat atggatctag taagaaaatt    240
gatatggcaa ttaccacttt aaaagttttt gcagtagctg aattttaaa tatgactgtg    300 tctactgccg cagcagctga acacatgtat gctcagatgg gattagatac cagccatct    360 ataaagaaaa gtgggggaaa agaagaagga cctccacagg cttatcctat tcaaacagta    420
aatggagcac cacagtatgt agcccttgac ccaaaaatgg tgtccatttt tatggaaaaa    480
gcaagagagg ggctaggagg tgaggaggtc caactgtggt tcacagcctt tctgctaat    540 ttaacttcaa ctgatatggc tacattaatt atgtctgcgc ctggctgtgc agcagataaa    600
gagatcttag atgaaacact gaaacagatg acagctgagt atgatcgtac tcatcctcct    660
gatgggccta daccgctgcc ctatttcacc gctgcggaga ttatgggaat aggattaact    720
caagaacaac aagcggagcc cagatttgca ccagctagaa tgcagtgtag agcatggtat    780
cttgaagcac taggaaagtt ggcagccata aaagctaaat ctccccgagc agtgcaattg    840
aagcaaggag ctaagagaa ttattcctca tttatagata gattatttgc tcaaatagat    900
caagagcaga acacagctga agtaaagctg tatttaaaac aatctttgag catagccaat    960
gctaacccag attgtaaaag gcaatgagt catcttaaac cagagagtac tttagaggaa    1020
aaactgagag cctgtcaaga ggtaggatca ccaggatata aaatgcagtt gttagcagaa    1080
gctcttacaa gggttcagac agttcaaaca agaggatcta gatcaacgtg tttcaattgt    1140
aaaaaaccag gccacctggc caaacaatgt agagaagcaa agagatgtaa caactgtgga    1200
aaacctggtc acttagctgc taattgctgg caaagaggta aaaaaacccc gggaaacggg    1260
aagatggggc cagctgcagc cccggtaaac caagtgcagc agatggtgcc atctgcacct    1320
ccaatggaag acaggaaatt gttagattta taa    1353
```

<210> SEQ ID NO 10
<211> LENGTH: 1353
<212> TYPE: DNA
<213> ORGANISM: Feline immunodeficiency virus

<400> SEQUENCE: 10

```
atggggaatg gacaggggcg agactggaag acggccgtta agagatgtag taatgttgct      60
gtaggggtag ggagtaagag tagaaagttt ggagaaggaa actttaggtg ggccataagg     120
atggctaatg taactacagg acgagaacct ggtgatatac cagagaattt agaacagtta     180
agatcgatta tttgtgattt acatgacaga gagaacaat atggatctag taagaaatt      240
gatatggcaa ttaccacttt aaaagttttt gcagtagctg aattttaaa tatgactgtg     300
tctactgccg cagcagctga acacatgtat gctcagatgg gattagatac cagaccatct     360
ataaaagaaa gtgggggaaa agaagaagga cctccacagg cttatcctat tcaaacagta     420
aatggagcac cacagtatgt agcccttgac ccaaaaatgg tgtccatttt tatggaaaaa     480
gcaagagagg ggctaggagg tgaggaggtc caactgtggt tcacagcctt ttctgctaat     540
ttaacttcaa ctgatatggc tacattaatt atgtctgcgc ctggctgtgc agcagataaa     600
gagatcttag atgaaacact gaaacagatg acagctaagt atgatcgtac tcatcctcct     660
gatgggccta accgctgcc ctatttcacc gctgcggaga ttatgggaat aggattaact     720
caagaacaac aagcggagcc cagatttgca ccagctgaa tgcagtgtag agcatggtat     780
cttgaagcac taggaaagtt ggcagccata aaagctaaat ctccccgagc agtgcaattg     840
aagcaaggag ctaaagagga ttattcctca tttatagata gattatttgc tcaaatagat     900
caagagcaga cacagctga agtaaagctg tatttaaaac aatctttgag catagccaat     960
gctaacccag attgtaaaag ggcaatgagt catcttaaac cagagagtac tttagaggaa    1020
aaactgagag cctgtcaaga ggtaggatca ccaggatata aaatgcagtt gttagcagaa    1080
gctcttacaa gggttcagac agttcaaaca agaggatcta gaccaatgtg tttcaattgt    1140
aaaaaaccag gccacctggc caaacaatgt agagaagcaa agagatgtaa caactgtgga    1200
aaacctggtc acttagctgc taattgctgg caaagaggta aaaaaccc gggaaacggg     1260
aagatggggc cagctgcagc cccggtaaac caagtgcagc aaatggtgcc atctgcacct    1320
ccaatggaag acaggaaatt gttagattta taa                                 1353
```

<210> SEQ ID NO 11
<211> LENGTH: 1353
<212> TYPE: DNA
<213> ORGANISM: Feline immunodeficiency virus

<400> SEQUENCE: 11

```
atggggaatg gacaggggcg agactggaag acggccgtta agagatgtag taatgttgct      60
gtaggggtag ggagtaagag tagaaagttt ggagaaggaa actttaggtg ggccataagg     120
atggctaatg taactacagg acgagaacct ggtgatatac cagagaattt agaacagtta     180
agatcgatta tttgtgattt acatgacaga gagaacaat atggatctag taagaaatt      240
gatatggcaa ttaccacttt aaaagttttt gcagtagctg aattttaaa tatgactgtg     300
tctactgccg cagcagctga acacatgtat gctcagatgg gattagatac cagaccatct     360
ataaaagaaa gtgggggaaa agaagaagga cctccacagg cttatcctat tcaaacagta     420
aatggagcac cacagtatgt agcccttgac ccaaaaatgg tgtccatttt tatggaaaaa     480
```

-continued

```
gcaagagagg ggctaggagg tgaggaggtc caactgtggt tcacagcctt ttctactaat    540
ttaacttcaa ctgatatggc tacattaatt atgtctgcgc ctggctgtgc agcagataaa    600
gagatcttag atgaaacact gaaacagatg acagctgagt atgatcgtac tcatcctcct    660
gatgggccta gaccgctgcc ctatttcacc gctgcggaga ttatgggaat aggattaact    720
caagaacaac aagcggagcc cagatttgca ccagctagaa tgcagtgtag agcatggtat    780
cttgaagcac taggaaagtt ggcagccata aaagctaaat ctccccgagc agtgcaattg    840
aagcaaggag ctaagagga ttattcctca tttatagata gattatttgc tcaaatagat    900
caagagcaga acacagctga agtaaagctg tatttaaaac aatctttgag catagccaat    960
gctaacccag attgtaaaag gcaatgagt catcttaaac cagagagtac tttagaggaa   1020
aaactgagag cctgtcaaga ggtaggatca ccaggatata aaatgcagtt gttagcagaa   1080
gctcttacaa gggttcagac agttcaaaca agaggatcta gaccaacgtg tttcaattgt   1140
aaaaaaccag gccacctggc caaacaatgt agagaagcaa agagatgtaa caactgtgga   1200
aaacctggtc acttagctgc taattgctgg caaagaggta aaaaaccccc gggaaacggg   1260
aagatggggc cagctgcagc cccggtaaac caagtgcagc aaatggtgcc atctgcacct   1320
ccaatggaag acaggaaatt gttagattta taa                                1353
```

<210> SEQ ID NO 12
<211> LENGTH: 1353
<212> TYPE: DNA
<213> ORGANISM: Feline immunodeficiency virus

<400> SEQUENCE: 12

```
atggggaatg gacaggggcg agactggaag acggccgtta agagatgtag taatgttgct     60
gtaggggtag ggagtaagag tagaaagttt ggagaaggaa actttaggtg ggccataagg    120
atggctaatg taactacagg acgagaacct ggtgatatac cagagaattt agaacagtta    180
agatcgatta tttgtgattt acatgacaga gagaacaat atggatctag taagaaaatt    240
gatatggcaa ttaccacttt aaaagttttt gcagtagctg gaattttaaa tatgactgtg    300
tctactgccg cagcagctga acacatgtat gctcagatgg gattagatac cagaccatct    360
ataaaagaaa gtgggggaaa agaagaagga cctccacagg cttatcctat tcaaacagta    420
aatggagcac acagtatgt agcccttgac ccaaaaatgg tgtccatttt tatgaaaaaa    480
gcaagagagg ggctaggagg tgaggaggtc caactgtggt tcacagcctt ttctgctaat    540
ttaacctcaa ctgatatggc tacattaatt atgtctgcgc ctggctgtgc agcagataaa    600
gagatcttag atgaaacact gaaacagatg acagctgagt atgatcgtac tcatcctcct    660
gatgggccta gaccgctgcc ctatttcacc gctgcggaga ttatgggaat aggattaact    720
caagaacaac aagcggagcc cagatttgca ccagctagaa tgcagtgtag agcatggtat    780
cttgaagcac taggaaagtt ggcagccata aaagctaaat ctccccgagc agtgcaattg    840
aagcaaggag ctaagagga ttattcctca tttatagata gattatttgc tcaaatagat    900
caagagcaga acacagctga agtaaagctg tatttaaaac aatctttgag catagccaat    960
gctaacccag attgtaaaag gcaatgagt catcttaaac cagagagtac tttagaggaa   1020
aaactgagag cctgtcaaga ggtaggatca ccaggatata aaatgcagtt gttagcagaa   1080
gctcttacaa gggttcagac agttcaaaca agaggatcta gaccaacgtg tttcaattgt   1140
aaaaaaccag gccacctggc caaacaatgt agagaagcaa agagatgtaa caactgtgga   1200
aaacctggtc acttagctgc taattgctgg caaagaggaa aaaaaccccc gggaaacggg   1260
```

```
aagatggggc cagctgcagc cccggtaaac caagtgcagc aaatggtgcc atctgcacct      1320
ccaatggaag acaggaaatt gttagattta taa                                  1353

<210> SEQ ID NO 13
<211> LENGTH: 1353
<212> TYPE: DNA
<213> ORGANISM: Feline immunodeficiency virus

<400> SEQUENCE: 13
atggggaatg gacaggggcg agactggaag acggccgtta agagatgtag taatgttgct      60
gtaggggtag ggagtaagag tagaaagttt ggagaaggaa actttaggtg ggccataagg     120
atggctaatg taactacagg acgagaacct ggtgatatac cagagaattt agaacagtta     180
agatcgatta tttgtgattt acatggcaga agagaacaat atggatctag taaagaaatt     240
gatatggcaa ttaccacttt aaaagttttt gcagtagctg gaattttaaa tatgactgtg     300
tctactgccg cagcagctga acacatgtat gctcagatgg gattagatac cagaccatct     360
ataaagaaag gtgggggaaa agaagaagga cctccacagg cttatcctat tcaaacagta     420
aatggagcac cacagtatgt agcccttgac ccaaaaatgg tgtccatctt tatggaaaaa     480
gcaagagagg ggctaggagg tgaggaggtc caactgtggt tcacagcctt ttctgctaat     540
ttaacttcaa ctgatatggc tacattaatt atgtctgcgc ctggctgtgc agcagataaa     600
gagatcttag atgaaacact gaaacagatg acagctgagt atgatcgtac tcatcctcct     660
gatgggccta gccgctaccc ctatttcacc gctgcggaga ttatgggaat aggattaact     720
caagaacaac aagcggagcc cagatttgca ccagctagaa tgcagtgtag agcatggtat     780
cttgaagcac taggaaagtt ggcagccata aagctaaatc tccccgagcc agtgcaattg     840
aagcaaggag ctaaagagga ttattcctca tttatagata gattatttgc tcaaatagat     900
caagagcaga cacagctgaa gtaaagctgt atttaaaaac aatctttgag catagccaat     960
gctaacccag attgtaaaag gcaatgagt catcttaaac cagagagtac tttagaggaa    1020
aaactgagag cctgtcaaga ggtaggatca ccaggatata aaatgcagtt gttagcagaa    1080
gctcttacaa gggttcagac agttcaaaca agaggatcta gaccaacgtg tttcaattgt    1140
aaaaaaccag gccacctggc caaacaatgt agagaagcaa agagatgtaa caactgtgga    1200
aaacctggtc acttagctgc taattgctgg caaagaggta aaaaacccc gggaaacggg    1260 aagatggggc cagctgcagc cccggtaaac caagtgcagc aaatggtgcc atctgcacct    1320
ccaatggaag acaggaaatt gttagattta taa                                 1353

<210> SEQ ID NO 14
<211> LENGTH: 1353
<212> TYPE: DNA
<213> ORGANISM: Feline immunodeficiency virus

<400> SEQUENCE: 14
atggggaatg gacaggggcg agactggaag acggccgtta agagatgtag taatgttgct      60
gtaggggtag ggagtaagag tagaaagttt ggagaaggaa actttaggtg ggccataagg     120
atggctaatg taactacagg acgagaacct ggtgatatac cagagaattt agaacagtta     180
agatcgatta tttgtgattt acatggcaga agagaacaat atggatctag taaagaaatt     240
gatatggcaa ttaccacttt aaaagttttt gtagtagctg gaattttaaa tatgactgtg     300
tctactgccg cagcagctga acacatgtat gctcagatgg gattagatac cagaccatct     360
```

```
ataaaagaag gtgggggaaa agaagaagga cctccacagg cttatcctat tcaaacagta        420
aatggagcac cacagtatgt agcccttgac ccaaaaatgg tgtccatctt tatggaaaaa        480
gcaagagagg ggctaggagg tgaggaggtc aactgtggt tcacagcctt ttctgctaat         540
ttaacttcaa ctgatatggc tacattaatt atgtctgcgc ctggctgtgc agcagataaa        600
gagatcttag atgaaacact gaaacagatg acagctgagt atgatcgtac tcatcctcct        660
gatgggccta daccgctgcc ctatttcacc gctgcggaga ttatgggaat aggattaact        720
caagaacaac aagcggagcc cagatttgca ccagctagaa tgcagtgtag agcatggtat        780
cttgaagcac taggaaagtt ggcagccata aaagctaaat ctccccgagc agtgcaattg        840
aagcaaggag ctaaagagga ttattcctca tttatagata gattatttgc tcaaatagat        900
caagagcaga acacagctga agtaaagctg tatttaaaac aatctttgag catagccaat        960
gctaacccag attgtaaaag ggcaatgagt catcttaaac cagagagtac tttagaggaa       1020
aaactgagag cctgtcaaga ggtaggatca ccaggatata aaatgcagtt gttagcagaa       1080
gctcttacaa gggttcagac agttcaaaca agaggatcta gaccaacgtg tttcaattgt       1140
aaaaaaccag gccacctggc caaacaatgt agagaagcaa agagatgtaa caactgtgga       1200
aaacctggtc acttagctgc taattgctgg caaagaggta aaaaaacccc gggaaacggg       1260
aagatggggc cagctgcagc cccggtaaac caagtgcagc aaatggtgcc atctgcacct       1320
ccaatggaag acaggaaatt gttagattta taa                                    1353

<210> SEQ ID NO 15
<211> LENGTH: 1353
<212> TYPE: DNA
<213> ORGANISM: Feline immunodeficiency virus

<400> SEQUENCE: 15
atggggaatg gacaggggcg agactggaag acggccgtta agagatgtag taatgttgct         60
gtaggggtag ggagtaagag tagaaagttt ggagaaggaa acttaggtg ggccataagg         120 atggctaatg taactacagg acgagaacct ggtgatatac cagagaattt agaacagtta        180
agatcgatta tttgtgattt acatggcaga agagaacaat atggatctag taagaaaatt        240
gatatggcaa ttaccacttt aaaagttttt gcagtagctg gaattttaaa tatgactgtg        300
tctactgccg cagcagctga acacatgtat gctcagatgg gattagatac cagaccatct        360
ataaaagaag gtgggggaaa agaagaagga cctccacagg cttatcctat tcaaacagta        420
aatggagcac cacagtatgt agcccttgac ccaaaaatgg tgtccatctt tatggaaaaa        480
gcaagagagg ggctaggagg tgaggaggtc aactgtggt tcacagcctt ttctgctaat         540
ttaacttcaa ctgatatggc tacattaatt atgtctgcgc ctggctgtgc agcagataaa        600
gagatcttag atgaaacact gaaacagatg acagctgagt atgatcgtac tcatcctcct        660
gatgggccta daccgctgcc ctatttcacc gctgcggaga ttatgggaat aggattaact        720
caagaacaac aagcggagcc cagatttgca ccagctagaa tgcagtgtag agcatggtat        780
cttgaagcac taggaaagtt ggcagccata aaagctaaat ctccccgagc agtgcaattg        840
aagcaaggag ctaaagagga ttattcctca tttatagata gattatttgc tcaaatagat        900
caagagcaga acacagctga agtaaagctg tatttaaaac aatctttgag catagccaat        960
gctaacccag attgtaaaag ggcaatgagt catcttaaac cagagagtac tttagaggaa       1020
aaactgagag cctgtcaaga ggtaggatca ccaggatata aaatgcagtt gttagcagaa       1080
gctcttacaa gggttcagac agttcaaaca agaggatcta gaccaacgtg tttcaattgt       1140
```

```
aaaaaaccag gccacctggc caaacaatgt agagaagcaa agagatgtaa caactgtgga   1200
aaacctggtc acttagctgc taattgctgg caaagaggta aaaaacccc gggaaacggg    1260 aagatggggc cagctgcagc cccggtaaac caagtgcagc aaatggtgcc atctgcacct   1320
ccaatggaag gcaggaaatt gttagattta taa                               1353
```

<210> SEQ ID NO 16
<211> LENGTH: 1353
<212> TYPE: DNA
<213> ORGANISM: Feline immunodeficiency virus

<400> SEQUENCE: 16

```
atggggaatg gacaggggcg agactggaag acggccgtta agagatgtag taatgttgct   60
gtaggggtag ggagtaagag tagaaagttt ggagaaggaa actttaggtg ggccataagg   120
atggctaatg taactacagg acgagaacct ggtgatatac cagagaattt agaacagtta   180
agatcgatta tttgtgattt acatggcaga agagaacaat atggatctag taagaaaatt   240
gatatggcaa ttaccacttt aaaagttttt gcagtagctg aattttaaa tatgactgtg    300 tctactgccg cagcagctga acacatgtat gctcagatgg gattagatac cagaccatct   360 ataaagaag gtgggggaaa agaagaagga cctccacagg cttatcctat tcaaacagta    420
aatggagcac cacagtatgt agcccttgac ccaaaaatgg tgtccatctt tatggaaaaa   480
gcaagagagg ggctaggagg tgaggaggtc caactgtggt tcacagcctt ttctgctaat   540
ttaacttcaa ctgatatggc tacattaatt atgtctgcgc ctggctgtgc agcagataaa   600
gagatcttag atgaaacact gaaacagatg acagctgagt atgatcgtac tcatcctcct   660
gatgggccta ccgctgcc ctatttcacc gctgcggaga ttatgggaat aggattaact    720
caagaacaac aagcggagcc cagatttgca ccagctagaa tgcagtgtag agcatggtat   780
cttgaagcac taggaaagtt ggcagccata aaagctaaat ctccccgagc agtgcaattg   840
aagcaaggag ctaaagagga ttattcctca tttatagata gattatttgc tcaaatagat   900
caagagcaga acacagctga agtaaagctg tatttaaaac aatctttgag catagccaat   960
gctaacccag attgtaaaag ggcaatgagt catcttaaac cagagagtac tttagaggaa   1020
aaactgagag cctgtcaaga ggtaggatca ccaggatata aaatgcagtt gttagcagaa   1080
gctcttacaa gggttcagac agttcaaaca agaggatcta gaccaacgtg tttcaattgt   1140
aaaaaaccag gccacctggc caaacaatgt agagaagcaa agagatgtaa caactgtgga   1200
aaacctggtc acttagctgc taattgctgg caaagaggta aaaaacccc gggaaacggg    1260 aagatggggc cagctgcagc cccggtaaac caagtgcagc aaatggtgcc atctgcacct   1320
ccaatgggag acaggaaatt gttagattta taa                               1353
```

<210> SEQ ID NO 17
<211> LENGTH: 1353
<212> TYPE: DNA
<213> ORGANISM: Feline immunodeficiency virus

<400> SEQUENCE: 17

```
atggggaatg gacaggggcg agactggaag acggccgtta agagatgtag taatgttgct   60
gtaggggtag ggagtaagag tagaaagttt ggagaaggaa actttaggtg ggccataagg   120
atggctaatg taactacagg acgagaacct ggtgatatac cagagaattt agaacagtta   180
agatcgatta tttgtgattt acatggcaga agagaacaat atggatctag taagaaaatt   240
```

```
gatatggcaa ttaccacttt aaaagttttt gcagtagctg aattttaaa tatgactgtg      300 tctactgccg cagcagctga acacatgtat gctcagatgg gattagatac cagaccatct      360
ataaaagaag gtgggggaaa agaagaagga cctccacagg cttatcctat tcaaacagta      420
aatggagcac cacagtatgt agcccttgac ccaaaaatgg tgtccatctt tatggaaaaa      480
gcaagagagg ggctaggagg tgaggaggtc caactgtggt tcacagcctt ttctgctaat      540
ttaacttcaa ctgatatggc tacattaatc atgtctgcgc ctggctgtgc agcagataaa      600
gagatcttag atgaaacact gaaacagatg acagctgagt atgatcgtac tcatcctcct      660
gatgggccta gaccgctgcc ctatttcacc gctgcggaga ttatgggaat aggattaact      720
caagaacaac aagcggagcc cagatttgca ccagctagaa tgcggtgtag agcatggtat      780
cttgaagcac taggaaagtt ggcagccata aaagctaaat ctccccgagc agtgcaattg      840
aagcaaggag ctaaagagga ttattcctca tttatagata gattatttgc tcaaatagat      900
caagagcaga acacagctga agtaaagctg tatttaaaac aatctttgag catagccaat      960
gctaacccag attgtaaaag ggcaatgagt catcttaaac cagagagtac tttagaggaa     1020
aaactgagag cctgtcaaga ggtaggatca ccaggatata aaatgcagtt gttagcagaa     1080
gctcttacaa gggttcagac agttcaaaca agaggatcta gaccaacgtg tttcaattgt     1140
aaaaaaccag gccacctggc caaacaatgt agagaagcaa agagatgtaa caactgtgga     1200
aaacctggtc acttagctgc taattgctgg caaagagta aaaaaacccc gggaaacggg     1260
aagatggggc cagctgcagc cccggtaaac caagtgcagc aaatggtgcc atctgcacct     1320
ccaatggaag acaggaaatt gttagattta taa                                   1353

<210> SEQ ID NO 18
<211> LENGTH: 1353
<212> TYPE: DNA
<213> ORGANISM: Feline immunodeficiency virus

<400> SEQUENCE: 18
atggggaatg gacaggggcg agactggaag acggccgtta agagatgtag taatgttgct       60
gtaggggtag ggagtaagag tagaaagttt ggagaaggaa acttaggtg ggccataagg      120 atggctaatg taactacagg acgagaacct ggtgatatac cagagaattt agaacagtta      180
agatcgatta tttgtgattt acatggcaga agagaacaat atggatctag taagaaaatt      240
gatatggcaa ttaccacttt aaaagttttt gcagtagctg aattttaaa tatgactgtg      300 tctactgccg cagcagctga acacatgtat gctcagatgg gattagatac cagaccatct      360
ataaaagaag gtgggggaaa agaagaagga cctccacagg cttatcctat tcaaacagta      420
aatggagcac cacagtatgt agcccttgac ccaaaaatgg tgtccatctt tatggaaaaa      480
gcaagagagg ggctaggagg tgaggaggtc caactgtggt tcacagcctt ttctgctaat      540
ttaacttcaa ctgatatggc tacattaatt atgtctgcgc ctggctgtgc agcagataaa      600
gagatcttag atgaaacact gaaacagatg acagctgagt atgatcgtac tcatcctcct      660
gatgggccta gaccgctgcc ctatttcacc gctgcggaga ttatgggaat aggattaact      720
caagaacaac aagcggagcc cagatttgca ccagctagaa tgcagtgtag agcatggtat      780
cttgaagcac taggaaagtt ggcagccata aaagctaaat ctccccgagc agtgcaattg      840
aagcaaggag ctaaagagga ttattcctca tttatagata gattatttgc tcaaatagat      900
caagagcaga acacagctga agtaaagctg tatttaaaac aatctttgag catagccaat      960
gctaacccag attgtaaaag ggcaatgagt catcttaaac cagagagtac tttagaggaa     1020
```

| | | |
|---|---|---|
| aaactgagag cctgtcaaga ggtaggatca ccaggatata aaatgcagtt gttagcagaa | 1080 | |
| gctcttacaa gggttcagac agttcaaaca agaggatcta gaccaacgtg tttcaattgt | 1140 | |
| aaaaaaccag gccacctggc caaacaatgt agagaagcaa agagatgtaa caactgtgga | 1200 | |
| aaacctggtc acttagctgc taattgctgg caaagaggta aaaaaacccc gggaaacggg | 1260 | |
| aagatggggc cagctgcagc cccggtaaac caagtgcagc aaatggtgcc atctgcacct | 1320 | |
| ccaatggaag acaggaaatt gttagattta taa | 1353 | |

<210> SEQ ID NO 19
<211> LENGTH: 1353
<212> TYPE: DNA
<213> ORGANISM: Feline immunodeficiency virus

<400> SEQUENCE: 19

| | | |
|---|---|---|
| atggggaatg gacaggggcg agactggaag acggccgtta agagatgtag taatgttgct | 60 | |
| gtaggggtag ggagtaagag tagaaagttt ggagaaggaa actttaggtg ggccataagg | 120 | |
| atggctaatg taactacagg acgagaacct ggtgatatac cagagaattt agaacagtta | 180 | |
| agatcgatta tttgtgattt acatggcaga agagaacaat atggatctag taagaaaatt | 240 | |
| gatatggcaa ttaccacttt aaaagttttt gcagtagctg gaattttaaa tatgactgtg | 300 | |
| tctactgccg cagcagctga acacatgtat gctcagatgg gattagatac cagaccatct | 360 | |
| ataaaagaag gtgggggaaa agaagaagga cctccacagg cttatcctat tcaaacagta | 420 | |
| aatggagcac acagtatgt agcccttgac ccaaaaatgg tgtccatctt tatggaaaaa | 480 | |
| gcaagagagg ggctaggagg tgaggaggtc caactgtggt tcacagcctt ttctgctaat | 540 | |
| ttaacttcaa ctgatatggc tacattaatt atgtctgcgc ctggctgtgc agcagataaa | 600 | |
| gagatcttag atgaaacact gaaacagatg acagctgagt atgatcgtac tcatcctcct | 660 | |
| gatgggccta daccgctgcc ctatttcacc gctgcggaga ttatgggaat aggattaact | 720 | |
| caagaacaac aagcggagcc cagatttgca ccagctagaa tgcagtgtag agcatggtat | 780 | |
| cttgaagcac taggaaagtt ggcagccata aaagctaaat ctccccgagc agtgcaattg | 840 | |
| aagcaaggag ctaaagagga ttattcctca tttatagata gattatttgc tcaaatagat | 900 | |
| caagagcaga cacagctgaa gtaaagctg tatttaaaac aatctttgag catagccaat | 960 | |
| gctaacccag attgtaaaag gcaatgagt catcttaaac cagagagtac tttagaggaa | 1020 | |
| aaactgagag cctgtcaaga ggtaggatca ccaggatata aaatgcagtt gttagcagaa | 1080 | |
| gctcttacaa gggttcagac agttcaaaca agaggatcta gaccaacgtg tttcaattgt | 1140 | |
| aaaaaaccag gccacctggc caaacaatgt agagaagcaa agagatgtaa caactgtgga | 1200 | |
| aaacctggtc acttagctgc taattgctgg caaagaggta aaaaaacccc gggaaacggg | 1260 | |
| aagatggggc cagctgcagc cccggtaaac caagtgcagc aaatggcgcc atctgcacct | 1320 | |
| ccaatggaag acaggaaatt gttagattta taa | 1353 | |

<210> SEQ ID NO 20
<211> LENGTH: 1353
<212> TYPE: DNA
<213> ORGANISM: Feline immunodeficiency virus

<400> SEQUENCE: 20

| | | |
|---|---|---|
| atggggaatg gacaggggcg agactggaag acggccgtta agagatgtag taatgttgct | 60 | |
| gtaggggtag ggagtaagag tagaaagttt ggagaaggaa actttaggtg ggccataagg | 120 | |

```
atggctaatg taactacagg acgagaacct ggtgatatac cagagaattt agaacagtta      180
agatcgatta tttgtgattt acatggcaga agagaacaat atggatctag taaagaaatt      240
gatatggcaa ttaccacttt aaaagttttt gcagtagctg aattttaaa tatgactgtg       300 tctactgccg cagcagctga acacatgtat gctcagatgg gattagatac cagaccatct      360
ataaaagaag gtgggggaaa agaagaagga cctccacagg cttatcctat tcaaacagta      420
aatggagcac cacagtatgt agcccttgac ccaaaaatgg tgtccatctt tatgaaaaa       480 gcaagagagg ggctaggagg tgaggaggtc caactgtggt tcacagcctt ttctgctaat      540
ttaacttcaa ctgatatggc tacattaatt atgtctgcgc ctggctgtgc agcagataaa      600
gagatcttag atgaaacact gaaacagatg acagctgagt atgatcgtac tcatcctcct      660
gatgggccta daccgctgcc ctatttcacc gctgcggaga ttatgggaat aggattaact      720
caagaacaac aagcggagcc cagatttgca ccagctagaa tgcagtgtag agcatggtat      780
cttgaagcac taggaaagtt ggcagccata aaagctaaat ctccccgagc agtgcaattg      840
aagcaaggag ctaaagagga ttattcctca tttatagata gattatttgc tcaaatagat      900
caagagcaga acacagctga agtaaagctg tatttaaaac aatctttgag catagccaat      960
gctaacccag attgtaaaag ggcaatgagt catcttaaac cagagagtac tttagaggaa     1020
aaactgagag cctgtcaaga ggtaggatca ccaggatata aaatgcagtt gttagcagaa     1080
gctcttacaa gggttcagac agttcaaaca agaggatcta gaccaacgtg tttcaattgt     1140
aaaaaaccag gccacctggc caaacaatgt agagaagcaa agagatgtaa caactgtgga     1200
aaacctggtc acttagctgc taattgctgg caaagaggta aaaaaacccc gggaaacggg     1260
aagatggggc cagctgcagc cccggtaaac caagtgcagc aaatggtgcc atctgcacct     1320
ccaatggaag acaggaaatt gttagattta taa                                   1353

<210> SEQ ID NO 21
<211> LENGTH: 1353
<212> TYPE: DNA
<213> ORGANISM: Feline immunodeficiency virus

<400> SEQUENCE: 21
atggggaatg gacaggggcg agactggaag acggccgtta agagatgtag taatgttgct       60 gtagggtag ggagtaagag tagaaagttt ggagaaggaa actttaggtg ggccataagg       120
atggctaatg taactacagg acgagaacct ggtgatatac cagagaattt agaacagtta      180
agatcgatta tttgtgattt acatggcaga agagaacaat atggatctag taaagaaatt      240
gatatggcaa ttaccacttt aaaagttttt gcagtagctg aattttaaa tatgactgtg       300 tctactgccg cagcagctga acacatgtat gctcagatgg gattagatac cagaccatct      360
ataaaagaag gtgggggaaa agaagaagga cctccacagg cttatcctat tcaaacagta      420
aatggagcac cacagtatgt agcccttgac ccaaaaatgg tgtccatctt tatgaaaaa       480 gcaagagagg ggctaggagg tgaggaggtc caactgtggt tcacagcctt ttctgctaat      540
ttaacttcaa ctgatatggc tacattaatt atgtctgcgc ctggctgtgc agcagataaa      600
gagatcttag atgaaacact gaaacagatg acagctgagt atgatcgtac tcatcctcct      660
gatgggccta daccgctgcc ctatttcacc gctgcggaga ttatgggaat aggattaact      720
caagaacaac aagcggagcc cagatttgca ccagctagaa tgcagtgtag agcatggtat      780
cttgaagcac taggaaagtt ggcagccata aaagctaaat ctccccgagc agtgcaattg      840
aagcaaggag ctaaagagga ttattcctca tttacagata gattatttgc tcaaatagat      900
```

```
caagagcaga acacagctga agtaaagctg tatttaaaac aatctttgag catagccaat    960
gctaacccag attgtaaaag ggcaatgagt catcttaaac cagagagtac tttagaggaa   1020
aaactgagag cctgtcaaga ggtaggatca ccaggatata aaatgcagtt gttagcagaa   1080
gctcttacaa gggttcagac agttcaaaca agaggatcta gaccaacgtg tttcaattgt   1140
aaaaaaccag gccacttggc caaacaatgt agagaagcaa agagatgtaa caactgtgga   1200
aaacctggtc acttagctgc taattgctgg caaagaggta aaaaaacccc gggaaacggg   1260
aagatggggc cagctgcagc cccggtaaac caagtgcagc aaatggtgcc atctgcacct   1320
ccaatggaag acaggaaatt gttagattta taa                                1353
```

<210> SEQ ID NO 22
<211> LENGTH: 450
<212> TYPE: PRT
<213> ORGANISM: Feline immunodeficiency virus

<400> SEQUENCE: 22

```
Met Gly Asn Gly Gln Gly Arg Asp Trp Lys Thr Ala Val Lys Arg Cys
  1               5                  10                  15

Ser Asn Val Ala Val Gly Val Gly Ser Lys Ser Arg Lys Phe Gly Glu
             20                  25                  30

Gly Asn Phe Arg Trp Ala Ile Arg Met Ala Asn Val Thr Thr Gly Arg
         35                  40                  45

Glu Pro Gly Asp Ile Pro Glu Asn Leu Glu Gln Leu Arg Ser Ile Ile
     50                  55                  60

Cys Asp Leu His Asp Arg Glu Gln Tyr Gly Ser Ser Lys Glu Ile
 65                  70                  75                  80

Asp Met Ala Ile Thr Thr Leu Lys Val Phe Ala Val Ala Gly Ile Leu
                 85                  90                  95

Asn Met Thr Val Ser Thr Ala Ala Ala Glu His Met Tyr Ala Gln
             100                 105                 110

Met Gly Leu Asp Thr Arg Pro Ser Ile Lys Glu Ser Gly Gly Lys Glu
         115                 120                 125

Glu Gly Pro Pro Gln Ala Tyr Pro Ile Gln Thr Val Asn Gly Ala Pro
     130                 135                 140

Gln Tyr Val Ala Leu Asp Pro Lys Met Val Ser Ile Phe Met Glu Lys
145                 150                 155                 160

Ala Arg Glu Gly Leu Gly Gly Glu Glu Val Gln Leu Trp Phe Thr Ala
                 165                 170                 175

Phe Ser Ala Asn Leu Thr Ser Thr Asp Met Ala Thr Leu Ile Met Ser
             180                 185                 190

Ala Pro Gly Cys Ala Ala Asp Lys Glu Ile Leu Asp Glu Thr Leu Lys
         195                 200                 205

Gln Met Thr Ala Glu Tyr Asp Arg Thr His Pro Pro Asp Gly Pro Arg
     210                 215                 220

Pro Leu Pro Tyr Phe Thr Ala Ala Glu Ile Met Gly Ile Gly Leu Thr
225                 230                 235                 240

Gln Glu Gln Gln Ala Glu Pro Arg Phe Ala Pro Ala Arg Met Gln Cys
                 245                 250                 255

Arg Ala Trp Tyr Leu Glu Ala Leu Gly Lys Leu Ala Ala Ile Lys Ala
             260                 265                 270

Lys Ser Pro Arg Ala Val Gln Leu Lys Gln Gly Ala Lys Glu Asp Tyr
         275                 280                 285
```

-continued

```
Ser Ser Phe Ile Asp Arg Leu Phe Ala Gln Ile Asp Gln Glu Gln Asn
    290                 295                 300

Thr Ala Glu Val Lys Leu Tyr Leu Lys Gln Ser Leu Ser Ile Ala Asn
305                 310                 315                 320

Ala Asn Pro Asp Cys Lys Arg Ala Met Ser His Leu Lys Pro Glu Ser
            325                 330                 335

Thr Leu Glu Glu Lys Leu Arg Ala Cys Gln Glu Val Gly Ser Pro Gly
        340                 345                 350

Tyr Lys Met Gln Leu Leu Ala Glu Ala Leu Thr Arg Val Gln Thr Val
            355                 360                 365

Gln Thr Arg Gly Ser Arg Pro Thr Cys Phe Asn Cys Lys Lys Pro Gly
    370                 375                 380

His Leu Ala Lys Gln Cys Arg Glu Ala Lys Arg Cys Asn Asn Cys Gly
385                 390                 395                 400

Lys Pro Gly His Leu Ala Ala Asn Cys Trp Gln Arg Gly Lys Lys Thr
            405                 410                 415

Pro Gly Asn Gly Lys Met Gly Pro Ala Ala Ala Pro Val Asn Gln Val
        420                 425                 430

Gln Gln Met Val Pro Ser Ala Pro Pro Met Glu Asp Arg Lys Leu Leu
            435                 440                 445

Asp Leu
    450

<210> SEQ ID NO 23
<211> LENGTH: 450
<212> TYPE: PRT
<213> ORGANISM: Feline immunodeficiency virus

<400> SEQUENCE: 23

Met Gly Asn Gly Gln Gly Arg Asp Trp Lys Ala Ala Val Lys Arg Cys
1               5                   10                  15

Ser Asn Val Ala Val Gly Val Gly Ser Lys Ser Arg Lys Phe Gly Glu
            20                  25                  30

Gly Asn Phe Arg Trp Ala Ile Arg Met Ala Asn Val Thr Thr Gly Arg
        35                  40                  45

Glu Pro Gly Asp Ile Pro Glu Asn Leu Glu Gln Leu Arg Ser Ile Ile
    50                  55                  60

Cys Asp Leu His Asn Arg Arg Glu Gln Tyr Gly Ser Ser Lys Glu Ile
65                  70                  75                  80

Asp Met Ala Ile Thr Thr Leu Lys Val Phe Ala Val Ala Gly Ile Leu
                85                  90                  95

Asn Met Thr Val Ser Thr Ala Ala Ala Glu His Met Tyr Ala Gln
            100                 105                 110

Met Gly Leu Asp Thr Arg Pro Ser Ile Lys Glu Ser Gly Gly Lys Glu
        115                 120                 125

Glu Gly Pro Pro Gln Ala Tyr Pro Ile Gln Thr Val Asn Gly Ala Pro
    130                 135                 140

Gln Tyr Val Ala Leu Asp Pro Lys Met Val Ser Ile Phe Met Glu Lys
145                 150                 155                 160

Ala Arg Glu Gly Leu Gly Gly Glu Glu Val Gln Leu Trp Phe Thr Ala
                165                 170                 175

Phe Ser Ala Asn Leu Thr Ser Thr Asp Met Ala Thr Leu Ile Met Ser
            180                 185                 190

Ala Pro Gly Cys Ala Ala Asp Lys Glu Ile Leu Asp Glu Thr Leu Lys
        195                 200                 205
```

Gln Ile Thr Ala Asp Tyr Asp Arg Thr His Pro Pro Asp Gly Pro Arg
    210                 215                 220

Pro Leu Pro Tyr Phe Thr Ala Ala Glu Ile Met Gly Ile Gly Leu Thr
225                 230                 235                 240

Gln Glu Gln Gln Ala Glu Pro Arg Phe Ala Pro Ala Arg Met Gln Cys
                245                 250                 255

Arg Ala Trp Tyr Leu Glu Ala Leu Gly Arg Leu Ala Ala Ile Lys Ala
            260                 265                 270

Lys Pro Pro Arg Ala Val Gln Leu Lys Gln Gly Ala Lys Glu Asp Tyr
        275                 280                 285

Ser Ser Phe Ile Asp Arg Leu Phe Ala Gln Ile Asp Gln Glu Gln Asn
    290                 295                 300

Thr Ala Glu Val Lys Leu Tyr Leu Lys Gln Ser Leu Ser Ile Ala Asn
305                 310                 315                 320

Ala Asn Pro Asp Cys Lys Arg Ala Met Ser His Leu Lys Pro Glu Ser
                325                 330                 335

Thr Leu Glu Glu Lys Leu Arg Ala Cys Gln Glu Val Gly Ser Pro Gly
            340                 345                 350

Tyr Lys Met Gln Leu Leu Ala Glu Ala Leu Thr Arg Val Gln Thr Val
        355                 360                 365

Gln Thr Arg Gly Ser Arg Pro Thr Cys Phe Asn Cys Lys Lys Pro Gly
    370                 375                 380

His Leu Ala Lys Gln Cys Arg Glu Ala Lys Arg Cys Asn Asn Cys Gly
385                 390                 395                 400

Lys Pro Gly His Leu Ala Ala Asn Cys Trp Gln Arg Gly Lys Lys Pro
                405                 410                 415

Pro Gly Asn Gly Lys Met Gly Pro Ala Ala Pro Val Asn Gln Val
            420                 425                 430

Gln Gln Met Val Pro Ser Ala Pro Pro Met Glu Asp Arg Lys Leu Leu
        435                 440                 445

Asp Leu
    450

<210> SEQ ID NO 24
<211> LENGTH: 450
<212> TYPE: PRT
<213> ORGANISM: Feline immunodeficiency virus

<400> SEQUENCE: 24

Met Gly Asn Gly Gln Gly Arg Asp Trp Lys Ala Ala Val Lys Arg Cys
1               5                   10                  15

Ser Asn Val Ala Val Gly Val Gly Ser Lys Ser Arg Lys Phe Gly Glu
            20                  25                  30

Gly Asn Phe Arg Trp Ala Ile Arg Met Ala Asn Val Thr Thr Gly Arg
        35                  40                  45

Glu Pro Gly Asp Ile Pro Glu Asn Leu Glu Gln Leu Arg Leu Ile Ile
    50                  55                  60

Cys Asp Leu His Asp Arg Arg Glu Gln Tyr Gly Ser Ser Lys Glu Ile
65                  70                  75                  80

Asp Met Ala Ile Thr Thr Leu Lys Val Phe Ala Val Ala Gly Ile Leu
                85                  90                  95

Asn Met Thr Val Ser Thr Ala Ala Ala Glu His Met Tyr Ala Gln
            100                 105                 110

Met Gly Leu Asp Thr Arg Pro Ser Ile Lys Glu Ser Gly Gly Lys Glu

```
            115                 120                 125
Glu Gly Pro Pro Gln Ala Tyr Pro Ile Gln Thr Val Asn Gly Ala Pro
    130                 135                 140

Gln Tyr Val Ala Leu Asp Pro Lys Met Val Ser Ile Phe Met Glu Lys
145                 150                 155                 160

Ala Arg Glu Gly Leu Gly Gly Glu Val Gln Leu Trp Phe Thr Ala
                165                 170                 175

Phe Ser Ala Asn Leu Thr Ser Thr Asp Met Ala Thr Leu Ile Met Ser
            180                 185                 190

Ala Pro Gly Cys Ala Ala Asp Lys Glu Ile Leu Asp Glu Thr Leu Lys
        195                 200                 205

Gln Ile Thr Ala Asp Tyr Asp Arg Thr His Pro Pro Asp Gly Pro Arg
    210                 215                 220

Pro Leu Pro Tyr Phe Thr Ala Ala Glu Ile Met Gly Ile Gly Leu Thr
225                 230                 235                 240

Gln Glu Gln Gln Ala Glu Pro Arg Phe Ala Pro Ala Arg Met Gln Cys
                245                 250                 255

Arg Ala Trp Tyr Leu Glu Ala Leu Gly Arg Leu Ala Ala Ile Lys Ala
            260                 265                 270

Lys Pro Pro Arg Ala Val Gln Leu Lys Gln Gly Ala Lys Glu Asp Tyr
        275                 280                 285

Ser Ser Phe Ile Asp Arg Leu Phe Ala Gln Ile Asp Gln Glu Gln Asn
    290                 295                 300

Thr Ala Glu Val Lys Leu Tyr Leu Lys Gln Ser Leu Ser Ile Ala Asn
305                 310                 315                 320

Ala Asn Pro Asp Cys Lys Arg Ala Met Ser His Leu Lys Pro Glu Ser
                325                 330                 335

Thr Leu Glu Glu Lys Leu Arg Ala Cys Gln Glu Val Gly Ser Pro Gly
            340                 345                 350

Tyr Lys Met Gln Leu Leu Ala Glu Ala Leu Thr Arg Val Gln Thr Val
        355                 360                 365

Gln Thr Arg Gly Ser Arg Pro Thr Cys Phe Asn Cys Lys Lys Pro Gly
    370                 375                 380

His Leu Ala Lys Gln Cys Arg Glu Ala Lys Arg Cys Asn Asn Cys Gly
385                 390                 395                 400

Lys Pro Gly His Leu Ala Ala Asn Cys Trp Gln Arg Gly Lys Lys Thr
                405                 410                 415

Pro Gly Asn Gly Lys Met Gly Pro Ala Ala Pro Val Asn Gln Val
            420                 425                 430

Gln Gln Met Val Pro Ser Ala Pro Pro Met Glu Asp Arg Lys Leu Leu
        435                 440                 445

Asp Leu
    450

<210> SEQ ID NO 25
<211> LENGTH: 449
<212> TYPE: PRT
<213> ORGANISM: Feline immunodeficiency virus

<400> SEQUENCE: 25

Met Gly Asn Gly Gln Gly Arg Asp Trp Lys Thr Ala Val Lys Arg Cys
1               5                   10                  15

Ser Asn Val Ala Val Gly Val Gly Ser Lys Ser Arg Lys Phe Gly Glu
            20                  25                  30
```

```
Gly Asn Phe Arg Trp Ala Ile Arg Met Ala Asn Val Thr Gly Arg
         35                  40                  45

Glu Pro Gly Asp Ile Pro Glu Asn Leu Glu Gln Leu Arg Ser Ile Ile
 50                  55                  60

Cys Asp Leu His Asn Arg Arg Glu Gln Tyr Gly Ser Ser Lys Glu Ile
 65                  70                  75                  80

Asp Met Ala Ile Thr Thr Leu Lys Val Phe Ala Val Ala Gly Ile Leu
                 85                  90                  95

Asn Met Thr Val Ser Thr Ala Ala Ala Glu His Met Tyr Ala Gln
             100                 105                 110

Met Gly Leu Asp Thr Arg Pro Ser Ile Lys Glu Ser Gly Gly Lys Glu
         115                 120                 125

Glu Gly Pro Pro Gln Ala Tyr Pro Ile Gln Thr Val Asn Gly Ala Pro
130                 135                 140

Gln Tyr Val Ala Leu Asp Pro Lys Met Val Ser Ile Phe Met Glu Lys
145                 150                 155                 160

Ala Arg Glu Gly Leu Gly Gly Glu Val Gln Leu Trp Phe Thr Ala
                 165                 170                 175

Phe Ser Ala Asn Leu Thr Ser Thr Asp Met Ala Thr Leu Ile Met Ser
             180                 185                 190

Ala Pro Gly Cys Ala Ala Asp Lys Glu Ile Leu Asp Glu Thr Leu Lys
         195                 200                 205

Gln Ile Thr Ala Asp Tyr Asp Arg Thr His Pro Pro Asp Gly Pro Arg
210                 215                 220

Pro Leu Pro Tyr Phe Thr Ala Ala Glu Ile Met Gly Ile Gly Leu Thr
225                 230                 235                 240

Gln Glu Gln Gln Ala Glu Pro Arg Phe Ala Pro Ala Arg Met Gln Cys
                 245                 250                 255

Arg Ala Trp Tyr Leu Glu Ala Leu Gly Arg Leu Ala Ala Ile Lys Ala
             260                 265                 270

Lys Pro Pro Ala Val Gln Leu Lys Gln Gly Ala Lys Glu Asp Tyr Ser
         275                 280                 285

Ser Phe Ile Asp Arg Leu Phe Ala Gln Ile Asp Gln Glu Gln Asn Thr
290                 295                 300

Ala Glu Val Lys Leu Tyr Leu Lys Gln Ser Leu Ser Ile Ala Asn Ala
305                 310                 315                 320

Asn Pro Asp Cys Lys Arg Ala Met Ser His Leu Lys Pro Glu Ser Thr
                 325                 330                 335

Leu Glu Glu Lys Leu Arg Ala Cys Gln Glu Val Gly Ser Pro Gly Tyr
             340                 345                 350

Lys Met Gln Leu Leu Ala Glu Ala Leu Thr Arg Val Gln Thr Val Gln
         355                 360                 365

Thr Arg Gly Ser Arg Pro Thr Cys Phe Asn Cys Lys Lys Pro Gly His
370                 375                 380

Leu Ala Lys Gln Cys Arg Glu Ala Lys Arg Cys Asn Asn Cys Gly Lys
385                 390                 395                 400

Pro Gly His Leu Ala Ala Asn Cys Trp Gln Arg Gly Lys Lys Thr Pro
                 405                 410                 415

Gly Asn Gly Lys Met Gly Pro Ala Ala Pro Val Asn Gln Val Gln
             420                 425                 430

Gln Met Val Pro Ser Ala Pro Pro Met Glu Asp Arg Lys Leu Leu Asp
         435                 440                 445

Leu
```

<210> SEQ ID NO 26
<211> LENGTH: 450
<212> TYPE: PRT
<213> ORGANISM: Feline immunodeficiency virus

<400> SEQUENCE: 26

```
Met Gly Asn Gly Gln Gly Arg Asp Trp Lys Thr Ala Ile Lys Arg Cys
1               5                   10                  15

Ser Asn Val Ala Val Gly Val Glu Ser Lys Ser Arg Lys Phe Glu Lys
            20                  25                  30

Glu Asn Phe Arg Trp Ala Ile Lys Met Ala Asn Val Thr Thr Gly Arg
        35                  40                  45

Glu Pro Gly Asp Ile Pro Glu Asn Leu Glu Gln Leu Arg Ser Ile Ile
    50                  55                  60

Cys Asp Leu His Asp Arg Arg Glu Gln Tyr Gly Ser Ser Lys Glu Ile
65                  70                  75                  80

Asp Met Ala Ile Thr Thr Leu Lys Val Phe Ala Val Ala Gly Ile Leu
                85                  90                  95

Asn Met Thr Val Ser Thr Ala Ala Ala Glu His Met Tyr Ala Gln
            100                 105                 110

Met Gly Leu Asp Thr Arg Pro Ser Ile Lys Glu Ser Gly Gly Lys Glu
        115                 120                 125

Glu Gly Pro Pro Gln Ala Tyr Pro Ile Gln Thr Val Asn Gly Ala Pro
    130                 135                 140

Gln Tyr Val Ala Leu Asp Pro Lys Met Val Ser Ile Phe Met Glu Lys
145                 150                 155                 160

Ala Arg Glu Gly Leu Gly Gly Glu Glu Val Gln Leu Trp Phe Thr Ala
                165                 170                 175

Phe Ser Ala Asn Leu Thr Ser Thr Asp Met Ala Thr Leu Ile Met Ser
            180                 185                 190

Ala Pro Gly Cys Ala Ala Asp Lys Glu Ile Leu Asp Glu Thr Leu Lys
        195                 200                 205

Gln Met Thr Ala Glu Tyr Asp Arg Thr His Pro Pro Asp Gly Pro Arg
    210                 215                 220

Pro Leu Pro Tyr Phe Thr Ala Ala Glu Ile Met Gly Ile Gly Leu Thr
225                 230                 235                 240

Gln Glu Gln Gln Ala Glu Pro Arg Phe Ala Pro Ala Arg Met Gln Cys
                245                 250                 255

Arg Ala Trp Tyr Leu Glu Ala Leu Gly Lys Leu Ala Ala Ile Lys Ala
            260                 265                 270

Lys Ser Pro Arg Ala Val Gln Leu Lys Gln Gly Ala Lys Glu Asp Tyr
        275                 280                 285

Ser Ser Phe Ile Asp Arg Leu Phe Ala Gln Ile Asp Gln Glu Gln Asn
    290                 295                 300

Thr Ala Glu Val Lys Leu Tyr Leu Lys Gln Ser Leu Ser Ile Ala Asn
305                 310                 315                 320

Ala Asn Pro Asp Cys Lys Arg Ala Met Ser His Leu Lys Pro Glu Ser
                325                 330                 335

Thr Leu Glu Glu Lys Leu Arg Ala Cys Gln Glu Val Gly Ser Pro Gly
            340                 345                 350

Tyr Lys Met Gln Leu Leu Ala Glu Ala Leu Thr Arg Val Gln Thr Val
        355                 360                 365

Gln Thr Arg Gly Ser Arg Pro Thr Cys Phe Asn Cys Lys Lys Pro Gly
```

```
                370             375             380
His Leu Ala Lys Gln Cys Arg Glu Ala Lys Cys Asn Asn Cys Gly
385                 390                 395                 400

Lys Pro Gly His Leu Ala Ala Asn Cys Trp Gln Arg Gly Lys Lys Thr
                405                 410                 415

Pro Gly Asn Gly Lys Met Gly Pro Ala Ala Pro Val Asn Gln Val
                420                 425                 430

Gln Gln Met Val Pro Ser Ala Pro Pro Met Glu Asp Arg Lys Leu Leu
        435                 440                 445

Asp Leu
    450

<210> SEQ ID NO 27
<211> LENGTH: 450
<212> TYPE: PRT
<213> ORGANISM: Feline immunodeficiency virus

<400> SEQUENCE: 27

Met Gly Asn Gly Gln Gly Arg Asp Trp Lys Thr Ala Val Lys Arg Cys
1               5                   10                  15

Ser Asn Val Ala Val Gly Val Gly Ser Lys Ser Arg Lys Phe Gly Glu
                20                  25                  30

Gly Asn Phe Arg Trp Ala Ile Arg Met Ala Asn Val Thr Thr Gly Arg
            35                  40                  45

Glu Pro Gly Asp Ile Pro Glu Asn Leu Glu Gln Leu Arg Ser Ile Ile
    50                  55                  60

Cys Asp Leu His Asp Arg Glu Gln Tyr Gly Ser Ser Lys Glu Ile
65                  70                  75                  80

Asp Met Ala Ile Thr Thr Leu Lys Val Phe Ala Val Ala Gly Val Leu
                85                  90                  95

Asn Met Thr Val Ser Thr Ala Ala Ala Glu His Met Tyr Ala Gln
                100                 105                 110

Met Gly Leu Asp Thr Arg Pro Ser Ile Lys Glu Ser Gly Gly Lys Glu
            115                 120                 125

Glu Gly Pro Pro Gln Ala Tyr Pro Ile Gln Thr Val Asn Gly Ala Pro
    130                 135                 140

Gln Tyr Val Ala Leu Asp Pro Lys Met Val Ser Ile Phe Met Glu Lys
145                 150                 155                 160

Ala Arg Glu Gly Leu Gly Gly Glu Glu Val Gln Leu Trp Phe Thr Ala
                165                 170                 175

Phe Ser Ala Asn Leu Thr Ser Thr Asp Met Ala Thr Leu Ile Met Ser
            180                 185                 190

Ala Pro Gly Cys Ala Ala Asp Lys Glu Ile Leu Asp Glu Thr Leu Lys
        195                 200                 205

Gln Met Thr Ala Glu Tyr Asp Arg Thr His Pro Pro Asp Gly Pro Arg
    210                 215                 220

Pro Leu Pro Tyr Phe Thr Ala Ala Glu Ile Met Gly Ile Gly Leu Thr
225                 230                 235                 240

Gln Glu Gln Gln Ala Glu Pro Arg Phe Ala Pro Ala Arg Met Gln Cys
                245                 250                 255

Arg Ala Trp Tyr Leu Glu Ala Leu Gly Lys Leu Ala Ala Ile Lys Ala
            260                 265                 270

Lys Ser Pro Arg Ala Val Gln Leu Lys Gln Gly Ala Lys Glu Asp Tyr
        275                 280                 285
```

```
Ser Ser Phe Ile Asp Arg Leu Phe Ala Gln Ile Asp Gln Glu Gln Asn
    290                 295                 300
Thr Ala Glu Val Lys Leu Tyr Leu Lys Gln Ser Leu Ser Ile Ala Asn
305                 310                 315                 320
Ala Asn Pro Asp Cys Lys Arg Ala Met Ser His Leu Lys Pro Glu Ser
                325                 330                 335
Thr Leu Glu Glu Lys Leu Arg Ala Cys Gln Glu Val Gly Ser Pro Gly
            340                 345                 350
Tyr Lys Met Gln Leu Leu Ala Glu Ala Leu Thr Arg Val Gln Thr Val
        355                 360                 365
Gln Thr Arg Gly Ser Arg Pro Thr Cys Phe Asn Cys Lys Lys Pro Gly
    370                 375                 380
His Leu Ala Lys Gln Cys Arg Glu Ala Lys Arg Cys Asn Asn Cys Gly
385                 390                 395                 400
Lys Pro Gly His Leu Ala Ala Asn Cys Trp Gln Arg Gly Lys Lys Thr
                405                 410                 415
Pro Gly Asn Gly Lys Met Gly Pro Ala Ala Ala Pro Val Asn Gln Val
            420                 425                 430
Gln Gln Met Val Pro Ser Ala Pro Pro Met Glu Asp Arg Lys Leu Leu
        435                 440                 445
Asp Leu
    450

<210> SEQ ID NO 28
<211> LENGTH: 450
<212> TYPE: PRT
<213> ORGANISM: Feline immunodeficiency virus

<400> SEQUENCE: 28

Met Gly Asn Gly Gln Gly Arg Asp Trp Lys Thr Ala Val Lys Arg Cys
1               5                   10                  15
Ser Asn Val Ala Val Gly Val Gly Ser Lys Ser Arg Lys Phe Gly Glu
            20                  25                  30
Gly Asn Phe Arg Trp Ala Ile Arg Met Ala Asn Val Thr Thr Gly Arg
        35                  40                  45
Glu Pro Gly Asp Ile Pro Glu Asn Leu Glu Gln Leu Arg Ser Ile Ile
    50                  55                  60
Cys Asp Leu His Asp Arg Arg Glu Gln Tyr Gly Ser Ser Lys Glu Ile
65                  70                  75                  80
Asp Met Ala Ile Thr Thr Leu Lys Val Phe Ala Val Ala Gly Ile Leu
                85                  90                  95
Asn Met Thr Val Ser Thr Ala Ala Ala Glu His Met Tyr Ala Gln
            100                 105                 110  Gln
Met Gly Leu Asp Thr Arg Pro Ser Ile Lys Glu Ser Gly Gly Lys Glu
        115                 120                 125
Glu Gly Pro Pro Gln Ala Tyr Pro Ile Gln Thr Val Asn Gly Ala Pro
    130                 135                 140
Gln Tyr Val Ala Leu Asp Pro Lys Met Val Ser Ile Phe Met Glu Lys
145                 150                 155                 160
Ala Arg Glu Gly Leu Gly Gly Glu Glu Val Gln Leu Trp Phe Thr Ala
                165                 170                 175
Phe Ser Ala Asn Leu Thr Ser Thr Asp Met Ala Thr Leu Ile Met Ser
            180                 185                 190
Ala Pro Gly Cys Ala Ala Asp Lys Glu Ile Leu Asp Glu Thr Leu Lys
        195                 200                 205
```

```
Gln Met Thr Ala Glu Tyr Asp Arg Thr His Pro Pro Asp Gly Pro Arg
    210                 215                 220

Pro Leu Pro Tyr Phe Thr Ala Ala Glu Ile Met Gly Ile Gly Leu Thr
225                 230                 235                 240

Gln Glu Gln Gln Ala Glu Pro Arg Phe Ala Pro Ala Arg Met Gln Cys
                245                 250                 255

Arg Ala Trp Tyr Leu Glu Ala Leu Gly Lys Leu Ala Ala Ile Lys Ala
            260                 265                 270

Lys Ser Pro Arg Ala Val Gln Leu Lys Gln Gly Ala Lys Glu Asn Tyr
        275                 280                 285

Ser Ser Phe Ile Asp Arg Leu Phe Ala Gln Ile Asp Gln Glu Gln Asn
    290                 295                 300

Thr Ala Glu Val Lys Leu Tyr Leu Lys Gln Ser Leu Ser Ile Ala Asn
305                 310                 315                 320

Ala Asn Pro Asp Cys Lys Arg Ala Met Ser His Leu Lys Pro Glu Ser
                325                 330                 335

Thr Leu Glu Glu Lys Leu Arg Ala Cys Gln Glu Val Gly Ser Pro Gly
            340                 345                 350

Tyr Lys Met Gln Leu Leu Ala Glu Ala Leu Thr Arg Val Gln Thr Val
        355                 360                 365

Gln Thr Arg Gly Ser Arg Ser Thr Cys Phe Asn Cys Lys Lys Pro Gly
    370                 375                 380

His Leu Ala Lys Gln Cys Arg Glu Ala Lys Arg Cys Asn Asn Cys Gly
385                 390                 395                 400

Lys Pro Gly His Leu Ala Ala Asn Cys Trp Gln Arg Gly Lys Lys Thr
                405                 410                 415

Pro Gly Asn Gly Lys Met Gly Pro Ala Ala Pro Val Asn Gln Val
            420                 425                 430

Gln Gln Met Val Pro Ser Ala Pro Pro Met Glu Asp Arg Lys Leu Leu
        435                 440                 445

Asp Leu
    450

<210> SEQ ID NO 29
<211> LENGTH: 450
<212> TYPE: PRT
<213> ORGANISM: Feline immunodeficiency virus

<400> SEQUENCE: 29

Met Gly Asn Gly Gln Gly Arg Asp Trp Lys Thr Ala Val Lys Arg Cys
1               5                   10                  15

Ser Asn Val Ala Val Gly Val Gly Ser Lys Ser Arg Lys Phe Gly Glu
            20                  25                  30

Gly Asn Phe Arg Trp Ala Ile Arg Met Ala Asn Val Thr Thr Gly Arg
        35                  40                  45

Glu Pro Gly Asp Ile Pro Glu Asn Leu Glu Gln Leu Arg Ser Ile Ile
    50                  55                  60

Cys Asp Leu His Asp Arg Arg Glu Gln Tyr Gly Ser Ser Lys Glu Ile
65                  70                  75                  80

Asp Met Ala Ile Thr Thr Leu Lys Val Phe Ala Val Ala Gly Ile Leu
                85                  90                  95

Asn Met Thr Val Ser Thr Ala Ala Ala Glu His Met Tyr Ala Gln
            100                 105                 110

Met Gly Leu Asp Thr Arg Pro Ser Ile Lys Glu Ser Gly Gly Lys Glu
```

```
            115                 120                 125
Glu Gly Pro Pro Gln Ala Tyr Pro Ile Gln Thr Val Asn Gly Ala Pro
130                 135                 140

Gln Tyr Val Ala Leu Asp Pro Lys Met Val Ser Ile Phe Met Glu Lys
145                 150                 155                 160

Ala Arg Glu Gly Leu Gly Gly Glu Glu Val Gln Leu Trp Phe Thr Ala
                165                 170                 175

Phe Ser Ala Asn Leu Thr Ser Thr Asp Met Ala Thr Leu Ile Met Ser
                180                 185                 190

Ala Pro Gly Cys Ala Ala Asp Lys Glu Ile Leu Asp Glu Thr Leu Lys
            195                 200                 205

Gln Met Thr Ala Glu Tyr Asp Arg Thr His Pro Pro Asp Gly Pro Arg
210                 215                 220

Pro Leu Pro Tyr Phe Thr Ala Ala Glu Ile Met Gly Ile Gly Leu Thr
225                 230                 235                 240

Gln Glu Gln Gln Ala Glu Pro Arg Phe Ala Pro Ala Arg Met Gln Cys
                245                 250                 255

Arg Ala Trp Tyr Leu Glu Ala Leu Gly Lys Leu Ala Ala Ile Lys Ala
                260                 265                 270

Lys Ser Pro Arg Ala Val Gln Leu Lys Gln Gly Ala Lys Glu Asp Tyr
            275                 280                 285

Ser Ser Phe Ile Asp Arg Leu Phe Ala Gln Ile Asp Gln Glu Gln Asn
290                 295                 300

Thr Ala Glu Val Lys Leu Tyr Leu Lys Gln Ser Leu Ser Ile Ala Asn
305                 310                 315                 320

Ala Asn Pro Asp Cys Lys Arg Ala Met Ser His Leu Lys Pro Glu Ser
                325                 330                 335

Thr Leu Glu Glu Lys Leu Arg Ala Cys Gln Glu Val Gly Ser Pro Gly
                340                 345                 350

Tyr Lys Met Gln Leu Leu Ala Glu Ala Leu Thr Arg Val Gln Thr Val
            355                 360                 365

Gln Thr Arg Gly Ser Arg Pro Met Cys Phe Asn Cys Lys Lys Pro Gly
370                 375                 380

His Leu Ala Lys Gln Cys Arg Glu Ala Lys Arg Cys Asn Asn Cys Gly
385                 390                 395                 400

Lys Pro Gly His Leu Ala Ala Asn Cys Trp Gln Arg Gly Lys Lys Thr
                405                 410                 415

Pro Gly Asn Gly Lys Met Gly Pro Ala Ala Pro Val Asn Gln Val
                420                 425                 430

Gln Gln Met Val Pro Ser Ala Pro Pro Met Glu Asp Arg Lys Leu Leu
            435                 440                 445

Asp Leu
    450

<210> SEQ ID NO 30
<211> LENGTH: 450
<212> TYPE: PRT
<213> ORGANISM: Feline immunodeficiency virus

<400> SEQUENCE: 30

Met Gly Asn Gly Gln Gly Arg Asp Trp Lys Thr Ala Val Lys Arg Cys
1               5                   10                  15

Ser Asn Val Ala Val Gly Val Gly Ser Lys Ser Arg Lys Phe Gly Glu
                20                  25                  30
```

Gly Asn Phe Arg Trp Ala Ile Arg Met Ala Asn Val Thr Gly Arg
         35                  40                  45

Glu Pro Gly Asp Ile Pro Glu Asn Leu Glu Gln Leu Arg Ser Ile Ile
 50                  55                  60

Cys Asp Leu His Asp Arg Arg Glu Gln Tyr Gly Ser Ser Lys Glu Ile
 65                  70                  75                  80

Asp Met Ala Ile Thr Thr Leu Lys Val Phe Ala Val Ala Gly Ile Leu
                 85                  90                  95

Asn Met Thr Val Ser Thr Ala Ala Ala Glu His Met Tyr Ala Gln
                100                 105                 110

Met Gly Leu Asp Thr Arg Pro Ser Ile Lys Glu Ser Gly Gly Lys Glu
            115                 120                 125

Glu Gly Pro Pro Gln Ala Tyr Pro Ile Gln Thr Val Asn Gly Ala Pro
    130                 135                 140

Gln Tyr Val Ala Leu Asp Pro Lys Met Val Ser Ile Phe Met Glu Lys
145                 150                 155                 160

Ala Arg Glu Gly Leu Gly Gly Glu Val Gln Leu Trp Phe Thr Ala
                165                 170                 175

Phe Ser Thr Asn Leu Thr Ser Thr Asp Met Ala Thr Leu Ile Met Ser
                180                 185                 190

Ala Pro Gly Cys Ala Ala Asp Lys Glu Ile Leu Asp Glu Thr Leu Lys
            195                 200                 205

Gln Met Thr Ala Glu Tyr Asp Arg Thr His Pro Pro Asp Gly Pro Arg
    210                 215                 220

Pro Leu Pro Tyr Phe Thr Ala Glu Ile Met Gly Ile Gly Leu Thr
225                 230                 235                 240

Gln Glu Gln Gln Ala Glu Pro Arg Phe Ala Pro Ala Arg Met Gln Cys
                245                 250                 255

Arg Ala Trp Tyr Leu Glu Ala Leu Gly Lys Leu Ala Ala Ile Lys Ala
            260                 265                 270

Lys Ser Pro Arg Ala Val Gln Leu Lys Gln Gly Ala Lys Glu Asp Tyr
    275                 280                 285

Ser Ser Phe Ile Asp Arg Leu Phe Ala Gln Ile Asp Gln Glu Gln Asn
290                 295                 300

Thr Ala Glu Val Lys Leu Tyr Leu Lys Gln Ser Leu Ser Ile Ala Asn
305                 310                 315                 320

Ala Asn Pro Asp Cys Lys Arg Ala Met Ser His Leu Lys Pro Glu Ser
            325                 330                 335

Thr Leu Glu Glu Lys Leu Arg Ala Cys Gln Glu Val Gly Ser Pro Gly
        340                 345                 350

Tyr Lys Met Gln Leu Leu Ala Glu Ala Leu Thr Arg Val Gln Thr Val
    355                 360                 365

Gln Thr Arg Gly Ser Arg Pro Thr Cys Phe Asn Cys Lys Lys Pro Gly
    370                 375                 380

His Leu Ala Lys Gln Cys Arg Glu Ala Lys Arg Cys Asn Asn Cys Gly
385                 390                 395                 400

Lys Pro Gly His Leu Ala Ala Asn Cys Trp Gln Arg Gly Lys Lys Thr
                405                 410                 415

Pro Gly Asn Gly Lys Met Gly Pro Ala Ala Pro Val Asn Gln Val
            420                 425                 430

Gln Gln Met Val Pro Ser Ala Pro Pro Met Glu Asp Arg Lys Leu Leu
    435                 440                 445

Asp Leu

450

<210> SEQ ID NO 31
<211> LENGTH: 450
<212> TYPE: PRT
<213> ORGANISM: Feline immunodeficiency virus

<400> SEQUENCE: 31

Met Gly Asn Gly Gln Gly Arg Asp Trp Lys Thr Ala Val Lys Arg Cys
1               5                   10                  15

Ser Asn Val Ala Val Gly Val Gly Ser Lys Ser Arg Lys Phe Gly Glu
                20                  25                  30

Gly Asn Phe Arg Trp Ala Ile Arg Met Ala Asn Val Thr Thr Gly Arg
            35                  40                  45

Glu Pro Gly Asp Ile Pro Glu Asn Leu Glu Gln Leu Arg Ser Ile Ile
    50                  55                  60

Cys Asp Leu His Asp Arg Arg Glu Gln Tyr Gly Ser Ser Lys Glu Ile
65                  70                  75                  80

Asp Met Ala Ile Thr Thr Leu Lys Val Phe Ala Val Ala Gly Ile Leu
                85                  90                  95

Asn Met Thr Val Ser Thr Ala Ala Ala Glu His Met Tyr Ala Gln
                100                 105                 110

Met Gly Leu Asp Thr Arg Pro Ser Ile Lys Glu Ser Gly Gly Lys Glu
            115                 120                 125

Glu Gly Pro Pro Gln Ala Tyr Pro Ile Gln Thr Val Asn Gly Ala Pro
    130                 135                 140

Gln Tyr Val Ala Leu Asp Pro Lys Met Val Ser Ile Phe Met Glu Lys
145                 150                 155                 160

Ala Arg Glu Gly Leu Gly Gly Glu Val Gln Leu Trp Phe Thr Ala
                165                 170                 175

Phe Ser Ala Asn Leu Thr Ser Thr Asp Met Ala Thr Leu Ile Met Ser
            180                 185                 190

Ala Pro Gly Cys Ala Ala Asp Lys Glu Ile Leu Asp Glu Thr Leu Lys
    195                 200                 205

Gln Met Thr Ala Glu Tyr Asp Arg Thr His Pro Pro Asp Gly Pro Arg
    210                 215                 220

Pro Leu Pro Tyr Phe Thr Ala Ala Glu Ile Met Gly Ile Gly Leu Thr
225                 230                 235                 240

Gln Glu Gln Gln Ala Glu Pro Arg Phe Ala Pro Ala Arg Met Gln Cys
                245                 250                 255

Arg Ala Trp Tyr Leu Glu Ala Leu Gly Lys Leu Ala Ala Ile Lys Ala
            260                 265                 270

Lys Ser Pro Arg Ala Val Gln Leu Lys Gln Gly Ala Lys Glu Asp Tyr
    275                 280                 285

Ser Ser Phe Ile Asp Arg Leu Phe Ala Gln Ile Asp Gln Glu Gln Asn
290                 295                 300

Thr Ala Glu Val Lys Leu Tyr Leu Lys Gln Ser Leu Ser Ile Ala Asn
305                 310                 315                 320

Ala Asn Pro Asp Cys Lys Arg Ala Met Ser His Leu Lys Pro Glu Ser
                325                 330                 335

Thr Leu Glu Glu Lys Leu Arg Ala Cys Gln Glu Val Gly Ser Pro Gly
            340                 345                 350

Tyr Lys Met Gln Leu Leu Ala Glu Ala Leu Thr Arg Val Gln Thr Val
    355                 360                 365

```
Gln Thr Arg Gly Ser Arg Pro Thr Cys Phe Asn Cys Lys Lys Pro Gly
    370                 375                 380
His Leu Ala Lys Gln Cys Arg Glu Ala Lys Arg Cys Asn Asn Cys Gly
385                 390                 395                 400
Lys Pro Gly His Leu Ala Ala Asn Cys Trp Gln Arg Gly Lys Lys Thr
                405                 410                 415
Pro Gly Asn Gly Lys Met Gly Pro Ala Ala Pro Val Asn Gln Val
                420                 425                 430
Gln Gln Met Val Pro Ser Ala Pro Met Glu Asp Arg Lys Leu Leu
            435                 440                 445
Asp Leu
    450

<210> SEQ ID NO 32
<211> LENGTH: 450
<212> TYPE: PRT
<213> ORGANISM: Feline immunodeficiency virus

<400> SEQUENCE: 32

Met Gly Asn Gly Gln Gly Arg Asp Trp Lys Thr Ala Val Lys Arg Cys
1               5                   10                  15
Ser Asn Val Ala Val Gly Val Gly Ser Lys Ser Arg Lys Phe Gly Glu
                20                  25                  30
Gly Asn Phe Arg Trp Ala Ile Arg Met Ala Asn Val Thr Thr Gly Arg
            35                  40                  45
Glu Pro Gly Asp Ile Pro Glu Asn Leu Glu Gln Leu Arg Ser Ile Ile
    50                  55                  60
Cys Asp Leu His Gly Arg Arg Glu Gln Tyr Gly Ser Ser Lys Glu Ile
65                  70                  75                  80
Asp Met Ala Ile Thr Thr Leu Lys Val Phe Ala Val Ala Gly Ile Leu
                85                  90                  95
Asn Met Thr Val Ser Thr Ala Ala Ala Glu His Met Tyr Ala Gln
                100                 105                 110
Met Gly Leu Asp Thr Arg Pro Ser Ile Lys Glu Gly Gly Gly Lys Glu
            115                 120                 125
Glu Gly Pro Pro Gln Ala Tyr Pro Ile Gln Thr Val Asn Gly Ala Pro
    130                 135                 140
Gln Tyr Val Ala Leu Asp Pro Lys Met Val Ser Ile Phe Met Glu Lys
145                 150                 155                 160
Ala Arg Glu Gly Leu Gly Gly Glu Glu Val Gln Leu Trp Phe Thr Ala
                165                 170                 175
Phe Ser Ala Asn Leu Thr Ser Thr Asp Met Ala Thr Leu Ile Met Ser
            180                 185                 190
Ala Pro Gly Cys Ala Ala Asp Lys Glu Ile Leu Asp Glu Thr Leu Lys
        195                 200                 205
Gln Met Thr Ala Glu Tyr Asp Arg Thr His Pro Pro Asp Gly Pro Arg
    210                 215                 220
Pro Leu Pro Tyr Phe Thr Ala Ala Glu Ile Met Gly Ile Gly Leu Thr
225                 230                 235                 240
Gln Glu Gln Gln Ala Glu Pro Arg Phe Ala Pro Ala Arg Met Gln Cys
                245                 250                 255
Arg Ala Trp Tyr Leu Glu Ala Leu Gly Lys Leu Ala Ala Ile Lys Ala
            260                 265                 270
Lys Ser Pro Arg Ala Val Gln Leu Lys Gln Gly Ala Lys Glu Asp Tyr
        275                 280                 285
```

-continued

```
Ser Ser Phe Ile Asp Arg Leu Phe Ala Gln Ile Asp Gln Glu Gln Asn
    290                 295                 300

Thr Ala Glu Val Lys Leu Tyr Leu Lys Gln Ser Leu Ser Ile Ala Asn
305                 310                 315                 320

Ala Asn Pro Asp Cys Lys Arg Ala Met Ser His Leu Lys Pro Glu Ser
                325                 330                 335

Thr Leu Glu Glu Lys Leu Arg Ala Cys Gln Glu Val Gly Ser Pro Gly
            340                 345                 350

Tyr Lys Met Gln Leu Leu Ala Glu Ala Leu Thr Arg Val Gln Thr Val
        355                 360                 365

Gln Thr Arg Gly Ser Arg Pro Thr Cys Phe Asn Cys Lys Lys Pro Gly
370                 375                 380

His Leu Ala Lys Gln Cys Arg Glu Ala Lys Arg Cys Asn Asn Cys Gly
385                 390                 395                 400

Lys Pro Gly His Leu Ala Ala Asn Cys Trp Gln Arg Gly Lys Lys Thr
                405                 410                 415

Pro Gly Asn Gly Lys Met Gly Pro Ala Ala Ala Pro Val Asn Gln Val
            420                 425                 430

Gln Gln Met Val Pro Ser Ala Pro Pro Met Glu Asp Arg Lys Leu Leu
        435                 440                 445

Asp Leu
    450

<210> SEQ ID NO 33
<211> LENGTH: 450
<212> TYPE: PRT
<213> ORGANISM: Feline immunodeficiency virus

<400> SEQUENCE: 33

Met Gly Asn Gly Gln Gly Arg Asp Trp Lys Thr Ala Val Lys Arg Cys
1               5                   10                  15

Ser Asn Val Ala Val Gly Val Gly Ser Lys Ser Arg Lys Phe Gly Glu
            20                  25                  30

Gly Asn Phe Arg Trp Ala Ile Arg Met Ala Asn Val Thr Thr Gly Arg
        35                  40                  45

Glu Pro Gly Asp Ile Pro Glu Asn Leu Glu Gln Leu Arg Ser Ile Ile
50                  55                  60

Cys Asp Leu His Gly Arg Arg Glu Gln Tyr Gly Ser Ser Lys Glu Ile
65                  70                  75                  80

Asp Met Ala Ile Thr Thr Leu Lys Val Phe Val Val Ala Gly Ile Leu
                85                  90                  95

Asn Met Thr Val Ser Thr Ala Ala Ala Ala Glu His Met Tyr Ala Gln
            100                 105                 110

Met Gly Leu Asp Thr Arg Pro Ser Ile Lys Glu Gly Gly Gly Lys Glu
        115                 120                 125

Glu Gly Pro Pro Gln Ala Tyr Pro Ile Gln Thr Val Asn Gly Ala Pro
130                 135                 140

Gln Tyr Val Ala Leu Asp Pro Lys Met Val Ser Ile Phe Met Glu Lys
145                 150                 155                 160

Ala Arg Glu Gly Leu Gly Gly Glu Glu Val Gln Leu Trp Phe Thr Ala
                165                 170                 175

Phe Ser Ala Asn Leu Thr Ser Thr Asp Met Ala Thr Leu Ile Met Ser
            180                 185                 190

Ala Pro Gly Cys Ala Ala Asp Lys Glu Ile Leu Asp Glu Thr Leu Lys
```

```
            195                 200                 205
Gln Met Thr Ala Glu Tyr Asp Arg Thr His Pro Pro Asp Gly Pro Arg
210                 215                 220

Pro Leu Pro Tyr Phe Thr Ala Glu Ile Met Gly Ile Gly Leu Thr
225                 230                 235                 240

Gln Glu Gln Gln Ala Glu Pro Arg Phe Ala Pro Ala Arg Met Gln Cys
                245                 250                 255

Arg Ala Trp Tyr Leu Glu Ala Leu Gly Lys Leu Ala Ala Ile Lys Ala
            260                 265                 270

Lys Ser Pro Arg Ala Val Gln Leu Lys Gln Gly Ala Lys Glu Asp Tyr
        275                 280                 285

Ser Ser Phe Ile Asp Arg Leu Phe Ala Gln Ile Asp Gln Glu Gln Asn
    290                 295                 300

Thr Ala Glu Val Lys Leu Tyr Leu Lys Gln Ser Leu Ser Ile Ala Asn
305                 310                 315                 320

Ala Asn Pro Asp Cys Lys Arg Ala Met Ser His Leu Lys Pro Glu Ser
                325                 330                 335

Thr Leu Glu Glu Lys Leu Arg Ala Cys Gln Glu Val Gly Ser Pro Gly
            340                 345                 350

Tyr Lys Met Gln Leu Leu Ala Glu Ala Leu Thr Arg Val Gln Thr Val
        355                 360                 365

Gln Thr Arg Gly Ser Arg Pro Thr Cys Phe Asn Cys Lys Lys Pro Gly
    370                 375                 380

His Leu Ala Lys Gln Cys Arg Glu Ala Lys Arg Cys Asn Asn Cys Gly
385                 390                 395                 400

Lys Pro Gly His Leu Ala Ala Asn Cys Trp Gln Arg Gly Lys Lys Thr
                405                 410                 415

Pro Gly Asn Gly Lys Met Gly Pro Ala Ala Ala Pro Val Asn Gln Val
            420                 425                 430

Gln Gln Met Val Pro Ser Ala Pro Pro Met Glu Asp Arg Lys Leu Leu
        435                 440                 445

Asp Leu
    450

<210> SEQ ID NO 34
<211> LENGTH: 450
<212> TYPE: PRT
<213> ORGANISM: Feline immunodeficiency virus

<400> SEQUENCE: 34

Met Gly Asn Gly Gln Gly Arg Asp Trp Lys Thr Ala Val Lys Arg Cys
1               5                   10                  15

Ser Asn Val Ala Val Gly Val Gly Ser Lys Ser Arg Lys Phe Gly Glu
            20                  25                  30

Gly Asn Phe Arg Trp Ala Ile Arg Met Ala Asn Val Thr Thr Gly Arg
        35                  40                  45

Glu Pro Gly Asp Ile Pro Glu Asn Leu Glu Gln Leu Arg Ser Ile Ile
    50                  55                  60

Cys Asp Leu His Gly Arg Arg Glu Gln Tyr Gly Ser Ser Lys Glu Ile
65                  70                  75                  80

Asp Met Ala Ile Thr Thr Leu Lys Val Phe Ala Val Ala Gly Ile Leu
                85                  90                  95

Asn Met Thr Val Ser Thr Ala Ala Ala Glu His Met Tyr Ala Gln
            100                 105                 110
```

```
Met Gly Leu Asp Thr Arg Pro Ser Ile Lys Glu Gly Gly Lys Glu
            115                 120                 125
Glu Gly Pro Pro Gln Ala Tyr Pro Ile Gln Thr Val Asn Gly Ala Pro
        130                 135                 140
Gln Tyr Val Ala Leu Asp Pro Lys Met Val Ser Ile Phe Met Glu Lys
145                 150                 155                 160
Ala Arg Glu Gly Leu Gly Gly Glu Val Gln Leu Trp Phe Thr Ala
                165                 170                 175
Phe Ser Ala Asn Leu Thr Ser Thr Asp Met Ala Thr Leu Ile Met Ser
                180                 185                 190
Ala Pro Gly Cys Ala Ala Asp Lys Glu Ile Leu Asp Glu Thr Leu Lys
                195                 200                 205
Gln Met Thr Ala Glu Tyr Asp Arg Thr His Pro Pro Asp Gly Pro Arg
            210                 215                 220
Pro Leu Pro Tyr Phe Thr Ala Ala Glu Ile Met Gly Ile Gly Leu Thr
225                 230                 235                 240
Gln Glu Gln Gln Ala Glu Pro Arg Phe Ala Pro Ala Arg Met Gln Cys
                245                 250                 255
Arg Ala Trp Tyr Leu Glu Ala Leu Gly Lys Leu Ala Ala Ile Lys Ala
                260                 265                 270
Lys Ser Pro Arg Ala Val Gln Leu Lys Gln Gly Ala Lys Glu Asp Tyr
            275                 280                 285
Ser Ser Phe Ile Asp Arg Leu Phe Ala Gln Ile Asp Gln Glu Gln Asn
            290                 295                 300
Thr Ala Glu Val Lys Leu Tyr Leu Lys Gln Ser Leu Ser Ile Ala Asn
305                 310                 315                 320
Ala Asn Pro Asp Cys Lys Arg Ala Met Ser His Leu Lys Pro Glu Ser
                325                 330                 335
Thr Leu Glu Glu Lys Leu Arg Ala Cys Gln Glu Val Gly Ser Pro Gly
            340                 345                 350
Tyr Lys Met Gln Leu Leu Ala Glu Ala Leu Thr Arg Val Gln Thr Val
            355                 360                 365
Gln Thr Arg Gly Ser Arg Pro Thr Cys Phe Asn Cys Lys Lys Pro Gly
        370                 375                 380
His Leu Ala Lys Gln Cys Arg Glu Ala Lys Arg Cys Asn Asn Cys Gly
385                 390                 395                 400
Lys Pro Gly His Leu Ala Ala Asn Cys Trp Gln Arg Gly Lys Lys Thr
                405                 410                 415
Pro Gly Asn Gly Lys Met Gly Pro Ala Ala Pro Val Asn Gln Val
            420                 425                 430
Gln Gln Met Val Pro Ser Ala Pro Met Glu Gly Arg Lys Leu Leu
        435                 440                 445
Asp Leu
    450

<210> SEQ ID NO 35
<211> LENGTH: 450
<212> TYPE: PRT
<213> ORGANISM: Feline immunodeficiency virus

<400> SEQUENCE: 35

Met Gly Asn Gly Gln Gly Arg Asp Trp Lys Thr Ala Val Lys Arg Cys
1               5                   10                  15
Ser Asn Val Ala Val Gly Val Gly Ser Lys Ser Arg Lys Phe Gly Glu
                20                  25                  30
```

```
Gly Asn Phe Arg Trp Ala Ile Arg Met Ala Asn Val Thr Thr Gly Arg
            35                  40                  45

Glu Pro Gly Asp Ile Pro Glu Asn Leu Glu Gln Leu Arg Ser Ile Ile
 50                  55                  60

Cys Asp Leu His Gly Arg Arg Glu Gln Tyr Gly Ser Ser Lys Glu Ile
 65                  70                  75                  80

Asp Met Ala Ile Thr Thr Leu Lys Val Phe Ala Val Ala Gly Ile Leu
                     85                  90                  95

Asn Met Thr Val Ser Thr Ala Ala Ala Glu His Met Tyr Ala Gln
                 100                 105                 110

Met Gly Leu Asp Thr Arg Pro Ser Ile Lys Glu Gly Gly Lys Glu
            115                 120                 125

Glu Gly Pro Pro Gln Ala Tyr Pro Ile Gln Thr Val Asn Gly Ala Pro
 130                 135                 140

Gln Tyr Val Ala Leu Asp Pro Lys Met Val Ser Ile Phe Met Glu Lys
145                 150                 155                 160

Ala Arg Glu Gly Leu Gly Gly Glu Glu Val Gln Leu Trp Phe Thr Ala
                165                 170                 175

Phe Ser Ala Asn Leu Thr Ser Thr Asp Met Ala Thr Leu Ile Met Ser
                180                 185                 190

Ala Pro Gly Cys Ala Ala Asp Lys Glu Ile Leu Asp Glu Thr Leu Lys
            195                 200                 205

Gln Met Thr Ala Glu Tyr Asp Arg Thr His Pro Pro Asp Gly Pro Arg
210                 215                 220

Pro Leu Pro Tyr Phe Thr Ala Ala Glu Ile Met Gly Ile Gly Leu Thr
225                 230                 235                 240

Gln Glu Gln Gln Ala Glu Pro Arg Phe Ala Pro Ala Arg Met Gln Cys
                245                 250                 255

Arg Ala Trp Tyr Leu Glu Ala Leu Gly Lys Leu Ala Ala Ile Lys Ala
                260                 265                 270

Lys Ser Pro Arg Ala Val Gln Leu Lys Gln Gly Ala Lys Glu Asp Tyr
            275                 280                 285

Ser Ser Phe Ile Asp Arg Leu Phe Ala Gln Ile Asp Gln Glu Gln Asn
            290                 295                 300

Thr Ala Glu Val Lys Leu Tyr Leu Lys Gln Ser Leu Ser Ile Ala Asn
305                 310                 315                 320

Ala Asn Pro Asp Cys Lys Arg Ala Met Ser His Leu Lys Pro Glu Ser
                325                 330                 335

Thr Leu Glu Glu Lys Leu Arg Ala Cys Gln Glu Val Gly Ser Pro Gly
            340                 345                 350

Tyr Lys Met Gln Leu Leu Ala Glu Ala Leu Thr Arg Val Gln Thr Val
            355                 360                 365

Gln Thr Arg Gly Ser Arg Pro Thr Cys Phe Asn Cys Lys Lys Pro Gly
 370                 375                 380

His Leu Ala Lys Gln Cys Arg Glu Ala Lys Arg Cys Asn Asn Cys Gly
385                 390                 395                 400

Lys Pro Gly His Leu Ala Ala Asn Cys Trp Gln Arg Gly Lys Lys Thr
                405                 410                 415

Pro Gly Asn Gly Lys Met Gly Pro Ala Ala Pro Val Asn Gln Val
            420                 425                 430

Gln Gln Met Val Pro Ser Ala Pro Pro Met Gly Asp Arg Lys Leu Leu
            435                 440                 445
```

Asp Leu
    450

<210> SEQ ID NO 36
<211> LENGTH: 450
<212> TYPE: PRT
<213> ORGANISM: Feline immunodeficiency virus

<400> SEQUENCE: 36

Met Gly Asn Gly Gln Gly Arg Asp Trp Lys Thr Ala Val Lys Arg Cys
1               5                   10                  15

Ser Asn Val Ala Val Gly Val Gly Ser Lys Ser Arg Lys Phe Gly Glu
            20                  25                  30

Gly Asn Phe Arg Trp Ala Ile Arg Met Ala Asn Val Thr Thr Gly Arg
        35                  40                  45

Glu Pro Gly Asp Ile Pro Glu Asn Leu Glu Gln Leu Arg Ser Ile Ile
    50                  55                  60

Cys Asp Leu His Gly Arg Arg Glu Gln Tyr Gly Ser Ser Lys Glu Ile
65                  70                  75                  80

Asp Met Ala Ile Thr Thr Leu Lys Val Phe Ala Val Ala Gly Ile Leu
                85                  90                  95

Asn Met Thr Val Ser Thr Ala Ala Ala Glu His Met Tyr Ala Gln
            100                 105                 110

Met Gly Leu Asp Thr Arg Pro Ser Ile Lys Glu Gly Gly Lys Glu
        115                 120                 125

Glu Gly Pro Pro Gln Ala Tyr Pro Ile Gln Thr Val Asn Gly Ala Pro
    130                 135                 140

Gln Tyr Val Ala Leu Asp Pro Lys Met Val Ser Ile Phe Met Glu Lys
145                 150                 155                 160

Ala Arg Glu Gly Leu Gly Gly Glu Glu Val Gln Leu Trp Phe Thr Ala
                165                 170                 175

Phe Ser Ala Asn Leu Thr Ser Thr Asp Met Ala Thr Leu Ile Met Ser
            180                 185                 190

Ala Pro Gly Cys Ala Ala Asp Lys Glu Ile Leu Asp Glu Thr Leu Lys
        195                 200                 205

Gln Met Thr Ala Glu Tyr Asp Arg Thr His Pro Pro Asp Gly Pro Arg
    210                 215                 220

Pro Leu Pro Tyr Phe Thr Ala Ala Glu Ile Met Gly Ile Gly Leu Thr
225                 230                 235                 240

Gln Glu Gln Gln Ala Glu Pro Arg Phe Ala Pro Ala Arg Met Arg Cys
                245                 250                 255

Arg Ala Trp Tyr Leu Glu Ala Leu Gly Lys Leu Ala Ala Ile Lys Ala
            260                 265                 270

Lys Ser Pro Arg Ala Val Gln Leu Lys Gln Gly Ala Lys Glu Asp Tyr
        275                 280                 285

Ser Ser Phe Ile Asp Arg Leu Phe Ala Gln Ile Asp Gln Glu Gln Asn
    290                 295                 300

Thr Ala Glu Val Lys Leu Tyr Leu Lys Gln Ser Leu Ser Ile Ala Asn
305                 310                 315                 320

Ala Asn Pro Asp Cys Lys Arg Ala Met Ser His Leu Lys Pro Glu Ser
                325                 330                 335

Thr Leu Glu Glu Lys Leu Arg Ala Cys Gln Glu Val Gly Ser Pro Gly
            340                 345                 350

Tyr Lys Met Gln Leu Leu Ala Glu Ala Leu Thr Arg Val Gln Thr Val
        355                 360                 365

```
Gln Thr Arg Gly Ser Arg Pro Thr Cys Phe Asn Cys Lys Lys Pro Gly
    370                 375                 380

His Leu Ala Lys Gln Cys Arg Glu Ala Lys Arg Cys Asn Asn Cys Gly
385                 390                 395                 400

Lys Pro Gly His Leu Ala Ala Asn Cys Trp Gln Arg Gly Lys Lys Thr
                405                 410                 415

Pro Gly Asn Gly Lys Met Gly Pro Ala Ala Pro Val Asn Gln Val
                420                 425                 430

Gln Gln Met Val Pro Ser Ala Pro Met Glu Asp Arg Lys Leu Leu
        435                 440                 445

Asp Leu
    450

<210> SEQ ID NO 37
<211> LENGTH: 450
<212> TYPE: PRT
<213> ORGANISM: Feline immunodeficiency virus

<400> SEQUENCE: 37

Met Gly Asn Gly Gln Gly Arg Asp Trp Lys Thr Ala Val Lys Arg Cys
1               5                   10                  15

Ser Asn Val Ala Val Gly Val Gly Ser Lys Ser Arg Lys Phe Gly Glu
                20                  25                  30

Gly Asn Phe Arg Trp Ala Ile Arg Met Ala Asn Val Thr Thr Gly Arg
            35                  40                  45

Glu Pro Gly Asp Ile Pro Glu Asn Leu Glu Gln Leu Arg Ser Ile Ile
    50                  55                  60

Cys Asp Leu His Gly Arg Arg Glu Gln Tyr Gly Ser Ser Lys Glu Ile
65                  70                  75                  80

Asp Met Ala Ile Thr Thr Leu Lys Val Phe Ala Val Ala Gly Ile Leu
                85                  90                  95

Asn Met Thr Val Ser Thr Ala Ala Ala Glu His Met Tyr Ala Gln
                100                 105                 110

Met Gly Leu Asp Thr Arg Pro Ser Ile Lys Glu Gly Gly Lys Glu
            115                 120                 125

Glu Gly Pro Pro Gln Ala Tyr Pro Ile Gln Thr Val Asn Gly Ala Pro
    130                 135                 140

Gln Tyr Val Ala Leu Asp Pro Lys Met Val Ser Ile Phe Met Glu Lys
145                 150                 155                 160

Ala Arg Glu Gly Leu Gly Gly Glu Glu Val Gln Leu Trp Phe Thr Ala
                165                 170                 175

Phe Ser Ala Asn Leu Thr Ser Thr Asp Met Ala Thr Leu Ile Met Ser
            180                 185                 190

Ala Pro Gly Cys Ala Ala Asp Lys Glu Ile Leu Asp Glu Thr Leu Lys
        195                 200                 205

Gln Met Thr Ala Glu Tyr Asp Arg Thr His Pro Pro Asp Gly Pro Arg
    210                 215                 220

Pro Leu Pro Tyr Phe Thr Ala Glu Ile Met Gly Ile Gly Leu Thr
225                 230                 235                 240

Gln Glu Gln Gln Ala Glu Pro Arg Phe Ala Pro Ala Arg Met Gln Cys
                245                 250                 255

Arg Ala Trp Tyr Leu Glu Ala Leu Gly Lys Leu Ala Ala Ile Lys Ala
            260                 265                 270

Lys Ser Pro Arg Ala Val Gln Leu Lys Gln Gly Ala Lys Glu Asp Tyr
```

```
                275                 280                 285
Ser Ser Phe Ile Asp Arg Leu Phe Ala Gln Ile Asp Gln Glu Gln Asn
290                 295                 300

Thr Ala Glu Val Lys Leu Tyr Leu Lys Gln Ser Leu Ser Ile Ala Asn
305                 310                 315                 320

Ala Asn Pro Asp Cys Lys Arg Ala Met Ser His Leu Lys Pro Glu Ser
                325                 330                 335

Thr Leu Glu Glu Lys Leu Arg Ala Cys Gln Glu Val Gly Ser Pro Gly
                340                 345                 350

Tyr Lys Met Gln Leu Leu Ala Glu Ala Leu Thr Arg Val Gln Thr Val
                355                 360                 365

Gln Thr Arg Gly Ser Arg Pro Thr Cys Phe Asn Cys Lys Lys Pro Gly
                370                 375                 380

His Leu Ala Lys Gln Cys Arg Glu Ala Lys Arg Cys Asn Asn Cys Gly
385                 390                 395                 400

Lys Pro Gly His Leu Ala Ala Asn Cys Trp Gln Arg Gly Lys Lys Thr
                405                 410                 415

Pro Gly Asn Gly Lys Met Gly Pro Ala Ala Pro Val Asn Gln Val
                420                 425                 430

Gln Gln Met Val Pro Ser Ala Pro Pro Met Glu Asp Arg Lys Leu Leu
                435                 440                 445

Asp Leu
    450

<210> SEQ ID NO 38
<211> LENGTH: 450
<212> TYPE: PRT
<213> ORGANISM: Feline immunodeficiency virus

<400> SEQUENCE: 38

Met Gly Asn Gly Gln Gly Arg Asp Trp Lys Thr Ala Val Lys Arg Cys
1                   5                   10                  15

Ser Asn Val Ala Val Gly Val Gly Ser Lys Ser Arg Lys Phe Gly Glu
                20                  25                  30

Gly Asp Phe Arg Trp Ala Ile Arg Met Ala Asn Val Thr Thr Gly Arg
                35                  40                  45

Glu Pro Gly Asp Ile Pro Glu Asn Leu Glu Gln Leu Arg Ser Ile Ile
50                  55                  60

Cys Asp Leu His Gly Arg Arg Glu Gln Tyr Gly Ser Ser Lys Glu Ile
65                  70                  75                  80

Asp Met Ala Ile Thr Thr Leu Lys Val Phe Ala Val Ala Gly Ile Leu
                85                  90                  95

Asn Met Thr Val Ser Thr Ala Ala Ala Glu His Met Tyr Ala Gln
                100                 105                 110

Met Gly Leu Asp Thr Arg Pro Ser Ile Lys Glu Gly Gly Lys Glu
                115                 120                 125

Glu Gly Pro Pro Gln Ala Tyr Pro Ile Gln Thr Val Asn Gly Ala Pro
130                 135                 140

Gln Tyr Val Ala Leu Asp Pro Lys Met Val Ser Ile Phe Met Glu Lys
145                 150                 155                 160

Ala Arg Glu Gly Leu Gly Gly Glu Glu Val Gln Leu Trp Phe Thr Ala
                165                 170                 175

Phe Ser Ala Asn Leu Thr Ser Thr Asp Met Ala Thr Leu Ile Met Ser
                180                 185                 190
```

```
Ala Pro Gly Cys Ala Ala Asp Lys Glu Ile Leu Asp Glu Thr Leu Lys
            195                 200                 205
Gln Met Thr Ala Glu Tyr Asp Arg Thr His Pro Pro Asp Gly Pro Arg
        210                 215                 220
Pro Leu Pro Tyr Phe Thr Ala Glu Ile Met Gly Ile Gly Leu Thr
225                 230                 235                 240
Gln Glu Gln Gln Ala Glu Pro Arg Phe Ala Pro Ala Arg Met Gln Cys
                245                 250                 255
Arg Ala Trp Tyr Leu Glu Ala Leu Gly Lys Leu Ala Ala Ile Lys Ala
            260                 265                 270
Lys Ser Pro Arg Ala Val Gln Leu Lys Gln Gly Ala Lys Glu Asp Tyr
        275                 280                 285
Ser Ser Phe Ile Asp Arg Leu Phe Ala Gln Ile Asp Gln Glu Gln Asn
    290                 295                 300
Thr Ala Glu Val Lys Leu Tyr Leu Lys Gln Ser Leu Ser Ile Ala Asn
305                 310                 315                 320
Ala Asn Pro Asp Cys Lys Arg Ala Met Ser His Leu Lys Pro Glu Ser
                325                 330                 335
Thr Leu Glu Glu Lys Leu Arg Ala Cys Gln Glu Val Gly Ser Pro Gly
            340                 345                 350
Tyr Lys Met Gln Leu Leu Ala Glu Ala Leu Thr Arg Val Gln Thr Val
        355                 360                 365
Gln Thr Arg Gly Ser Arg Pro Thr Cys Phe Asn Cys Lys Lys Pro Gly
    370                 375                 380
His Leu Ala Lys Gln Cys Arg Glu Ala Lys Arg Cys Asn Asn Cys Gly
385                 390                 395                 400
Lys Pro Gly His Leu Ala Ala Asn Cys Trp Gln Arg Gly Lys Lys Thr
                405                 410                 415
Pro Gly Asn Gly Lys Met Gly Pro Ala Ala Ala Pro Val Asn Gln Val
            420                 425                 430
Gln Gln Met Ala Pro Ser Ala Pro Pro Met Glu Asp Arg Lys Leu Leu
        435                 440                 445
Asp Leu
    450

<210> SEQ ID NO 39
<211> LENGTH: 450
<212> TYPE: PRT
<213> ORGANISM: Feline immunodeficiency virus

<400> SEQUENCE: 39

Met Gly Asn Gly Gln Gly Arg Asp Trp Lys Thr Ala Val Lys Arg Cys
1               5                   10                  15
Ser Asn Val Ala Val Gly Val Gly Ser Lys Ser Arg Lys Phe Gly Glu
            20                  25                  30
Gly Asp Phe Arg Trp Ala Ile Arg Met Ala Asn Val Thr Thr Gly Arg
        35                  40                  45
Glu Pro Gly Asp Ile Pro Glu Asn Leu Glu Gln Leu Arg Ser Ile Ile
    50                  55                  60
Cys Asp Leu His Gly Arg Arg Glu Gln Tyr Gly Ser Ser Lys Glu Ile
65                  70                  75                  80
Asp Met Ala Ile Thr Thr Leu Lys Val Phe Ala Val Ala Gly Ile Leu
                85                  90                  95
Asn Met Thr Val Ser Thr Ala Ala Ala Glu His Met Tyr Ala Gln
            100                 105                 110
```

Met Gly Leu Asp Thr Arg Pro Ser Ile Lys Glu Gly Gly Lys Glu
            115                 120                 125

Glu Gly Pro Pro Gln Ala Tyr Pro Ile Gln Thr Val Asn Gly Ala Pro
        130                 135                 140

Gln Tyr Val Ala Leu Asp Pro Lys Met Val Ser Ile Phe Met Glu Lys
145                 150                 155                 160

Ala Arg Glu Gly Leu Gly Gly Glu Val Gln Leu Trp Phe Thr Ala
            165                 170                 175

Phe Ser Ala Asn Leu Thr Ser Thr Asp Met Ala Thr Leu Ile Met Ser
            180                 185                 190

Ala Pro Gly Cys Ala Ala Asp Lys Glu Ile Leu Asp Glu Thr Leu Lys
            195                 200                 205

Gln Met Thr Ala Glu Tyr Asp Arg Thr His Pro Pro Asp Gly Pro Arg
    210                 215                 220

Pro Leu Pro Tyr Phe Thr Ala Ala Glu Ile Met Gly Ile Gly Leu Thr
225                 230                 235                 240

Gln Glu Gln Gln Ala Glu Pro Arg Phe Ala Pro Ala Arg Met Gln Cys
                245                 250                 255

Arg Ala Trp Tyr Leu Glu Ala Leu Gly Lys Leu Ala Ala Ile Lys Ala
            260                 265                 270

Lys Ser Pro Arg Ala Val Gln Leu Lys Gln Gly Ala Lys Glu Asp Tyr
    275                 280                 285

Ser Ser Phe Ile Asp Arg Leu Phe Ala Gln Ile Asp Gln Glu Gln Asn
    290                 295                 300

Thr Ala Glu Val Lys Leu Tyr Leu Lys Gln Ser Leu Ser Ile Ala Asn
305                 310                 315                 320

Ala Asn Pro Asp Cys Lys Arg Ala Met Ser His Leu Lys Pro Glu Ser
                325                 330                 335

Thr Leu Glu Glu Lys Leu Arg Ala Cys Gln Glu Val Gly Ser Pro Gly
            340                 345                 350

Tyr Lys Met Gln Leu Leu Ala Glu Ala Leu Thr Arg Val Gln Thr Val
        355                 360                 365

Gln Thr Arg Gly Ser Arg Pro Thr Cys Phe Asn Cys Lys Lys Pro Gly
    370                 375                 380

His Leu Ala Lys Gln Cys Arg Glu Ala Lys Arg Cys Asn Asn Cys Gly
385                 390                 395                 400

Lys Pro Gly His Leu Ala Ala Asn Cys Trp Gln Arg Gly Lys Lys Thr
                405                 410                 415

Pro Gly Asn Gly Lys Met Gly Pro Ala Ala Pro Val Asn Gln Val
            420                 425                 430

Gln Gln Met Ala Pro Ser Ala Pro Met Glu Asp Arg Lys Leu Leu
        435                 440                 445

Asp Leu
    450

<210> SEQ ID NO 40
<211> LENGTH: 450
<212> TYPE: PRT
<213> ORGANISM: Feline immunodeficiency virus

<400> SEQUENCE: 40

Met Gly Asn Gly Gln Gly Arg Asp Trp Lys Thr Ala Val Lys Arg Cys
1               5                   10                  15

Ser Asn Val Ala Val Gly Val Gly Ser Lys Ser Arg Lys Phe Gly Glu

```
            20                  25                  30
Gly Asn Phe Arg Trp Ala Ile Arg Met Ala Asn Val Thr Thr Gly Arg
            35                  40                  45

Glu Pro Gly Asp Ile Pro Glu Asn Leu Glu Gln Leu Arg Ser Ile Ile
 50                  55                  60

Cys Asp Leu His Gly Arg Arg Glu Gln Tyr Gly Ser Ser Lys Glu Ile
 65                  70                  75                  80

Asp Met Ala Ile Thr Thr Leu Lys Val Phe Ala Val Ala Gly Ile Leu
                    85                  90                  95

Asn Met Thr Val Ser Thr Ala Ala Ala Glu His Met Tyr Ala Gln
                100                 105                 110

Met Gly Leu Asp Thr Arg Pro Ser Ile Lys Glu Gly Gly Lys Glu
                115                 120                 125

Glu Gly Pro Pro Gln Ala Tyr Pro Ile Gln Thr Val Asn Gly Ala Pro
            130                 135                 140

Gln Tyr Val Ala Leu Asp Pro Lys Met Val Ser Ile Phe Met Glu Lys
145                 150                 155                 160

Ala Arg Glu Gly Leu Gly Gly Glu Val Gln Leu Trp Phe Thr Ala
                165                 170                 175

Phe Ser Ala Asn Leu Thr Ser Thr Asp Met Ala Thr Leu Ile Met Ser
                180                 185                 190

Ala Pro Gly Cys Ala Ala Asp Lys Glu Ile Leu Asp Glu Thr Leu Lys
            195                 200                 205

Gln Met Thr Ala Glu Tyr Asp Arg Thr His Pro Pro Asp Gly Pro Arg
            210                 215                 220

Pro Leu Pro Tyr Phe Thr Ala Ala Glu Ile Met Gly Ile Gly Leu Thr
225                 230                 235                 240

Gln Glu Gln Gln Ala Glu Pro Arg Phe Ala Pro Ala Arg Met Gln Cys
                245                 250                 255

Arg Ala Trp Tyr Leu Glu Ala Leu Gly Lys Leu Ala Ala Ile Lys Ala
                260                 265                 270

Lys Ser Pro Arg Ala Val Gln Leu Lys Gln Gly Ala Lys Glu Asp Tyr
                275                 280                 285

Ser Ser Phe Thr Asp Arg Leu Phe Ala Gln Ile Asp Gln Glu Gln Asn
        290                 295                 300

Thr Ala Glu Val Lys Leu Tyr Leu Lys Gln Ser Leu Ser Ile Ala Asn
305                 310                 315                 320

Ala Asn Pro Asp Cys Lys Arg Ala Met Ser His Leu Lys Pro Glu Ser
                325                 330                 335

Thr Leu Glu Glu Lys Leu Arg Ala Cys Gln Glu Val Gly Ser Pro Gly
                340                 345                 350

Tyr Lys Met Gln Leu Leu Ala Glu Ala Leu Thr Arg Val Gln Thr Val
                355                 360                 365

Gln Thr Arg Gly Ser Arg Pro Thr Cys Phe Asn Cys Lys Lys Pro Gly
                370                 375                 380

His Leu Ala Lys Gln Cys Arg Glu Ala Lys Arg Cys Asn Asn Cys Gly
385                 390                 395                 400

Lys Pro Gly His Leu Ala Ala Asn Cys Trp Gln Arg Gly Lys Lys Thr
                405                 410                 415

Pro Gly Asn Gly Lys Met Gly Pro Ala Ala Pro Val Asn Gln Val
                420                 425                 430

Gln Gln Met Val Pro Ser Ala Pro Pro Met Glu Asp Arg Lys Leu Leu
                435                 440                 445
```

Asp Leu
    450

<210> SEQ ID NO 41
<211> LENGTH: 1353
<212> TYPE: DNA
<213> ORGANISM: Feline immunodeficiency virus

<400> SEQUENCE: 41

| | | | | | | |
|---|---|---|---|---|---|---|
| atggggaatg | gacagggggcg | agactggaag | acggccgtta | agagatgtag | taatgttgct | 60 |
| gtaggggtag | ggagtaagag | tagaaagttt | ggagaaggaa | actttaggtg | ggccataagg | 120 |
| atggctaatg | taactacagg | acgagaacct | ggtgatatac | cagagaattt | agaacagtta | 180 |
| agatcgatta | tttgtgattt | acatggcaga | agagaacaat | atggatctag | taaagaaatt | 240 |
| gatatggcaa | ttaccacttt | aaaagttttt | gcagtagctg | gaattttaaa | tatgactgtg | 300 |
| tctactgccg | cagcagctga | acacatgtat | gctcagatgg | gattagatac | cagaccatct | 360 |
| ataaaagaag | gtgggggaaa | agaagaagga | cctccacagg | cttatcctat | tcaaacagta | 420 |
| aatggagcac | cacagtatgt | agcccttgac | ccaaaaatgg | tgtccatctt | tatggaaaaa | 480 |
| gcaagagagg | ggctaggagg | tgaggaggtc | caactgtggt | tcacagcctt | ttctgctaat | 540 |
| ttaacttcaa | ctgatatggc | tacattaatt | atgtctgcgc | ctggctgtgc | agcagataaa | 600 |
| gagatcttag | atgaaacact | gaaacagatg | acagctgagt | atgatcgtac | tcatcctcct | 660 |
| gatgggccta | gaccgctgcc | ctatttcacc | gctgcggaga | ttatgggaat | aggattaact | 720 |
| caagaacaac | aagcggagcc | cagatttgca | ccagctagaa | tgcagtgtag | agcatggtat | 780 |
| cttgaagcac | taggaaagtt | ggcagccata | aaagctaaat | ctccccgagc | agtgcaattg | 840 |
| aagcaaggag | ctaaagagga | ttattcctca | tttatagata | gattatttgc | tcaaatagat | 900 |
| caagagcaga | acacagctga | agtaaagctg | tatttaaaac | aatctttgag | catagccaat | 960 |
| gctaacccag | attgtaaaag | ggcaatgagt | catcttaaac | cagagagtac | tttagaggaa | 1020 |
| aaactgagag | cctgtcaaga | ggtaggatca | ccaggatata | aaatgcagtt | gttagcagaa | 1080 |
| gctcttacaa | gggttcagac | agttcaaaca | agaggatcta | gaccaacgtg | tttcaattgt | 1140 |
| aaaaaaccag | gccacctggc | caaacaatgt | agagaagcaa | agagatgtaa | caactgtgga | 1200 |
| aaacctggtc | acttagctgc | taattgctgg | caaagaggta | aaaaaacccc | gggaaacggg | 1260 |
| aagatggggc | cagctgcagc | cccggtaaac | caagtgcagc | aaatggtgcc | atctgcacct | 1320 |
| ccaatggaag | acaggaaatt | gttagattta | taa | | | 1353 |

<210> SEQ ID NO 42
<211> LENGTH: 1353
<212> TYPE: DNA
<213> ORGANISM: Feline immunodeficiency virus

<400> SEQUENCE: 42

| | | | | | | |
|---|---|---|---|---|---|---|
| atggggaatg | gacagggggcg | agactggaag | acggccgtta | agagatgtag | taatgttgct | 60 |
| gtaggggtag | ggagtaagag | tagaaagttt | ggagaaggaa | actttaggtg | ggccataagg | 120 |
| atggctaatg | taactacagg | acgagaacct | ggtgatatac | cagagaattt | agaacagtta | 180 |
| agatcgatta | tttgtgattt | acatgacaga | agagaacaat | atggatctag | taaagaaatt | 240 |
| gatatggcaa | ttaccacttt | aaaagttttt | gcagtagctg | gaattttaaa | tatgactgtg | 300 |
| tctactgccg | cagcagctga | acacatgtat | gctcagatgg | gattagatac | cagaccatct | 360 |
| ataaagaaa | gtgggggaaa | agaagaagga | cctccacagg | cttatcctat | tcaaacagta | 420 |

```
aatggagcac cacagtatgt agcccttgac ccaaaaatgg tgtccatttt tatggaaaaa       480
gcaagagagg ggctaggagg tgaggaggtc caactgtggt tcacagcctt ttctgctaat       540
ttaacttcaa ctgatatggc tacattaatt atgtctgcgc ctggctgtgc agcagataaa       600
gagatcttag atgaaacact gaaacagatg acagctgagt atgatcgtac tcatcctcct       660
gatgggccta gaccgctgcc ctatttcacc gctgcggaga ttatgggaat aggattaact       720
caagaacaac aggcggagcc cagatttgca ccagctagaa tgcagtgtag agcatggtat       780
cttgaagcac taggaaagtt ggcagccata aaagctaaat ctccccgagc agtgcaatta       840
aagcaaggag ctaaagagga ttattcctca tttatagata gattatttgc tcaaatagat       900
caagagcaga acacagctga agtaaagctg tatttaaaac aatctttgag catagccaat       960
gctaacccag attgtaaaag ggcaatgagt catcttaaac cagagagtac tttagaggaa      1020
aaactgagag cctgtcaaga ggtaggatca ccaggatata aaatgcagtt gttagcagaa      1080
gctcttacaa gggttcagac agttcaaaca agaggatcta gaccaacgtg tttcaattgt      1140
aaaaaaccag gccacctggc caaacaatgt agagaagcaa agagatgtaa caactgtgga      1200
aaacctggtc acttagctgc taattgctgg caaagaggta aaaaaacccc gggaaacggg      1260
aagatggggc cagctgcagc cccggtaaac caagtgcagc aaatggtgcc atctgcacct      1320
ccaatggaag acaggaaatt gttagattta taa                                  1353

<210> SEQ ID NO 43
<211> LENGTH: 1353
<212> TYPE: DNA
<213> ORGANISM: Feline immunodeficiency virus

<400> SEQUENCE: 43
atggggaatg gacaggggcg agattggaaa atggccatta agagatgtag taatgttgct        60
gtaggagtag gggggaagag taaaaaattt ggagaaggga atttcagatg gccattaga       120 atggctaatg tatctacagg acgagaacct ggtgatatac cagagacttt agatcaacta       180
aggttggtta tttgcgattt acaagaaaga agagaaaaat ttggatctag caaagaaatt       240
gatatggcaa ttgtgacatt aaaagtcttt gcggtagcag acttttaaa tatgacggtg       300 tctactgctg ctgcagctga aaatatgtat tctcaaatgg gattagacac taggccatct       360
atgaaagaag caggtggaaa agaggaaggc cctccacagg catatcctat tcaaacagta       420
aatggagtac acaatatgt agcacttgac ccaaaaatgg tgtccatttt tatggaaaag       480
gcaagagaag gactaggagg tgaggaagtt caactatggt ttactgcctt ctctgcaaat       540
ttaacaccta ctgacatggc cacattaata atggccgcac cagggtgcgc tgcagataaa       600
gaaatattgg atgaaagctt aaagcaactg acagcagaat atgatcgcac acatcccct       660 gatgctccca gaccattacc ctattttact gcagcagaaa ttatgggtat aggattaact       720
caagaacaac aagcagaagc aagatttgca ccagctagga tgcagtgtag agcatggtat       780
ctcgaggcat taggaaaatt ggctgccata aaagctaagt ctcctcgagc tgtgcagtta       840
agacaaggag ctaaggaaga ttattcatcc tttatagaca gattgtttgc ccaaatagat       900
caagaacaaa atacagctga agttaagtta tatttaaaac agtcattgag catagctaat       960
gctaatgcag actgtaaaaa ggcaatgagc caccttaagc cagaaagtac cctagaagaa      1020
aagttgagag cttgtcaaga aataggctca ccaggatata aaatgcaact cttggcagaa      1080
gctcttacaa aagttcaagt agtgcaatca aaaggatctg accagtgtg tttttaattgt      1140
```

| | |
|---|---|
| aaaaaaccag gacatctagc aagacaatgt agagaagtga aaaaatgtaa taaatgtgga | 1200 |
| aaacctggtc atgtagctgc caattgttgg caaggaaata gaaagaattc gggaaactgg | 1260 |
| aaggcggggc gagctgcagc cccagtgaat caaatgcagc aagcagtaat gccatctgca | 1320 |
| cctccaatgg aggagaaact attggattta taa | 1353 |

<210> SEQ ID NO 44
<211> LENGTH: 1353
<212> TYPE: DNA
<213> ORGANISM: Feline immunodeficiency virus

<400> SEQUENCE: 44

| | |
|---|---|
| atggggaatg gacagggggcg agattggaaa atggccatta agagatgcag taatgttgct | 60 |
| gtaggagtag gggggaagag taaaaaattt ggagaaggga atttcagatg gccatcaga | 120 |
| atggctaatg tatctacagg acgagaacct ggtgatatac cagagacttt agatcaactg | 180 |
| aggttggtta tttgcgattt acaagaaaga agagaaaaat ttggatctag caaagaaatt | 240 |
| gatatggcaa ttaccaccct taaaagtttt tgcagtagtg gacttttaaa tatgacagtg | 300 |
| tctactgctg ctgcagctga aaatatgtat actcagatgg gattagacac tagaccatct | 360 |
| acaaaggaag ctggaggaaa agaggaaggc cctccacagg catatcctat tcaaacagta | 420 |
| aatggagcac acaatatgt agctcttgac ccaaaaatgg tgtctatttt catggaaaag | 480 |
| gcaagagaag ggttaggagg tgaagaagtt caactatggt tcacagccct ctctgcaaat | 540 |
| ttaacaccta ctgacatggc cacattaata atggccgcac cagggtgcgc tgcagataaa | 600 |
| gaaatattgg atgaaagctt aaagcaaata acagcagaat atgatcgtac acatccccct | 660 |
| gatggtccta gaccattacc atattttact gcggcagaga ttatgggtat aggattaact | 720 |
| caagaacaac aagcagaagc aagatttgca ccagctagga tgcagtgtag agcatggtat | 780 |
| cttgaggcat taggaaaatt ggccgccata aaagctaagt ctcctcgagc tgtacagtta | 840 |
| agacaaggag ctaaagaaga ttattcatcc tttatagaca gattgtttgc ccaaatagat | 900 |
| caagaacaaa atacagctga agttaagata tatctaaaaac agtcattaag catggctaat | 960 |
| gctaatgcag aatgcaaaaa ggcaatgagt catcttaagc cagaaagttc cctagaagaa | 1020 |
| aagttgagag cctgtcaaga gataggatcc ccaggatata aaatgcaact cttggcagaa | 1080 |
| gctcttacaa aagttcaagt agtgcaatca aaaggatcag gaccagtgtg tttttaattgt | 1140 |
| aaaaaaccgg gcatctagc aagacagtgt agagatgtga aaaaatgtaa taaatgtgga | 1200 |
| agacctggtc atttagctgc cagatgctgg cagggtggta aaaagaactc gggaaactgg | 1260 |
| aaggcggggc gagctgcagc cccagtaaac caagtgcagc aggcagtaat gccatctgca | 1320 |
| cctccaatgg aggagagact attggattta taa | 1353 |

<210> SEQ ID NO 45
<211> LENGTH: 1200
<212> TYPE: DNA
<213> ORGANISM: Feline immunodeficiency virus

<400> SEQUENCE: 45

| | |
|---|---|
| atggggaatg gacagggggcg agattggaaa atggccatta agagatgtag taatgttgct | 60 |
| gtaggagtag gggggaagag taaaaaattt ggagagggga atttaggtg gccataaga | 120 |
| atggctaatg tatctacagg acgagaacct ggtgatatac cagagacttt agatcaatta | 180 |
| aggttggtta tttgcgattt acaagaaaga agagaaaaat ttggatctag caaagaaatt | 240 |
| gacatggcaa ttacaacatt aaaagtcttt gcagtagtgg acttttaaa tatgacagtg | 300 |

```
tctactgctg ctgcagctga aaatatgtat actcagatgg gattagacac tagaccgtct    360
acaaaagaag cgggaggaaa agaggaaggc cctccacagg catatcctat tcaaacagta    420
aatggagcac cacaatatgt agcacttgac ccaaaaatgg tgtccatttt tatggaaaag    480
gcaagagagg gattaggagg tgaggaagtt caactatggt ttacagcctt ctctgcaaat    540
ttaacaccta ctgacatggc cacattaata atggccgcac ccgggtgcgc tgcagataaa    600
gaaatattgg atgaaagctt aaagcaattg acagcagaat atgatcggac aaatcccect    660 gatggtccta gaccattacc ctatttcact gcagcagaaa ttatgggtat aggattaact    720
caagaacaac aagcagaagc aagatttgca ccagctagga tgcaatgtag agcatggtat    780
cttgaggcat taggaaaatt agccgccata aaggctaaat ctcctcgagc tgtgcagtta    840
agacaaggag ctaaggaaga ttattcatcc tttatagaca gattgtttgc ccaaatagat    900
caagaacaaa atacagctga agttaagtta tatctaaaac agtcattaag catagctaat    960
gctaatgcag aatgcaaaaa ggcaatgagt catcttaagc cagaaagtac cctagaagaa   1020
aagttgagag cttgtcaaga gataggatcc ccaggatata aaatgcaact cttggcagaa   1080
gctcttacaa aagttcaagt agtgcaatca aaaggatcag gaccagtgtg ttttaattgt   1140
aaaaaaccag ggcatctagc aagacagtgt agagatgtga aaaaatgtaa taaatgtgga   1200
```

<210> SEQ ID NO 46
<211> LENGTH: 795
<212> TYPE: DNA
<213> ORGANISM: Feline immunodeficiency virus

<400> SEQUENCE: 46

```
tctacattaa aagtctttgc agtagcagga attttaaata tgacagtgtc tactgctgct     60
gcagctgaaa acatgtataa tcaaatggga ttagacacta gaccgtctac aagagaagca    120
ggaggaaaag aggaaggccc tccacaggca tatcctattc aaacagtaaa tggagcacct    180
caatatgtag cacttgaccc aaaaatggtg tcattttta tggaaaaagc aagagaagga    240
ttaggaggtg aggaagttca actatggttt actgccttct ctgcaaattt aacacctact    300
gacatggcca cattaataat ggccgcacca gggtgtgctg cagataaaga aatattagat    360
gaaagcttaa agcaattgac agcagaatat gatcgtacac atccccctga tgctcctaga    420
ccattaccct attttactgc agcagaaatt atgggtatag gattaactca agaacaacaa    480
gcagaagcaa gatttgcacc agctaggatg cagtgtagag catggtatct tgaggcatta    540
ggaaaattgg ccgccataaa agctaagtct cctcgagctg tgcagttaag acatggagct    600
aaggaggatt attcatcctt tatagacaga ttgtttgccc aaatagatca agaacaaaat    660
acagctgaag ttaaattata tttaaaacag tcattaagca tagctaatgc taatgcagaa    720
tgtaaaaaag caatgagtca ccttaagcca gaaagtaccc tagaagaaaa gttgagagct    780
tgtcaagaag tagga                                                     795
```

<210> SEQ ID NO 47
<211> LENGTH: 1353
<212> TYPE: DNA
<213> ORGANISM: Feline immunodeficiency virus
<220> FEATURE:
<221> NAME/KEY: misc_feature
<222> LOCATION: (612)..(612)
<223> OTHER INFORMATION: n = a, c, g, or t.

<400> SEQUENCE: 47

```
atggggaatg gtcaggggcg tgattggaaa atggccatta aaagatgtag taatgttgct      60
gtaggagtag gggggaggag taaaaaattt ggagaaggaa atttcagatg ggccattaga     120
atggctaacg tatctacagg acgagaacct ggtgatatac cagagacttt agatcaacta     180
aggttggtta tttgcgaatt acaagaaaga agagaaaaat ttggatctag caaagaattg     240
gacatggcaa ttactacatt aaaagtcttc gcggtagtag acttttaaa tatgacagtg      300
tctactgctg ctgcagctga aaacatgtat actcagatgg gattagacac caggccatct     360
acaagagaag caggaggaaa agaggaaagc cctccacagg catatcctat tcaaacagta     420
aatggagcac cacaatatgt agcacttgac ccaaaaatgg tgtccatttt tatggaaaag     480
gcaagagaag gactaggagg tgaggaagtt caattatggt ttactgcctt ctctgcaaat     540
ttaacaccta ctgacatggc cacattaata atggccgcac cagggtgcgc tgcagataaa     600
gaaatattgg angaaagctt aaagcaattg acagcagaat atgatcgtac acatcccct      660
gatggtccca gaccattacc ctattttact gcagcagaaa ttatgggcat aggattaact     720
caagaacaac aagcagaagc aagatttgca ccagctagga tgcagtgtag agcatggtat     780
cttgaggcat taggaaaact ggccgccata aaggctaaat ctcctcgagc tgtgcagtta     840
agacaaggag ctaaagaaga ttattcatcc tttatagaca gattgtttgc ccaaatagat     900
caagaacaaa atacagctga agttaagtta tatttaaaac agtcattaag cattgctaat     960
gctaatgcag aatgtaaaaa ggcaatgagc caccttaagc cagaaagtac cctagaagaa    1020
aagttgagag cttgtcaaga gtaggctcca ccaggatata aaatgcaact cttggcagag    1080
gctcttacaa aagttcaagt agtacaatca aaaggatcag accagtgtg ttttaattgt     1140
aaaaaaccag gacatctagc aagacagtgt agagatgtga aaaatgtaa taaatgtgga    1200
aagcctggtc atttagctgc caaatgttgg caaggtggta aaaagaattc gggaaacggg    1260
aaggcgggc gagctgcagc cccagtgaat caagtgcagc aagcagtaat accatctgca    1320
ccttcaatag aggagaaact attggattta taa                                 1353

<210> SEQ ID NO 48
<211> LENGTH: 795
<212> TYPE: DNA
<213> ORGANISM: Feline immunodeficiency virus

<400> SEQUENCE: 48
gttactttaa aagttttgc agtggcagga attctaaata tgactgtatc tactgccaca       60
gcagctgaaa atatgtatgc tcagatggga ttagacacca gaccatctat aaaagaaagt    120
gggggaaaag aagaaggacc tccacaggct tatcctattc aaacagtaaa tggagcacca    180
cagtatgtag cccttgatcc aaaaatggtg tccatttta tggagagagc aagagagggg     240
ctaggaggtg aggaggtcca actgtggttc acagcctttt cagctaattt aacatcaact    300
gatatggcta cattaattat gtccgcacct ggctgtgcag cagttaaaga aattctagat    360
gaaacactga acagatgac agctgagtat gatcgtaccc atcctcctga tgggcctaga    420
ccgctgccct atttcactgc cgcagagatt atggggatag gattaactca agaacaacaa    480
gcagagccca gttttgcacc agccagaatg cagtgtagag catggtacct tgaagcatta    540
ggaaagttgg cggccataaa agccaaatct ccccgagcag tacaattgaa gcagggagct    600
aaagaggact attcctcatt catagataga ctatttgctc aaatagatca agagcagaac    660
acagctgaag taaagctgta tttaaaacaa tcttttaagta tagccaatgc taatccagat    720
tgtaaaagag caatgagtca tcttaaacca gaaagtactt tagaggaaaa actgagggcc    780
```
tgccaagaag tagga 795

<210> SEQ ID NO 49
<211> LENGTH: 795
<212> TYPE: DNA
<213> ORGANISM: Feline immunodeficiency virus

<400> SEQUENCE: 49

| | | | | | |
|---|---|---|---|---|---|
| accactttaa | aagtttttgc | agtggcagga | attctaaata | tgactgtatc | tactgccaca | 60 |
| gcagctgaaa | atatgtatgc | tcagatggga | ttagacacca | gaccatctat | aaaagaaagt | 120 |
| ggggaaaag | aagaaggacc | tccacaggct | tatcctattc | aaacagtaaa | tggagcacca | 180 |
| cagtatgtag | cccttgatcc | aaaaatggtg | tccatttta | tggagaaggc | aagagagggg | 240 |
| ctaggaggtg | aggaggtcca | actgtggttc | acagcctttt | cagctaattt | aacatcaact | 300 |
| gatatggcta | cattaattat | gtccgcacct | ggctgtgcag | cagataaaga | aatcctagat | 360 |
| gaagcactga | aacagatgac | agctgagtat | gatcgtaccc | atcctcctga | tgggcctaga | 420 |
| ccgctgccct | atttcactgc | cgcagagatt | atggggatag | gattaactca | agaaccacaa | 480 |
| gcagagccca | ggtttgcacc | agccagaatg | cagtgtagag | catggtacct | tgaagcatta | 540 |
| ggaaagttgg | cggccataaa | agccaaatct | ccccgagcag | tacaattgaa | gcagggagct | 600 |
| aaagaggact | attcctcatt | catagataga | ctatttgctc | aaatagatca | agagcagaac | 660 |
| acagctgaag | taaagctgta | tttaaaacac | tctttaagta | tagctaatgc | taatccagat | 720 |
| tgtaaaagag | caatgagaca | tcttaaacca | gaaagtactt | tagaggaaaa | actgagggcc | 780 |
| tgccaagaag | tagga | | | | | 795 |

<210> SEQ ID NO 50
<211> LENGTH: 795
<212> TYPE: DNA
<213> ORGANISM: Feline immunodeficiency virus

<400> SEQUENCE: 50

| | | | | | |
|---|---|---|---|---|---|
| accactttaa | aagtttttgc | agtggcagga | attctaaata | tgactgtatc | tactgccaca | 60 |
| gcagctgaaa | atatgtatgc | tcagatggga | ttagacacca | gaccatctat | aaaagaaagt | 120 |
| gggggaaaag | aggaaggacc | tccacaggct | tatcctattc | aaacagtaaa | tggagcacca | 180 |
| cagtatgtag | cccttgatcc | aaaaatggtg | tccatttta | tggagaaggc | aagagagggg | 240 |
| ctaggaggtg | aggaggtcca | actgtggttc | acagcctttt | cagcaaattt | aacatcaact | 300 |
| gatatggcta | cattaattat | gtccgcacct | ggctgtgcag | cagataaagg | aatactagat | 360 |
| gaaacgctga | aacagatgac | agctgagtat | gatcgtaccc | atcctcctga | tgggcctaga | 420 |
| ccgctgccct | atttcactgc | cgcagagatt | atggggatag | gattaactca | agaacaacaa | 480 |
| gcagagccca | ggtttgcacc | agccagaatg | cagtgtagag | catggtacct | tgaagcatta | 540 |
| ggaaagttgg | cggccataaa | agccaaatct | ccccgagcag | tacaattgaa | gcagggagct | 600 |
| aaggaggact | attcctcatt | tatagataga | ctatttgctc | aaatagatca | agagcagaac | 660 |
| acaactgaag | taaagctgta | tttaaaacaa | tctttaagta | tagccaatgc | taatccagat | 720 |
| tgtaaaagag | caatgagtca | tcttaaacca | gaaagtactt | tagaggaaaa | actgagggcc | 780 |
| tgccaagaag | tagga | | | | | 795 |

<210> SEQ ID NO 51
<211> LENGTH: 1350
<212> TYPE: DNA

<213> ORGANISM: Feline immunodeficiency virus

<400> SEQUENCE: 51

| | | | | | |
|---|---|---|---|---|---|
| atggggaatg | gacaggggcg | agactggaaa | atggccatta | agagatgtag | taatgttgct | 60 |
| gtaggagtag | ggagtaagag | taaaagatct | ggagaaggaa | actttagatg | ggccataagg | 120 |
| atggctaatg | taactacagg | acgagaacca | ggtgatatac | cagagacttt | agaacagtta | 180 |
| agatcaatta | tttgtgattt | acaaggcaga | agagaacact | atggatctag | taaggaaatt | 240 |
| gatatggcaa | ttaccacttt | aaaagttttt | gcagtggcag | gaattctaaa | tatgactgta | 300 |
| tctactgcca | cagcagctga | aaatatgtat | gctcagatgg | gattagacac | cagaccatct | 360 |
| gtaaaagaaa | gtgggggaaa | agaagaagga | cctccacagg | cttatcctat | tcaaacagta | 420 |
| aatggagcac | cacagtatgt | agcccttgat | ccaaaaatgg | tgtccatttt | tatggagaag | 480 |
| gcaagagagg | ggctaggagg | tgaggaggtc | caactgtggt | tcacagcctt | ttcagctaat | 540 |
| ttaacatcaa | ctgatatggc | tacattaatt | atgtccgcac | ctggctgtgc | agcagataaa | 600 |
| gaaatcctag | atgaaacact | gaaacagatg | acagctgagt | atgatcgtac | ccatcctcct | 660 |
| gatgggccta | accgctgccc | tatttcact | gccgcagaga | ttatggggat | aggattaact | 720 |
| caagaacaac | aagcagagcc | caggtttgca | ccagccagaa | tgcagtgtag | agcatggtac | 780 |
| cttgaagcat | taggaaagtt | ggcggccata | aaagccaaat | ctccccgagc | agtacaattg | 840 |
| aagcagggag | ctaaagagga | ctattcctca | tttatagata | gactatttgc | tcaaatagat | 900 |
| caagagcaga | acacagctga | agtaaagctg | tatttaaaac | aatctttaag | tatagccaat | 960 |
| gctaatccag | attgtaaaag | agcaatgagt | catcttaaac | cagaaagtac | tttagaggaa | 1020 |
| aaactgaggg | cctgccaaga | agtaggatca | ccaggatata | aaatgcaatt | gctggcggaa | 1080 |
| gctctcacaa | gggttcaaac | agttcaaaca | aaaggaccaa | ggctagtgtg | tttcaattgt | 1140 |
| aaaaaaccag | gccacctggc | tagacaatgt | aaagaagcga | agagatgtaa | taactgtgga | 1200 |
| aaacctggtc | acttagctgc | taattgctgg | caaggaggta | ggaaaacctc | gggaaacgag | 1260 |
| aaggtggggc | gagctgcagc | cccagtaaac | caagtgcagc | aaatagtacc | atctgcacct | 1320 |
| ccaatggagg | agaaactatt | agatttataa | | | | 1350 |

<210> SEQ ID NO 52
<211> LENGTH: 795
<212> TYPE: DNA
<213> ORGANISM: Feline immunodeficiency virus

<400> SEQUENCE: 52

| | | | | | |
|---|---|---|---|---|---|
| accaccttaa | aagtttttgc | agtggcagga | attctaaata | tgactgtatc | tactgccaca | 60 |
| gcagctgaaa | atatgtatgc | tcagatggga | ttagacacca | gaccatctat | aaaagaaagt | 120 |
| gggggaaaag | aagaaggacc | accacaggct | tatcctattc | aaacagtaaa | tggagcacca | 180 |
| cagtatgtag | cccttgatcc | aaaaatggtg | tccatttta | tggagaaggc | aagagagggg | 240 |
| ctaggaggtg | aggaggtcca | actgtggttc | acagccttct | cagcaaattt | aacatcaact | 300 |
| gatatggcca | cattaatcat | gtccgcacct | ggctgtgcag | cagataaaga | aatactagat | 360 |
| gaaacactga | acagatgac | agctgagtat | gatcgtaccc | atcctcctga | tgggcctaga | 420 |
| ccgctgccct | atttcactgc | cgcagagatt | atggggatag | gattaactca | agaacaacaa | 480 |
| gcagagccca | ggtttgcacc | agccagaatg | cagtgtagag | catggtacct | tgaagcatta | 540 |
| ggaaagttgg | cggccataaa | agccaaatct | ccccgagcag | tacaattgaa | gcagggagct | 600 |
| aaagaggact | attcctcatt | tatagataga | ctattcgctc | aaatagatca | agagcagaac | 660 |

```
acagctgaag taaagctgta tttaaaacaa tctttaagta tagccaatgc taatccagat      720
tgtaaaagag caatgagtca tcttaaacca gaaagtactt tagaggaaaa actgagggcc      780
tgccaagaag tagga                                                       795
```

<210> SEQ ID NO 53
<211> LENGTH: 1344
<212> TYPE: DNA
<213> ORGANISM: Feline immunodeficiency virus

<400> SEQUENCE: 53

```
aatggacagg ggcgagattg gaaaacggcc ataaagagat gtagtaatgt tgctgtaggt       60
acgggacaac gaagtaagaa gttcggggaa ggaaatttta gatgggcctt gagaatggcc      120
aatgtaacta caggacgtga acctggtgat ataccagaga ccttagatca actgagagta      180
cttatctgtg atttacagga agaagggag aaatttggat ctagcaaaga acttgatatg       240
gcaatcctca ctctaaaagt ttttgcagta gcaggagtct taaatatgtc tgtatctact      300
gctactgccg ctgaaaatat gtatgctcag atggattag atactagacc atctttaaag      360
gaggcaggag aaagataga ggagcctcca caggcatatc ccatccaaac aataaatgga       420
gcgccacaat atgtagccct ggatcctaaa atggtgtcca tttttatgga aaaagcaaga      480
gaaggattag gaggagagga ggtccaacta tggtttactg cattttcagc taatctaaca      540
tcaactgata tggctacatt aatcatgtct gcaccaggtt gtgcagcaga taaggaaatc      600
ttagatgaaa ctctaaaaca gatgacagca gagtatgatc gaacccaccc tccggatggg      660
cccagacctc tgccatattt tactgcagca gaaattatgg aatagggtt aactcaggaa      720 caacaagcag aacctagatt tgcaccagca agaatgcagt gtagagcatg gtatctcgaa      780
gcattgagta agttggcagc cctaaaggct aaatctcctc gagctgtgca gatgaaacaa      840
ggggtgaagg aggactacgc ctcgttcata gatcgattgt ttgctcagat agatcaagag      900
caaaatacag ctgaagtaaa gttgtattta aaacagtctt taagcatagc taatgccaac      960
ccagactgta gagggcaat gagccatttg aaaccagaaa gtaccctaga gaaaagttg     1020 agggcctgcc aagaaatagg atcatcaggg tataaaatgc aacttttggc agaagctctt     1080
acaaaagttc aaacagttca agcaaaagga ccaaaaccag tatgttttaa ttgtaaaaaa     1140
ccaggccatc tagctagaca atgtagagat gtgaaaagt gtaataaatg gaaagcct      1200 ggtcatttgg ctgccaaatg ttggcaagga agcagaaatg cttcgggaaa cgggaagatg     1260
gggcgagctg cagccccagt aaaccaagtg cagcaagcag tgccatctgc tcctccagtg     1320
gaagagaagt tgttagattt ataa                                           1344
```

<210> SEQ ID NO 54
<211> LENGTH: 795
<212> TYPE: DNA
<213> ORGANISM: Feline immunodeficiency virus

<400> SEQUENCE: 54

```
ctcactctaa aagttttgc agtagcagga atcttaaata tgactgtatc taccgctact       60
gccgctgaaa atatgtatgc tcaaatggga ttagatacta gaccatcttt aaaggaggca      120
ggaggaaaag tagaggagcc tccgcaggca tatcctatcc aaacaataaa tggagcacca      180
caatatgtgg ccctggatcc taaaatggtg tccatttttca tggaaaaggc aagagaagga      240
ttaggaggag aggaagttca attatggttt actgcatttt cagctaattt aacatcaact      300
```

-continued

```
gatatggcta cattaatcat gtctgcacca ggttgtgcag cagataagga aattttagat    360
gagactctaa aacagatgac agcggagtat gatcgaaccc accctccgga tgggcccaga    420
cctctgccat actttactgc agcagaaatt atgggaatag gattaactca ggaacaacaa    480
gcagaaccta gatttgcacc agcaagaatg cagtgtagag catggtatct cgaagcattg    540
agtaagttgg cagccctaaa ggctaaatct cctcgagctg tgcagatgaa acaagggtg     600 aaggaggact acgcctcgtt catagatcga ttgtttgctc agatagatca agagcaaaat    660
acagctgaag taaagttgta tttaaaacag tctttaagta tagctaatgc taacccagac    720
tgtaagaagg caatgagcca tttaaagcca gaaagtaccc tagaagagaa gttgagggcc    780
tgccaagaaa tagga                                                    795
```

```
<210> SEQ ID NO 55
<211> LENGTH: 322
<212> TYPE: DNA
<213> ORGANISM: Feline immunodeficiency virus
<220> FEATURE:
<221> NAME/KEY: misc_feature
<222> LOCATION: (1)..(2)
<223> OTHER INFORMATION: n = undetermined nucleotide
<220> FEATURE:
<221> NAME/KEY: misc_feature
<222> LOCATION: (4)..(4)
<223> OTHER INFORMATION: n = undetermined nucleotide
<220> FEATURE:
<221> NAME/KEY: misc_feature
<222> LOCATION: (7)..(7)
<223> OTHER INFORMATION: n = undetermined nucleotide
<220> FEATURE:
<221> NAME/KEY: misc_feature
<222> LOCATION: (14)..(14)
<223> OTHER INFORMATION: n = undetermined nucleotide
<220> FEATURE:
<221> NAME/KEY: misc_feature
<222> LOCATION: (16)..(16)
<223> OTHER INFORMATION: n = undetermined nucleotide
<220> FEATURE:
<221> NAME/KEY: misc_feature
<222> LOCATION: (22)..(23)
<223> OTHER INFORMATION: n = undetermined nucleotide
<220> FEATURE:
<221> NAME/KEY: misc_feature
<222> LOCATION: (28)..(28)
<223> OTHER INFORMATION: n = undetermined nucleotide
<220> FEATURE:
<221> NAME/KEY: misc_feature
<222> LOCATION: (40)..(40)
<223> OTHER INFORMATION: n = undetermined nucleotide
<220> FEATURE:
<221> NAME/KEY: misc_feature
<222> LOCATION: (43)..(43)
<223> OTHER INFORMATION: n = undetermined nucleotide
<220> FEATURE:
<221> NAME/KEY: misc_feature
<222> LOCATION: (46)..(46)
<223> OTHER INFORMATION: n = undetermined nucleotide
<220> FEATURE:
<221> NAME/KEY: misc_feature
<222> LOCATION: (53)..(55)
<223> OTHER INFORMATION: n = undetermined nucleotide
<220> FEATURE:
<221> NAME/KEY: misc_feature
<222> LOCATION: (57)..(58)
<223> OTHER INFORMATION: n = undetermined nucleotide
<220> FEATURE:
<221> NAME/KEY: misc_feature
<222> LOCATION: (61)..(64)
<223> OTHER INFORMATION: n = undetermined nucleotide
<220> FEATURE:
<221> NAME/KEY: misc_feature
<222> LOCATION: (67)..(67)
<223> OTHER INFORMATION: n = undetermined nucleotide
```

-continued

```
<220> FEATURE:
<221> NAME/KEY: misc_feature
<222> LOCATION: (73)..(73)
<223> OTHER INFORMATION: n = undetermined nucleotide
<220> FEATURE:
<221> NAME/KEY: misc_feature
<222> LOCATION: (75)..(76)
<223> OTHER INFORMATION: n = undetermined nucleotide
<220> FEATURE:
<221> NAME/KEY: misc_feature
<222> LOCATION: (79)..(80)
<223> OTHER INFORMATION: n = undetermined nucleotide
<220> FEATURE:
<221> NAME/KEY: misc_feature
<222> LOCATION: (82)..(83)
<223> OTHER INFORMATION: n = undetermined nucleotide
<220> FEATURE:
<221> NAME/KEY: misc_feature
<222> LOCATION: (95)..(95)
<223> OTHER INFORMATION: n = undetermined nucleotide
<220> FEATURE:
<221> NAME/KEY: misc_feature
<222> LOCATION: (97)..(97)
<223> OTHER INFORMATION: n = undetermined nucleotide
<220> FEATURE:
<221> NAME/KEY: misc_feature
<222> LOCATION: (104)..(104)
<223> OTHER INFORMATION: n = undetermined nucleotide
<220> FEATURE:
<221> NAME/KEY: misc_feature
<222> LOCATION: (111)..(112)
<223> OTHER INFORMATION: n = undetermined nucleotide
<220> FEATURE:
<221> NAME/KEY: misc_feature
<222> LOCATION: (121)..(121)
<223> OTHER INFORMATION: n = undetermined nucleotide
<220> FEATURE:
<221> NAME/KEY: misc_feature
<222> LOCATION: (126)..(126)
<223> OTHER INFORMATION: n = undetermined nucleotide
<220> FEATURE:
<221> NAME/KEY: misc_feature
<222> LOCATION: (128)..(129)
<223> OTHER INFORMATION: n = undetermined nucleotide
<220> FEATURE:
<221> NAME/KEY: misc_feature
<222> LOCATION: (131)..(131)
<223> OTHER INFORMATION: n = undetermined nucleotide
<220> FEATURE:
<221> NAME/KEY: misc_feature
<222> LOCATION: (137)..(137)
<223> OTHER INFORMATION: n = undetermined nucleotide
<220> FEATURE:
<221> NAME/KEY: misc_feature
<222> LOCATION: (140)..(140)
<223> OTHER INFORMATION: n = undetermined nucleotide
<220> FEATURE:
<221> NAME/KEY: misc_feature
<222> LOCATION: (143)..(143)
<223> OTHER INFORMATION: n = undetermined nucleotide
<220> FEATURE:
<221> NAME/KEY: misc_feature
<222> LOCATION: (146)..(146)
<223> OTHER INFORMATION: n = undetermined nucleotide
<220> FEATURE:
<221> NAME/KEY: misc_feature
<222> LOCATION: (158)..(158)
<223> OTHER INFORMATION: n = undetermined nucleotide
<220> FEATURE:
<221> NAME/KEY: misc_feature
<222> LOCATION: (160)..(160)
<223> OTHER INFORMATION: n = undetermined nucleotide
<220> FEATURE:
<221> NAME/KEY: misc_feature
<222> LOCATION: (164)..(164)
<223> OTHER INFORMATION: n = undetermined nucleotide
<220> FEATURE:
<221> NAME/KEY: misc_feature
<222> LOCATION: (170)..(170)
```

```
<223> OTHER INFORMATION: n = undetermined nucleotide
<220> FEATURE:
<221> NAME/KEY: misc_feature
<222> LOCATION: (173)..(173)
<223> OTHER INFORMATION: n = undetermined nucleotide
<220> FEATURE:
<221> NAME/KEY: misc_feature
<222> LOCATION: (182)..(182)
<223> OTHER INFORMATION: n = undetermined nucleotide
<220> FEATURE:
<221> NAME/KEY: misc_feature
<222> LOCATION: (185)..(186)
<223> OTHER INFORMATION: n = undetermined nucleotide
<220> FEATURE:
<221> NAME/KEY: misc_feature
<222> LOCATION: (194)..(194)
<223> OTHER INFORMATION: n = undetermined nucleotide
<220> FEATURE:
<221> NAME/KEY: misc_feature
<222> LOCATION: (197)..(197)
<223> OTHER INFORMATION: n = undetermined nucleotide
<220> FEATURE:
<221> NAME/KEY: misc_feature
<222> LOCATION: (200)..(200)
<223> OTHER INFORMATION: n = undetermined nucleotide
<220> FEATURE:
<221> NAME/KEY: misc_feature
<222> LOCATION: (203)..(203)
<223> OTHER INFORMATION: n = undetermined nucleotide
<220> FEATURE:
<221> NAME/KEY: misc_feature
<222> LOCATION: (208)..(208)
<223> OTHER INFORMATION: n = undetermined nucleotide
<220> FEATURE:
<221> NAME/KEY: misc_feature
<222> LOCATION: (211)..(211)
<223> OTHER INFORMATION: n = undetermined nucleotide
<220> FEATURE:
<221> NAME/KEY: misc_feature
<222> LOCATION: (214)..(214)
<223> OTHER INFORMATION: n = undetermined nucleotide
<220> FEATURE:
<221> NAME/KEY: misc_feature
<222> LOCATION: (217)..(217)
<223> OTHER INFORMATION: n = undetermined nucleotide
<220> FEATURE:
<221> NAME/KEY: misc_feature
<222> LOCATION: (220)..(221)
<223> OTHER INFORMATION: n = undetermined nucleotide
<220> FEATURE:
<221> NAME/KEY: misc_feature
<222> LOCATION: (223)..(223)
<223> OTHER INFORMATION: n = undetermined nucleotide
<220> FEATURE:
<221> NAME/KEY: misc_feature
<222> LOCATION: (229)..(229)
<223> OTHER INFORMATION: n = undetermined nucleotide
<220> FEATURE:
<221> NAME/KEY: misc_feature
<222> LOCATION: (232)..(232)
<223> OTHER INFORMATION: n = undetermined nucleotide
<220> FEATURE:
<221> NAME/KEY: misc_feature
<222> LOCATION: (235)..(235)
<223> OTHER INFORMATION: n = undetermined nucleotide
<220> FEATURE:
<221> NAME/KEY: misc_feature
<222> LOCATION: (238)..(238)
<223> OTHER INFORMATION: n = undetermined nucleotide
<220> FEATURE:
<221> NAME/KEY: misc_feature
<222> LOCATION: (241)..(241)
<223> OTHER INFORMATION: n = undetermined nucleotide
<220> FEATURE:
<221> NAME/KEY: misc_feature
<222> LOCATION: (244)..(244)
<223> OTHER INFORMATION: n = undetermined nucleotide
<220> FEATURE:
<221> NAME/KEY: misc_feature
```

```
<222> LOCATION: (248)..(248)
<223> OTHER INFORMATION: n = undetermined nucleotide
<220> FEATURE:
<221> NAME/KEY: misc_feature
<222> LOCATION: (253)..(254)
<223> OTHER INFORMATION: n = undetermined nucleotide
<220> FEATURE:
<221> NAME/KEY: misc_feature
<222> LOCATION: (256)..(256)
<223> OTHER INFORMATION: n = undetermined nucleotide
<220> FEATURE:
<221> NAME/KEY: misc_feature
<222> LOCATION: (262)..(262)
<223> OTHER INFORMATION: n = undetermined nucleotide
<220> FEATURE:
<221> NAME/KEY: misc_feature
<222> LOCATION: (268)..(268)
<223> OTHER INFORMATION: n = undetermined nucleotide
<220> FEATURE:
<221> NAME/KEY: misc_feature
<222> LOCATION: (277)..(277)
<223> OTHER INFORMATION: n = undetermined nucleotide
<220> FEATURE:
<221> NAME/KEY: misc_feature
<222> LOCATION: (281)..(281)
<223> OTHER INFORMATION: n = undetermined nucleotide
<220> FEATURE:
<221> NAME/KEY: misc_feature
<222> LOCATION: (283)..(283)
<223> OTHER INFORMATION: n = undetermined nucleotide
<220> FEATURE:
<221> NAME/KEY: misc_feature
<222> LOCATION: (286)..(286)
<223> OTHER INFORMATION: n = undetermined nucleotide
<220> FEATURE:
<221> NAME/KEY: misc_feature
<222> LOCATION: (289)..(289)
<223> OTHER INFORMATION: n = undetermined nucleotide
<220> FEATURE:
<221> NAME/KEY: misc_feature
<222> LOCATION: (292)..(292)
<223> OTHER INFORMATION: n = undetermined nucleotide
<220> FEATURE:
<221> NAME/KEY: misc_feature
<222> LOCATION: (295)..(295)
<223> OTHER INFORMATION: n = undetermined nucleotide
<220> FEATURE:
<221> NAME/KEY: misc_feature
<222> LOCATION: (298)..(298)
<223> OTHER INFORMATION: n = undetermined nucleotide
<220> FEATURE:
<221> NAME/KEY: misc_feature
<222> LOCATION: (303)..(303)
<223> OTHER INFORMATION: n = undetermined nucleotide
<220> FEATURE:
<221> NAME/KEY: misc_feature
<222> LOCATION: (307)..(307)
<223> OTHER INFORMATION: n = undetermined nucleotide
<220> FEATURE:
<221> NAME/KEY: misc_feature
<222> LOCATION: (310)..(310)
<223> OTHER INFORMATION: n = undetermined nucleotide
<220> FEATURE:
<221> NAME/KEY: misc_feature
<222> LOCATION: (313)..(314)
<223> OTHER INFORMATION: n = undetermined nucleotide
<220> FEATURE:
<221> NAME/KEY: misc_feature
<222> LOCATION: (316)..(316)
<223> OTHER INFORMATION: n = undetermined nucleotide
<220> FEATURE:
<221> NAME/KEY: misc_feature
<222> LOCATION: (319)..(319)
<223> OTHER INFORMATION: n = undetermined nucleotide

<400> SEQUENCE: 55
nncngcngct gaananatgt annctcanat gggattagan acnagnccat ctnnnannga      60
```

```
nnnnggngga aangnnganm gnncctccac aggcntntcc tatncaaaca nnaaatggag    120
naccananna ngtagcnctn ganccnaaaa tggtgtcnan tttnatggan aangcaagag    180
anggnntagg aggngangan gtcaggnga ngangtncan ntntggttna cngcnttntc    240
ngcnaatnta acnncnactg anatggcnac attaatnatg ncngcnccng gntgngcngc    300
agntaangan atnntngang aa                                            322
```

```
<210> SEQ ID NO 56
<211> LENGTH: 321
<212> TYPE: DNA
<213> ORGANISM: Feline immunodeficiency virus

<400> SEQUENCE: 56
tgctgcagct gaaaatatgt attctcaaat gggattagac actaggccat ctatgaaaga    60
agcaggtgga aaagaggaag cccctccaca ggcatatcct attcaaacag taaatggagt   120
accacaatat gtagcacttg acccaaaaat ggtgtccatt tttatggaaa aggcaagaga   180
aggactagga ggtgaggaag ttcaggtgag gaagttcaac tatggtttac tgccttctct   240
gcaaatttaa cacctactga catggccaca ttaataatgg ccgcaccagg gtgcgctgca   300
gataaagaaa tattggatga a                                             321
```

```
<210> SEQ ID NO 57
<211> LENGTH: 321
<212> TYPE: DNA
<213> ORGANISM: Feline immunodeficiency virus
<220> FEATURE:
<221> NAME/KEY: misc_feature
<222> LOCATION: (318)..(318)
<223> OTHER INFORMATION: n = undetermined nucleotide

<400> SEQUENCE: 57
tgctgcagct gaaaacatgt atactcagat gggattagac accaggccat ctacaagaga    60
agcaggagga aaagaggaaa gccctccaca ggcatatcct attcaaacag taaatggagc   120
accacaatat gtagcacttg acccaaaaat ggtgtccatt tttatggaaa aggcaagaga   180
aggactagga ggtgaggaag ttcaggtgag gaagttcaat tatggtttac tgccttctct   240
gcaaatttaa cacctactga catggccaca ttaataatgg ccgcaccagg gtgcgctgca   300
gataaagaaa tattgganga a                                             321
```

```
<210> SEQ ID NO 58
<211> LENGTH: 321
<212> TYPE: DNA
<213> ORGANISM: Feline immunodeficiency virus

<400> SEQUENCE: 58
tgctgcagct gaaaatatgt acactcagat gggattagac actagaccat ctatgagaga    60
agcaggagga aaagaggaaa gccctccaca ggcatctcct attcaaacag caaatggagc   120
accacaatat gtagcacttg acccaaaaat ggtgtccatt tttatggaaa aggcaagaga   180
aggattagga ggtgaggaag ttcaggtgag gaagttcagc tatggtttac tgccttctct   240
gcaaatttaa cacctactga catggccaca ttaataatgg ccgcaccagg gtgcgctgca   300
gataaagaaa tattggatga a                                             321
```

```
<210> SEQ ID NO 59
<211> LENGTH: 321
<212> TYPE: DNA
<213> ORGANISM: Feline immunodeficiency virus
```

<400> SEQUENCE: 59

```
tgctgcagct gaaaatatgt atactcagat gggattagac actagaccat ctacaaagga      60
agctggagga aaagaggaag gccctccaca ggcatatcct attcaaacag taaatggagc     120
accacaatat gtagctcttg acccaaaaat ggtgtctatt ttcatggaaa aggcaagaga    180
agggttagga ggtgaagaag ttcaggtgaa gaagttcaac tatggttcac agccttctct    240
gcaaatttaa cacctactga catggccaca ttaataatgg ccgcaccagg gtgcgctgca    300
gataaagaaa tattggatga a                                              321
```

<210> SEQ ID NO 60
<211> LENGTH: 321
<212> TYPE: DNA
<213> ORGANISM: Feline immunodeficiency virus

<400> SEQUENCE: 60

```
tactgccgct gaaaatatgt atgctcagat gggattagat actagaccat ctttaaagga      60
ggcaggagga aaggtagagg agcctccaca ggcatatcct atccaaacaa taaatggagc    120
accacaatat gtagccctgg atcctaaaat ggtgtccatt tttatggaaa aagcaagaga    180
aggattagga ggagaggagg tccaggagag gaggtccaac tatggtttac tgcattttca    240
gctaatctaa catcaactga tatggctaca ttaatcatgt ctgcaccagg ttgtgcagca    300
gataaggaga tcttagatga a                                              321
```

<210> SEQ ID NO 61
<211> LENGTH: 321
<212> TYPE: DNA
<213> ORGANISM: Feline immunodeficiency virus

<400> SEQUENCE: 61

```
cacagcagct gaaaatatgt atgctcagat gggattagac accagaccat ctataaaaga      60
aagtggggga aaagaagaag gacctccaca ggcttatcct attcaaacag taaatggagc    120
accacagtat gtagcccttg atccaaaaat ggtgtccatt tttatggaga aggcaagaga    180
ggggctagga ggtgaggagg tccaggtgag gaggtccaac tgtggttcac agccttttca    240
gctaatttaa catcaactga tatggctaca ttaattatgt ccgcacctgg ctgtgcagca    300
gttaaagaaa ttctagatga a                                              321
```

<210> SEQ ID NO 62
<211> LENGTH: 321
<212> TYPE: DNA
<213> ORGANISM: Feline immunodeficiency virus

<400> SEQUENCE: 62

```
cacagcagct gaaaatatgt atgctcagat gggattagac accagaccat ctgtaaaaga      60
aagtggggga aaagaagaag gacctccaca ggcttatcct attcaaacag taaatggagc    120
accacagtat gtagcccttg atccaaaaat ggtgtccatt tttatggaga aggcaagaga    180
ggggctagga ggtgaggagg tccaggtgag gaggtccaac tgtggttcac agccttttca    240
gctaatttaa catcaactga tatggctaca ttaattatgt ccgcacctgg ctgtgcagca    300
gataaagaaa tcctagatga a                                              321
```

<210> SEQ ID NO 63
<211> LENGTH: 19
<212> TYPE: DNA

```
<213> ORGANISM: Artificial Sequence
<220> FEATURE:
<223> OTHER INFORMATION: synthetic oligonucleotide RT Forward

<400> SEQUENCE: 63
agccctccac aggcatctc                                                    19

<210> SEQ ID NO 64
<211> LENGTH: 31
<212> TYPE: DNA
<213> ORGANISM: Artificial Sequence
<220> FEATURE:
<223> OTHER INFORMATION: synthetic oligonucleotide RT Probe

<400> SEQUENCE: 64
attcaaacag caaatggagc accacaatat g                                      31

<210> SEQ ID NO 65
<211> LENGTH: 21
<212> TYPE: DNA
<213> ORGANISM: Artificial Sequence
<220> FEATURE:
<223> OTHER INFORMATION: synthetic oligonucleotide RT Reverse

<400> SEQUENCE: 65
ttgacccaaa aatggtgtcc a                                                 21

<210> SEQ ID NO 66
<211> LENGTH: 321
<212> TYPE: DNA
<213> ORGANISM: Feline immunodeficiency virus

<400> SEQUENCE: 66
cgcagcagct gaacacatgt atgctcagat gggattagat accagaccat ctataaaga        60 aagtggggga aagaagaag gacctccaca ggcttatcct attcaaacag taaatggagc       120
accacagtat gtagcccttg acccaaaaat ggtgtccatt tttatggaaa agcaagaga       180 ggggctagga ggtgaggagg tccaggtgag gaggtccaac tgtggttcac agcctttct       240 gctaatttaa cttcaactga tatggctaca ttaattatgt ctgcgcctgg ctgtgcagca      300
gataaagaga tcttagatga a                                                321

<210> SEQ ID NO 67
<211> LENGTH: 76
<212> TYPE: DNA
<213> ORGANISM: Feline immunodeficiency virus

<400> SEQUENCE: 67
tagccctcca caggcatatc ctattcaaac agtaaatgga gtaccataac acgtagcact       60
tgacccaaaa atggtg                                                      76

<210> SEQ ID NO 68
<211> LENGTH: 80
<212> TYPE: DNA
<213> ORGANISM: Feline immunodeficiency virus

<400> SEQUENCE: 68
agccctccac aggcatatcc tattcaaaca gtaaatggag taccacaata tgtagcgctt       60
gacccaaaaa tggtgtccaa                                                  80
```